United States Patent [19]
Rota et al.

[11] Patent Number: 5,374,717
[45] Date of Patent: Dec. 20, 1994

[54] SEQUENCES OF THE HEMAGGLUTININS OF RECENT STRAINS OF INFLUENZA TYPE B VIRUS

[75] Inventors: Paul A. Rota, Decatur; Mark L. Hemphill, Lawrenceville, both of Ga.

[73] Assignee: The United States of America as represented by the Secretary of Health and Human Services, Washington, D.C.

[21] Appl. No.: 954,840

[22] Filed: Sep. 30, 1992

[51] Int. Cl.$^5$ .............................................. C07H 21/04
[52] U.S. Cl. ................................ 536/23.72; 435/235.1
[58] Field of Search ..................... 536/23.72; 435/235.1

[56] References Cited

U.S. PATENT DOCUMENTS

| | | | |
|---|---|---|---|
| 4,659,669 | 4/1987 | Kleid et al. | 435/243 |
| 4,752,473 | 6/1988 | Nayak et al. | 424/88 |
| 5,136,019 | 8/1992 | Judd et al. | 530/326 |
| 5,162,112 | 11/1992 | Oxford et al. | 424/89 |

OTHER PUBLICATIONS

Harmon, M. W., et al., "Immunoassay for Serolgic Diagnosis of Influenza Type A Using Recombinant DNA Produced Nucleoprotein Antigen and Monoclonal Anitbody to Human IgG," *Journal of Medical Virology*, 27, 25–30 (1989).

Rota, P. A., et al., "Cocirculation of Two Distinct Evolutionary Lineages of Influenza Type B Virus since 1983," *Virology* 175, 59–68 (1990).

Yamashita, et al., "Influenza B Virus Evolution: Co-circulating Lineages and Comparison of Evolutionary Pattern with those of Influenza A and C viruses," *Virology* 163, 112–122 (1988).

Air, G. M., et al., "Evolutionary changes in influenza B are not primarily governed by antibody selection," *Proc. Natl Acad. Sci. USA* 87, 3884–3888 (May 1990).

Kanegae, Y., et al., "Evolutionary Pattern of the Hemagglutinin Gene of Influenza B Viruses Isolated in Japan: Cocirculating Lineages in the Same Epidemic Season," *Journal of Virology* 64:6, 2860–2865 (Jun. 1990).

Kinnunen, et al., "Evolution of influenza B/Victoria/2/87–like viruses: occurrence of a genetically conserved virus under conditions of low epidemic activity," *Journal of General Virology* 73, 773–736 (1992).

Bootman, J. S., and Robertson, J. S., "Sequence Analysis of the Hemagglutinin of B/Ann Arbor/1/86, an Epidemiologically Significant Variant of Influenza B Virus," *Virology* 166, 271–274 (1988).

Rota, Paul A., "Antigenic and genetic characterization of the haemagglutinins of recent cocirculating strains of influenza B virus," *Journal of General Virology* 73:2737–2742 (1992).

Primary Examiner—Margaret Parr
Assistant Examiner—Scott W. Houtteman
Attorney, Agent, or Firm—Townsend and Townsend Khourie and Crew

[57] ABSTRACT

The invention provides sequence analyses for recent strains of Influenza Type B Virus.

8 Claims, 8 Drawing Sheets

FIG. 5A.

B/HONG KONG/22/89

WITH ENZYMES: *

| | |
|---|---|
| | 1086 |
| BbsI | 2 GAAGACnn'nnnn_ |
| Bce83I | 2 CTTGAGnnnnnnnnnnn_nn' |
| BglII | 1 A'GATC_T |
| BsaI | 1 GGTCTCn'nnnn_ |
| BsgI | 2 GTGCAGnnnnnnnnnnn_nn' |
| Bspl286I | 1 G_dGCh'C |
| Bspl407I | 1 T'GTAC_A |
| BstYI | 2 r'GATC_y |
| Bsu36I | 1 CC'TnA_GG |
| DrdII | 1 GAACCA |
| EcoO109I | 2 rG'GnC_Cy |
| Esp3I | 1 CGTCTCn nnnn_ |
| FspI | 1 TGC'GCA |
| HaeI | 1 wGG'CCw |
| HgiAI | 1 G_wGCw'C |
| HgiEII | 1 ACCnnnnnGGT |
| HindIII | 2 A'AGCT_T |
| MmeI | 1 TCCrACnnnnnnnnnnn_nn' |
| MslI | 1 CAynnnrTG |
| MunI | 1 C'AATT_G |
| NspI | 1 r_CATGy |
| Psp5II | 2 rG'GwC_Cy |
| Psp1406I | 2 AA'CG_TT |
| RleAI | 1 CCCACAnnnnnnnn_nn' |
| SfcI | 1 C'TryA_G |
| StyI | 2 C'CwwG_G |
| TaqII-2 | 1 CACCCAnnnnnnnn_nn' |
| TthIIII | 2 CAArCAnnnnnnnnn_nn' |

B/HONG KONG/22/89

ENZYMES THAT DO CUT:

| | | | | | |
|---|---|---|---|---|---|
| BbsI | Bce83I | BglII | BsaI | Bspl286I | Bspl407I | BstYI |
| Bsu36I | DrdII | EcoO109I | Esp3I | HaeI | HgiAI | HgiEII |
| HindIII | MmeI | MslI | MunI | Psp5II | Pspl406I | RleAI |
| SfcI | StyI | TaqII-2 | TthIIII | | | |

ENZYMES THAT DO NOT CUT:

| | | | | | |
|---|---|---|---|---|---|
| AatII | AccI | AflII | AflIII | AgeI | AlwNI | ApaBI |
| ApaLI | ApoI | AscI | AseI | AvaI | AvrII | ApoI | BaeI | BamHI |
| BanI | BanII | BcgI | BcgI | BclI | BglI | BpmI | BpuIOI |
| BpuIO2I | BsaAI | BsaBI | BsaHI | BsaWI | BsiI | BsiEI | BsmI |
| BspEI | BspGI | BspHI | BspBI | BsrBI | BsrFI | BssHII | BstIIO7I |
| BstEII | BstXI | ClaI | DraI | DraIII | DrdI | DsaI | EaeI |
| EagI | EamlIO5I | EarI | EoiI | Eco47III | Eco57I | EcoNI | EcoRI |
| EcoRV | FseI | GdiII | HaeII | HindII | HpaI | KpnI | MluI |
| MscI | NaeI | NarI | NcoI | NdeI | NheI | NotI | NruI |
| NsiI | NspV | NspBII | PacI | PfIIIO8I | PfIMI | PmeI | PmlI |
| PshAI | PstI | PvuI | PvuII | RsrII | SacI | SacII | SalI |
| SapI | ScaI | SfiI | SgrAI | SmaI | SnaBI | SpeI | SphI |
| SrfI | Sse8387I | SspI | StuI | SunI | SwaI | TaqII-1 | TthIIII |
| XbaI | XcmI | XhoI | XmnI | | | | |

B/TEXAS/358I/88 HAI

WITH ENZYMES: *

| Enzyme | Count | Recognition site |
|---|---|---|
| BanI | | 1086 |
| BbsI | 1 | G'GyrC_C |
| Bce83I | 2 | GAAGACnn'nnn_ |
| BglII | | CTTGAGnnnnnnnnn_nn' |
| BsaI | 1 | A'GATC_T |
| BsgI | 1 | GGTCTCnnnn_ |
| Bsp1407I | 3 | GTGCAGnnnnnnnnn_nn' |
| BspGI | | T'GTAC_A |
| BstYI | | CTGGAC |
| Bsu36I | 2 | r'GATC_y |
| DrdII | 1 | CC'TnA_GG |
| EaeI | 1 | GAACCA |
| EcoO109I | 2 | y'GGCC_r |
| FspI | 1 | rG'GnC_Cy |
| HaeI | | TGC'GCA |
| HgiEII | 2 | wGG'CCw |
| HindIII | 1 | APCnnnnnnGGT |
| MscI | 1 | A'AGCT_T |
| MslI | | TGG'CCA |
| NspI | 1 | CAynnnrTG |
| Psp5II | | r_CATG'y |
| Psp1406I | 2 | rG'GwC_Cy |
| RleAI | 1 | AA'CG_TT |
| SphI | 1 | CCCACAnnnnnnn_nnn' |
| StyI | | G_CATG'C |
| TaqII-1 | | C'CwwG_G |
| TaqII-2 | 2 | GACCGAnnnnnnnn_nn' |
| TthIII II | 2 | CACCGAnnnnnnn_nn' |
| | 2 | CAArCAnnnnnnnn_nn' |

B/TEXAS/3581/88 HAI

ENZYMES THAT DO CUT:

| | | | | | |
|---|---|---|---|---|---|
| BanI | BbsI | Bce83I | BglII | BsaI | Bspl407I | BspGI |
| BstYI | Bsu36I | DrdII | EaeI | EcoO109I | FspI | HgiEII |
| HindIII | | MslI | Nsp

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 1086 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 46..1086
        ( D ) OTHER INFORMATION: /label=PS89

( x i ) SEQUENCE DESCRIPTION: SEQ ID NO:1:

```
ATGAAGGCAA  TAATTGTACT  ACTCATGGTA  GTAACATCCA  ATGCA GAT CGA ATC              54
                                                      Asp Arg Ile
                                                       1

TGC ACT GGG ATA ACA TCG TCA AAC TCC CCC CAT GTG GTC CAA ACT GCT             102
Cys Thr Gly Ile Thr Ser Ser Asn Ser Pro His Val Val Gln Thr Ala
         5                  10                  15

ACT CAA GGG GAA GTC AAT GTG ACT GGT GTG ATA CCA CTG ACA ACA ACA             150
Thr Gln Gly Glu Val Asn Val Thr Gly Val Ile Pro Leu Thr Thr Thr
 20                  25                  30                  35

CCC ACC AAA TCT CAT TTT GCA AAT CTC AAA GGG ACA AAA ACT AGA GGG             198
Pro Thr Lys Ser His Phe Ala Asn Leu Lys Gly Thr Lys Thr Arg Gly
                 40                  45                  50

AAA CTA TGC CCA AAA TGT CTC AAC TGC ACA GAT CTG GAC GTG GCC TTG             246
Lys Leu Cys Pro Lys Cys Leu Asn Cys Thr Asp Leu Asp Val Ala Leu
             55                  60                  65

GCG AGA CCA AAG TGC ACG GGG ACC ATA CCT TCG GCA AAA GCT TCA ATA             294
Ala Arg Pro Lys Cys Thr Gly Thr Ile Pro Ser Ala Lys Ala Ser Ile
         70                  75                  80

CTT CAC GAA GTC AAA CCT GTT ACA TCT GGG TGC TTT CCT ATA ATG CAC             342
Leu His Glu Val Lys Pro Val Thr Ser Gly Cys Phe Pro Ile Met His
     85                  90                  95

GAC AGA ACA AAA ATT AGA CAG CTA CCC AAT CTT CTC AGA GGA TAC GAA             390
Asp Arg Thr Lys Ile Arg Gln Leu Pro Asn Leu Leu Arg Gly Tyr Glu
100                 105                 110                 115

CAT ATC AGG TTA TCA ACC CAT AAC GTT ATC AAC GCA GAA ACG GCA CCA             438
His Ile Arg Leu Ser Thr His Asn Val Ile Asn Ala Glu Thr Ala Pro
                120                 125                 130
```

-continued

| | | | | | | | | | | | | | | | | |
|---|---|---|---|---|---|---|---|---|---|---|---|---|---|---|---|---|
| GGA | GGA | CCC | TAC | AAA | ATT | GGA | ACC | TCA | GGG | TCT | TGC | CCT | AAC | GTT | ACC | 486 |
| Gly | Gly | Pro | Tyr | Lys | Ile | Gly | Thr | Ser | Gly | Ser | Cys | Pro | Asn | Val | Thr | |
| | | 135 | | | | | 140 | | | | | 145 | | | | |
| AAT | GGA | AAC | GGA | TTC | TTT | GCA | ACA | ATG | GCT | TGG | GCT | GTC | CCA | AAA | AAC | 534 |
| Asn | Gly | Asn | Gly | Phe | Phe | Ala | Thr | Met | Ala | Trp | Ala | Val | Pro | Lys | Asn | |
| | 150 | | | | | 155 | | | | 160 | | | | | | |
| GAC | AAC | AAC | AAA | ACA | GCA | ACA | AAT | CCA | TTA | ACA | GTA | GAA | ATA | CCA | TAC | 582 |
| Asp | Asn | Asn | Lys | Thr | Ala | Thr | Asn | Pro | Leu | Thr | Val | Glu | Ile | Pro | Tyr | |
| | 165 | | | | | 170 | | | | 175 | | | | | | |
| ATT | TGT | ACA | GAA | GGA | GAA | GAC | CAA | ATT | ACT | GTT | TGG | GGG | TTC | CAC | TCT | 630 |
| Ile | Cys | Thr | Glu | Gly | Glu | Asp | Gln | Ile | Thr | Val | Trp | Gly | Phe | His | Ser | |
| 180 | | | | | 185 | | | | | 190 | | | | | 195 | |
| GAT | AAC | GAA | GCC | CAA | ATG | GTA | AAA | CTC | TAT | GGA | GAC | TCA | AAG | CCT | CAG | 678 |
| Asp | Asn | Glu | Ala | Gln | Met | Val | Lys | Leu | Tyr | Gly | Asp | Ser | Lys | Pro | Gln | |
| | | | | 200 | | | | | 205 | | | | | 210 | | |
| AAG | TTC | ACC | TCA | TCT | GCC | AAC | GGA | GTG | ACC | ACA | CAT | TAC | GTT | TCA | CAG | 726 |
| Lys | Phe | Thr | Ser | Ser | Ala | Asn | Gly | Val | Thr | Thr | His | Tyr | Val | Ser | Gln | |
| | | | 215 | | | | | 220 | | | | | 225 | | | |
| ATT | GGT | GGC | TTC | CCA | AAT | CAA | GCA | GAA | GAC | GGA | GGG | CTA | CCA | CAA | AGC | 774 |
| Ile | Gly | Gly | Phe | Pro | Asn | Gln | Ala | Glu | Asp | Gly | Gly | Leu | Pro | Gln | Ser | |
| | | 230 | | | | | 235 | | | | | 240 | | | | |
| GGT | AGA | ATT | GTT | GTT | GAT | TAC | ATG | GTG | CAA | AAA | TCT | GGA | AAA | ACA | GGA | 822 |
| Gly | Arg | Ile | Val | Val | Asp | Tyr | Met | Val | Gln | Lys | Ser | Gly | Lys | Thr | Gly | |
| | 245 | | | | | 250 | | | | | 255 | | | | | |
| ACA | ATT | ACC | TAC | CAA | AGA | GGT | ATT | TTA | TTG | CCT | CAA | AAA | GTG | TGG | TGC | 870 |
| Thr | Ile | Thr | Tyr | Gln | Arg | Gly | Ile | Leu | Leu | Pro | Gln | Lys | Val | Trp | Cys | |
| 260 | | | | | 265 | | | | | 270 | | | | | 275 | |
| GCA | AGT | GGC | AGG | AGC | AAG | GTA | ATA | AAA | GGG | TCC | TTG | CCT | TTA | ATT | GGC | 918 |
| Ala | Ser | Gly | Arg | Ser | Lys | Val | Ile | Lys | Gly | Ser | Leu | Pro | Leu | Ile | Gly | |
| | | | | 280 | | | | | 285 | | | | | 290 | | |
| GAA | CGA | GAT | TGC | CTC | CAC | GAA | AAA | TAC | GGT | GGA | TTA | AAC | AAA | AGC | AAA | 966 |
| Glu | Arg | Asp | Cys | Leu | His | Glu | Lys | Tyr | Gly | Gly | Leu | Asn | Lys | Ser | Lys | |
| | | | 295 | | | | | 300 | | | | | 305 | | | |
| CCT | TAC | TAC | ACA | GGG | GAA | CAT | GCA | AAA | GCC | ATA | GGA | AAT | TGC | CCA | ATA | 1014 |
| Pro | Tyr | Tyr | Thr | Gly | Glu | His | Ala | Lys | Ala | Ile | Gly | Asn | Cys | Pro | Ile | |
| | | 310 | | | | | 315 | | | | | 320 | | | | |
| TGG | GTG | AAA | ACA | CCC | TTG | AAG | CTG | GCC | AAT | GGA | ACC | AAA | TAT | AGA | CCT | 1062 |
| Trp | Val | Lys | Thr | Pro | Leu | Lys | Leu | Ala | Asn | Gly | Thr | Lys | Tyr | Arg | Pro | |
| | 325 | | | | | 330 | | | | | 335 | | | | | |
| CCT | GCA | AAA | CTA | TTA | AAG | GAA | AGG | | | | | | | | | 1086 |
| Pro | Ala | Lys | Leu | Leu | Lys | Glu | Arg | | | | | | | | | |
| 340 | | | | | 345 | | | | | | | | | | | |

( 2 ) INFORMATION FOR SEQ ID NO:2:

( i ) SEQUENCE CHARACTERISTICS:
        ( A ) LENGTH: 347 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Asp | Arg | Ile | Cys | Thr | Gly | Ile | Thr | Ser | Ser | Asn | Ser | Pro | His | Val | Val |
| 1 | | | | 5 | | | | | 10 | | | | | 15 | |
| Gln | Thr | Ala | Thr | Gln | Gly | Glu | Val | Asn | Val | Thr | Gly | Val | Ile | Pro | Leu |
| | | | 20 | | | | | 25 | | | | | 30 | | |
| Thr | Thr | Thr | Pro | Thr | Lys | Ser | His | Phe | Ala | Asn | Leu | Lys | Gly | Thr | Lys |
| | | 35 | | | | | 40 | | | | | 45 | | | |
| Thr | Arg | Gly | Lys | Leu | Cys | Pro | Lys | Cys | Leu | Asn | Cys | Thr | Asp | Leu | Asp |
| | | 50 | | | | 55 | | | | | 60 | | | | |
| Val | Ala | Leu | Ala | Arg | Pro | Lys | Cys | Thr | Gly | Thr | Ile | Pro | Ser | Ala | Lys |
| 65 | | | | 70 | | | | 75 | | | | | | | 80 |

| | | | | | | | | | | | | | | |
|---|---|---|---|---|---|---|---|---|---|---|---|---|---|---|
|Ala|Ser|Ile|Leu|His|Glu|Val|Lys|Pro|Val|Thr|Ser|Gly|Cys|Phe|Pro|
| | | | |85| | | |90| | | | |95| |
|Ile|Met|His|Asp|Arg|Thr|Lys|Ile|Arg|Gln|Leu|Pro|Asn|Leu|Leu|Arg|
| | | |100| | | |105| | | | |110| | |
|Gly|Tyr|Glu|His|Ile|Arg|Leu|Ser|Thr|His|Asn|Val|Ile|Asn|Ala|Glu|
| | |115| | | | |120| | | |125| | | |
|Thr|Ala|Pro|Gly|Gly|Pro|Tyr|Lys|Ile|Gly|Thr|Ser|Gly|Ser|Cys|Pro|
| |130| | | |135| | | | |140| | | | |
|Asn|Val|Thr|Asn|Gly|Asn|Gly|Phe|Phe|Ala|Thr|Met|Ala|Trp|Ala|Val|
|145| | | | |150| | | |155| | | | |160|
|Pro|Lys|Asn|Asp|Asn|Asn|Lys|Thr|Ala|Thr|Asn|Pro|Leu|Thr|Val|Glu|
| | | | |165| | | |170| | | | |175| |
|Ile|Pro|Tyr|Ile|Cys|Thr|Glu|Gly|Glu|Asp|Gln|Ile|Thr|Val|Trp|Gly|
| | | |180| | | | |185| | | | |190| |
|Phe|His|Ser|Asp|Asn|Glu|Ala|Gln|Met|Val|Lys|Leu|Tyr|Gly|Asp|Ser|
| | |195| | | | |200| | | | |205| | |
|Lys|Pro|Gln|Lys|Phe|Thr|Ser|Ser|Ala|Asn|Gly|Val|Thr|Thr|His|Tyr|
| |210| | | | |215| | | | |220| | | |
|Val|Ser|Gln|Ile|Gly|Gly|Phe|Pro|Asn|Gln|Ala|Glu|Asp|Gly|Gly|Leu|
|225| | | | |230| | | |235| | | | |240|
|Pro|Gln|Ser|Gly|Arg|Ile|Val|Val|Asp|Tyr|Met|Val|Gln|Lys|Ser|Gly|
| | | | |245| | | |250| | | | |255| |
|Lys|Thr|Gly|Thr|Ile|Thr|Tyr|Gln|Arg|Gly|Ile|Leu|Leu|Pro|Gln|Lys|
| | | |260| | | |265| | | | |270| | |
|Val|Trp|Cys|Ala|Ser|Gly|Arg|Ser|Lys|Val|Ile|Lys|Gly|Ser|Leu|Pro|
| | |275| | | | |280| | | | |285| | |
|Leu|Ile|Gly|Glu|Arg|Asp|Cys|Leu|His|Glu|Lys|Tyr|Gly|Gly|Leu|Asn|
| |290| | | | |295| | | | |300| | | |
|Lys|Ser|Lys|Pro|Tyr|Tyr|Thr|Gly|Glu|His|Ala|Lys|Ala|Ile|Gly|Asn|
|305| | | | |310| | | |315| | | | |320|
|Cys|Pro|Ile|Trp|Val|Lys|Thr|Pro|Leu|Lys|Leu|Ala|Asn|Gly|Thr|Lys|
| | | | |325| | | |330| | | | |335| |
|Tyr|Arg|Pro|Pro|Ala|Lys|Leu|Leu|Lys|Glu|Arg| | | | | |
| | | |340| | | | |345| | | | | | | |

( 2 ) INFORMATION FOR SEQ ID NO:3:

( i ) SEQUENCE CHARACTERISTICS:
        ( A ) LENGTH: 1086 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 46..1086
        ( D ) OTHER INFORMATION: /label=IN89

( x i ) SEQUENCE DESCRIPTION: SEQ ID NO:3:

```
ATGAAGGCAA TAATTGTACT ACTCATGGTA GTAACATCCA ATGCA GAT CGA ATC           54
                                                 Asp Arg Ile
                                                   1

TGC ACT GGG ATA ACA TCG TCA AAC TCA CCC CAT GTG GTC AAA ACT GCT        102
Cys Thr Gly Ile Thr Ser Ser Asn Ser Pro His Val Val Lys Thr Ala
      5               10                  15

ACT CAA GGG GAA GTC AAT GTG ACT GGT GTG ATA CCA CTG ACA ACA ACA        150
Thr Gln Gly Glu Val Asn Val Thr Gly Val Ile Pro Leu Thr Thr Thr
 20              25                  30                  35
```

| | | | | | | | | | | | | | | | | |
|---|---|---|---|---|---|---|---|---|---|---|---|---|---|---|---|---|
| CCC | ACC | AAA | TCT | CAT | TTT | GCA | AAT | CTC | AAA | GGA | ACA | AAA | ACC | AGA | GGG | 198 |
| Pro | Thr | Lys | Ser | His 40 | Phe | Ala | Asn | Leu | Lys 45 | Gly | Thr | Lys | Thr | Arg 50 | Gly | |
| AAA | CTA | TGC | CCA | AAG | TGT | CTC | AAC | TGC | ACA | GAT | CTG | GAC | GTG | GCC | TTG | 246 |
| Lys | Leu | Cys | Pro 55 | Lys | Cys | Leu | Asn | Cys 60 | Thr | Asp | Leu | Asp | Val 65 | Ala | Leu | |
| GCG | AGA | CCA | AAG | TGC | ACG | GGG | ACC | ATA | CCT | TCG | GCA | AAA | GCT | TCA | ATA | 294 |
| Ala | Arg | Pro 70 | Lys | Cys | Thr | Gly | Thr | Ile 75 | Pro | Ser | Ala | Lys | Ala 80 | Ser | Ile | |
| CTC | CAC | GAA | GTC | AAA | CCT | GTT | ACA | TTT | GGG | TGC | TTT | CCT | ATA | ATG | CAC | 342 |
| Leu | His 85 | Glu | Val | Lys | Pro | Val 90 | Thr | Phe | Gly | Cys | Phe 95 | Pro | Ile | Met | His | |
| GAC | AGA | ACA | AAA | ATT | AGA | CAG | CTA | CCC | AAT | CTT | CTC | AGA | GGA | TAC | GAA | 390 |
| Asp 100 | Arg | Thr | Lys | Ile | Arg 105 | Gln | Leu | Pro | Asn | Leu 110 | Leu | Arg | Gly | Tyr | Glu 115 | |
| CAT | ATC | AGG | TTA | TCA | ACC | CAT | AAC | GTT | ATC | AAC | GCA | GAA | ACG | GCA | CCA | 438 |
| His | Ile | Arg | Leu | Ser 120 | Thr | His | Asn | Val | Ile 125 | Asn | Ala | Glu | Thr | Ala 130 | Pro | |
| GGA | GGA | CCC | TAC | AAA | ATT | GGA | ACC | TCA | AGG | TCT | TGC | CCT | AAC | GTT | ACC | 486 |
| Gly | Gly | Pro | Tyr 135 | Lys | Ile | Gly | Thr | Ser 140 | Arg | Ser | Cys | Pro | Asn 145 | Val | Thr | |
| AAT | GGA | AAC | GGA | TTC | TTC | GCA | ACA | ATG | GCT | TGG | GCT | GTC | CCA | AAA | AAC | 534 |
| Asn | Gly | Asn 150 | Gly | Phe | Phe | Ala | Thr 155 | Met | Ala | Trp | Ala | Val 160 | Pro | Lys | Asn | |
| GAC | AAC | AAC | AAA | ACA | GCA | ACA | AAT | CCA | TTA | ACA | GTA | GAA | GTA | CCA | TAC | 582 |
| Asp | Asn 165 | Asn | Lys | Thr | Ala | Thr 170 | Asn | Pro | Leu | Thr | Val 175 | Glu | Val | Pro | Tyr | |
| ATT | TGT | ACA | GAA | GGA | GAA | GAC | CAA | ATT | ACT | GTT | TGG | GGG | TTT | CAC | TCT | 630 |
| Ile 180 | Cys | Thr | Glu | Gly | Glu 185 | Asp | Gln | Ile | Thr | Val 190 | Trp | Gly | Phe | His | Ser 195 | |
| GAT | AAC | GAA | ACC | CAA | ATG | GTA | AAA | CTC | TAT | GGA | GAC | TCA | AAG | CCT | CAG | 678 |
| Asp | Asn | Glu | Thr | Gln 200 | Met | Val | Lys | Leu | Tyr 205 | Gly | Asp | Ser | Lys | Pro 210 | Gln | |
| AAG | TTC | ACC | TCA | TCT | GCC | AAC | GGA | GTG | ACC | ACA | CAT | TAC | GTT | TCA | CAG | 726 |
| Lys | Phe | Thr | Ser 215 | Ser | Ala | Asn | Gly | Val 220 | Thr | Thr | His | Tyr | Val 225 | Ser | Gln | |
| ATT | GGT | GGC | TTC | CCA | AAT | CAA | GCA | GAA | GAC | GGA | GGG | CTA | CCA | CAA | AGC | 774 |
| Ile | Gly | Gly 230 | Phe | Pro | Asn | Gln | Ala 235 | Glu | Asp | Gly | Gly | Leu 240 | Pro | Gln | Ser | |
| GGT | AGA | ATT | GTT | GTT | GAT | TAC | ATG | GTG | CAA | AAA | TCT | GGA | AAA | ACA | GGA | 822 |
| Gly | Arg 245 | Ile | Val | Val | Asp | Tyr 250 | Met | Val | Gln | Lys | Ser 255 | Gly | Lys | Thr | Gly | |
| ACA | ATT | ACC | TAC | CAA | AGA | GGT | ATT | TTA | TTG | CCT | CAA | AAA | GTG | TGG | TGC | 870 |
| Thr 260 | Ile | Thr | Tyr | Gln | Arg 265 | Gly | Ile | Leu | Leu | Pro 270 | Gln | Lys | Val | Trp | Cys 275 | |
| GCA | AGT | GGC | AGG | AGC | AAG | GTA | ATA | AAA | GGG | TCC | TTG | CCT | TTA | ATT | GGC | 918 |
| Ala | Ser | Gly | Arg | Ser 280 | Lys | Val | Ile | Lys | Gly 285 | Ser | Leu | Pro | Leu | Ile 290 | Gly | |
| GAA | GCA | GAT | TGC | CTC | CAC | GAA | AAA | TAC | GGT | GGA | TTA | AAC | AAA | AGC | AAA | 966 |
| Glu | Ala | Asp | Cys 295 | Leu | His | Glu | Lys | Tyr 300 | Gly | Gly | Leu | Asn | Lys 305 | Ser | Lys | |
| CCT | TAC | TAC | ACA | GGG | GAA | CAT | GCA | AAA | GCC | ATA | GGA | AAT | TGC | CCA | ATA | 1014 |
| Pro | Tyr | Tyr 310 | Thr | Gly | Glu | His | Ala 315 | Lys | Ala | Ile | Gly | Asn 320 | Cys | Pro | Ile | |
| TGG | GTG | AAA | ACA | CCC | TTG | AAG | CTG | GCC | AAT | GGA | ACC | AAA | TAT | AGA | CCT | 1062 |
| Trp | Val | Lys | Thr 325 | Pro | Leu | Lys | Leu | Ala 330 | Asn | Gly | Thr | Lys | Tyr 335 | Arg | Pro | |
| CCT | GCA | AAA | CTA | TTA | AAG | GAA | AGG | | | | | | | | | 1086 |
| Pro | Ala | Lys 340 | Leu | Leu | Lys | Glu | Arg 345 | | | | | | | | | |

( 2 ) INFORMATION FOR SEQ ID NO:4:

( i ) SEQUENCE CHARACTERISTICS:
      ( A ) LENGTH: 347 amino acids
      ( B ) TYPE: amino acid
      ( D ) TOPOLOGY: linear ( i i ) MOLECULE TYPE: protein ( x i ) SEQUENCE DESCRIPTION: SEQ ID NO:4:

```
Asp Arg Ile Cys Thr Gly Ile Thr Ser Ser Asn Ser Pro His Val Val
 1               5                  10                  15
Lys Thr Ala Thr Gln Gly Glu Val Asn Val Thr Gly Val Ile Pro Leu
             20                  25                  30
Thr Thr Thr Pro Thr Lys Ser His Phe Ala Asn Leu Lys Gly Thr Lys
         35                  40                  45
Thr Arg Gly Lys Leu Cys Pro Lys Cys Leu Asn Cys Thr Asp Leu Asp
     50                  55                  60
Val Ala Leu Ala Arg Pro Lys Cys Thr Gly Thr Ile Pro Ser Ala Lys
 65                  70                  75                  80
Ala Ser Ile Leu His Glu Val Lys Pro Val Thr Phe Gly Cys Phe Pro
                 85                  90                  95
Ile Met His Asp Arg Thr Lys Ile Arg Gln Leu Pro Asn Leu Leu Arg
             100                 105                 110
Gly Tyr Glu His Ile Arg Leu Ser Thr His Asn Val Ile Asn Ala Glu
         115                 120                 125
Thr Ala Pro Gly Gly Pro Tyr Lys Ile Gly Thr Ser Arg Ser Cys Pro
     130                 135                 140
Asn Val Thr Asn Gly Asn Gly Phe Phe Ala Thr Met Ala Trp Ala Val
145                 150                 155                 160
Pro Lys Asn Asp Asn Asn Lys Thr Ala Thr Asn Pro Leu Thr Val Glu
                165                 170                 175
Val Pro Tyr Ile Cys Thr Glu Gly Glu Asp Gln Ile Thr Val Trp Gly
            180                 185                 190
Phe His Ser Asp Asn Glu Thr Gln Met Val Lys Leu Tyr Gly Asp Ser
        195                 200                 205
Lys Pro Gln Lys Phe Thr Ser Ser Ala Asn Gly Val Thr Thr His Tyr
    210                 215                 220
Val Ser Gln Ile Gly Gly Phe Pro Asn Gln Ala Glu Asp Gly Gly Leu
225                 230                 235                 240
Pro Gln Ser Gly Arg Ile Val Val Asp Tyr Met Val Gln Lys Ser Gly
                245                 250                 255
Lys Thr Gly Thr Ile Thr Tyr Gln Arg Gly Ile Leu Leu Pro Gln Lys
            260                 265                 270
Val Trp Cys Ala Ser Gly Arg Ser Lys Val Ile Lys Gly Ser Leu Pro
        275                 280                 285
Leu Ile Gly Glu Ala Asp Cys Leu His Glu Lys Tyr Gly Gly Leu Asn
    290                 295                 300
Lys Ser Lys Pro Tyr Tyr Thr Gly Glu His Ala Lys Ala Ile Gly Asn
305                 310                 315                 320
Cys Pro Ile Trp Val Lys Thr Pro Leu Lys Leu Ala Asn Gly Thr Lys
                325                 330                 335
Tyr Arg Pro Pro Ala Lys Leu Leu Lys Glu Arg
            340                 345
```

( 2 ) INFORMATION FOR SEQ ID NO:5:

( i ) SEQUENCE CHARACTERISTICS:
      ( A ) LENGTH: 1086 base pairs ( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 46..1086
( D ) OTHER INFORMATION: /label=VI19

( x i ) SEQUENCE DESCRIPTION: SEQ ID NO:5:

| | | | | | | | | | | | | | | | | |
|---|---|---|---|---|---|---|---|---|---|---|---|---|---|---|---|---|
| ATGAAGGCAA | TAATTGTACT | ACTCATGGTA | GTAACATCCA | ATGCA | GAT | CGA | ATC | | | | | | | | | 54 |
| | | | | | Asp | Arg | Ile | | | | | | | | | |
| | | | | | | 1 | | | | | | | | | | |

| TGC | ACT | GGG | ATA | ACA | TCG | TCA | AAC | TCA | CCC | CAT | GTG | GTC | AAA | ACT | GCT | 102 |
|---|---|---|---|---|---|---|---|---|---|---|---|---|---|---|---|---|
| Cys | Thr | Gly | Ile | Thr | Ser | Ser | Asn | Ser | Pro | His | Val | Val | Lys | Thr | Ala | |
| | 5 | | | | | 10 | | | | | 15 | | | | | |
| ACT | CAA | GGG | GAA | GTC | AAT | GTG | ACT | GGT | GTG | ATA | CCA | CTG | ACA | ACA | ACA | 150 |
| Thr | Gln | Gly | Glu | Val | Asn | Val | Thr | Gly | Val | Ile | Pro | Leu | Thr | Thr | Thr | |
| 20 | | | | | 25 | | | | | 30 | | | | | 35 | |
| CCC | ACC | AAA | TCT | CAT | TTT | GCA | AAT | CTC | AAA | GGA | ACA | AAA | ACC | AGA | GGG | 198 |
| Pro | Thr | Lys | Ser | His | Phe | Ala | Asn | Leu | Lys | Gly | Thr | Lys | Thr | Arg | Gly | |
| | | | | 40 | | | | | 45 | | | | | 50 | | |
| AAA | CTA | TGC | CCA | AAG | TGT | CTC | AAC | TGC | ACA | GAT | CTG | GAC | GTG | GCC | TTG | 246 |
| Lys | Leu | Cys | Pro | Lys | Cys | Leu | Asn | Cys | Thr | Asp | Leu | Asp | Val | Ala | Leu | |
| | | | 55 | | | | | 60 | | | | | 65 | | | |
| GCG | AGG | CCA | AAG | TGC | ACG | GGG | ACC | ATA | CCT | TCG | GCA | AAA | GCT | TCA | ATA | 294 |
| Ala | Arg | Pro | Lys | Cys | Thr | Gly | Thr | Ile | Pro | Ser | Ala | Lys | Ala | Ser | Ile | |
| | | 70 | | | | | 75 | | | | | 80 | | | | |
| CTC | CAC | GAA | GTC | AAA | CCT | GTT | ACA | TTT | GGG | TGC | TTT | CCT | ATA | ATG | CAC | 342 |
| Leu | His | Glu | Val | Lys | Pro | Val | Thr | Phe | Gly | Cys | Phe | Pro | Ile | Met | His | |
| | 85 | | | | | 90 | | | | | 95 | | | | | |
| GAC | AGA | ACA | AAA | ATT | AGA | CAG | CTA | CCC | AAT | CTT | CTC | AGA | GGA | TAC | GAA | 390 |
| Asp | Arg | Thr | Lys | Ile | Arg | Gln | Leu | Pro | Asn | Leu | Leu | Arg | Gly | Tyr | Glu | |
| 100 | | | | | 105 | | | | | 110 | | | | | 115 | |
| CAT | ATC | AGG | TTA | TCA | ACC | CAT | AAC | GTT | ATC | AAC | GCA | GAA | AAG | GCA | CCA | 438 |
| His | Ile | Arg | Leu | Ser | Thr | His | Asn | Val | Ile | Asn | Ala | Glu | Lys | Ala | Pro | |
| | | | | 120 | | | | | 125 | | | | | 130 | | |
| GGA | GGA | CCC | TAC | AAA | ATT | GGA | ACC | TCA | GGG | TCT | TGC | CCT | AAC | GTT | ACC | 486 |
| Gly | Gly | Pro | Tyr | Lys | Ile | Gly | Thr | Ser | Gly | Ser | Cys | Pro | Asn | Val | Thr | |
| | | | 135 | | | | | 140 | | | | | 145 | | | |
| AAT | GGA | AAC | GGA | TTC | TTC | GCA | ACA | ATG | GCT | TGG | GCT | GTC | CCA | AAA | AAC | 534 |
| Asn | Gly | Asn | Gly | Phe | Phe | Ala | Thr | Met | Ala | Trp | Ala | Val | Pro | Lys | Asn | |
| | | 150 | | | | | 155 | | | | | 160 | | | | |
| GAC | AAC | AAC | AAA | ACA | GCA | ACA | AAT | TCA | TTA | ACA | GTA | GAA | GTA | CCA | TAC | 582 |
| Asp | Asn | Asn | Lys | Thr | Ala | Thr | Asn | Ser | Leu | Thr | Val | Glu | Val | Pro | Tyr | |
| | 165 | | | | | 170 | | | | | 175 | | | | | |
| ATT | TGT | ACA | GAA | GGA | GAA | GAC | CAA | ATT | ACC | GTT | TGG | GGG | TTC | CAC | TCT | 630 |
| Ile | Cys | Thr | Glu | Gly | Glu | Asp | Gln | Ile | Thr | Val | Trp | Gly | Phe | His | Ser | |
| 180 | | | | | 185 | | | | | 190 | | | | | 195 | |
| GAT | AAC | GAA | ATC | CAA | ATG | GTA | AAA | CTC | TAT | GGA | GAC | TCA | AAG | CCT | CAG | 678 |
| Asp | Asn | Glu | Ile | Gln | Met | Val | Lys | Leu | Tyr | Gly | Asp | Ser | Lys | Pro | Gln | |
| | | | | 200 | | | | | 205 | | | | | 210 | | |
| AAG | TTC | ACC | TCA | TCT | GCC | AAT | GGA | GTA | ACC | ACA | CAT | TAC | GTT | TCA | CAG | 726 |
| Lys | Phe | Thr | Ser | Ser | Ala | Asn | Gly | Val | Thr | Thr | His | Tyr | Val | Ser | Gln | |
| | | | 215 | | | | | 220 | | | | | 225 | | | |
| ATT | GGT | GGC | TTC | CCA | AAT | CAA | GCA | GAA | GAC | GGA | GGG | CTA | CCA | CAA | AGC | 774 |
| Ile | Gly | Gly | Phe | Pro | Asn | Gln | Ala | Glu | Asp | Gly | Gly | Leu | Pro | Gln | Ser | |
| | | 230 | | | | | 235 | | | | | 240 | | | | |
| GGT | AGA | ATT | GTT | GTT | GAT | TAC | ATG | GTG | CAA | AAA | TCT | GGA | AAA | ACA | GGA | 822 |
| Gly | Arg | Ile | Val | Val | Asp | Tyr | Met | Val | Gln | Lys | Ser | Gly | Lys | Thr | Gly | |
| | 245 | | | | | 250 | | | | | 255 | | | | | |

| | | | | | | | | | | | | | | | | |
|---|---|---|---|---|---|---|---|---|---|---|---|---|---|---|---|---|
| ACA | ATT | ACC | TAC | CAA | AGA | GGT | ATT | TTA | TTG | CCT | CAA | AAA | GTG | TGG | TGC | 870 |
| Thr | Ile | Thr | Tyr | Gln | Arg | Gly | Ile | Leu | Leu | Pro | Gln | Lys | Val | Trp | Cys | |
| 260 | | | | 265 | | | | | 270 | | | | | 275 | | |
| GCA | AGT | GGC | AGG | AGC | AAG | GTA | ATA | AAA | GGG | TCC | TTG | CCT | TTA | ATT | GGC | 918 |
| Ala | Ser | Gly | Arg | Ser | Lys | Val | Ile | Lys | Gly | Ser | Leu | Pro | Leu | Ile | Gly | |
| | | | | 280 | | | | 285 | | | | | 290 | | | |
| GAA | GCA | GAT | TGC | CTC | CAC | GAA | AAA | TAC | GGT | GGA | TTA | AAC | AAA | AGC | AAG | 966 |
| Glu | Ala | Asp | Cys | Leu | His | Glu | Lys | Tyr | Gly | Gly | Leu | Asn | Lys | Ser | Lys | |
| | | | 295 | | | | 300 | | | | | 305 | | | | |
| CCT | TAC | TAC | ACA | GGG | GAA | CAT | GCA | AAA | GCC | ATA | GGA | AAT | TGC | CCA | ATA | 1014 |
| Pro | Tyr | Tyr | Thr | Gly | Glu | His | Ala | Lys | Ala | Ile | Gly | Asn | Cys | Pro | Ile | |
| | | 310 | | | | 315 | | | | 320 | | | | | | |
| TGG | GTG | AAA | ACA | CCC | TTG | AAG | CTG | GCC | AAT | GGA | ACC | AAA | TAT | AGA | CCT | 1062 |
| Trp | Val | Lys | Thr | Pro | Leu | Lys | Leu | Ala | Asn | Gly | Thr | Lys | Tyr | Arg | Pro | |
| | 325 | | | | 330 | | | | | 335 | | | | | | |
| CCT | GCA | AAA | CTA | TTA | AAG | GAA | AGG | | | | | | | | | 1086 |
| Pro | Ala | Lys | Leu | Leu | Lys | Glu | Arg | | | | | | | | | |
| 340 | | | | | 345 | | | | | | | | | | | |

(2) INFORMATION FOR SEQ ID NO:6:

(i) SEQUENCE CHARACTERISTICS:
        (A) LENGTH: 347 amino acids
        (B) TYPE: amino acid
        (D) TOPOLOGY: linear (ii) MOLECULE TYPE: protein (xi) SEQUENCE DESCRIPTION: SEQ ID NO:6:

| | | | | | | | | | | | | | | |
|---|---|---|---|---|---|---|---|---|---|---|---|---|---|---|
| Asp | Arg | Ile | Cys | Thr | Gly | Ile | Thr | Ser | Ser | Asn | Ser | Pro | His | Val | Val |
| 1 | | | | 5 | | | | | 10 | | | | | 15 | |
| Lys | Thr | Ala | Thr | Gln | Gly | Glu | Val | Asn | Val | Thr | Gly | Val | Ile | Pro | Leu |
| | | | 20 | | | | | 25 | | | | | 30 | | |
| Thr | Thr | Thr | Pro | Thr | Lys | Ser | His | Phe | Ala | Asn | Leu | Lys | Gly | Thr | Lys |
| | | 35 | | | | | 40 | | | | | 45 | | | |
| Thr | Arg | Gly | Lys | Leu | Cys | Pro | Lys | Cys | Leu | Asn | Cys | Thr | Asp | Leu | Asp |
| | 50 | | | | | 55 | | | | | 60 | | | | |
| Val | Ala | Leu | Ala | Arg | Pro | Lys | Cys | Thr | Gly | Thr | Ile | Pro | Ser | Ala | Lys |
| 65 | | | | | 70 | | | | | 75 | | | | | 80 |
| Ala | Ser | Ile | Leu | His | Glu | Val | Lys | Pro | Val | Thr | Phe | Gly | Cys | Phe | Pro |
| | | | | 85 | | | | | 90 | | | | | 95 | |
| Ile | Met | His | Asp | Arg | Thr | Lys | Ile | Arg | Gln | Leu | Pro | Asn | Leu | Leu | Arg |
| | | | | 100 | | | | | 105 | | | | | 110 | |
| Gly | Tyr | Glu | His | Ile | Arg | Leu | Ser | Thr | His | Asn | Val | Ile | Asn | Ala | Glu |
| | | | 115 | | | | | 120 | | | | | 125 | | |
| Lys | Ala | Pro | Gly | Gly | Pro | Tyr | Lys | Ile | Gly | Thr | Ser | Gly | Ser | Cys | Pro |
| | 130 | | | | | 135 | | | | | 140 | | | | |
| Asn | Val | Thr | Asn | Gly | Asn | Gly | Phe | Phe | Ala | Thr | Met | Ala | Trp | Ala | Val |
| 145 | | | | | 150 | | | | | 155 | | | | | 160 |
| Pro | Lys | Asn | Asp | Asn | Asn | Lys | Thr | Ala | Thr | Asn | Ser | Leu | Thr | Val | Glu |
| | | | | 165 | | | | | 170 | | | | | 175 | |
| Val | Pro | Tyr | Ile | Cys | Thr | Glu | Gly | Glu | Asp | Gln | Ile | Thr | Val | Trp | Gly |
| | | | 180 | | | | | 185 | | | | | 190 | | |
| Phe | His | Ser | Asp | Asn | Glu | Ile | Gln | Met | Val | Lys | Leu | Tyr | Gly | Asp | Ser |
| | | 195 | | | | | 200 | | | | | 205 | | | |
| Lys | Pro | Gln | Lys | Phe | Thr | Ser | Ser | Ala | Asn | Gly | Val | Thr | Thr | His | Tyr |
| | 210 | | | | | 215 | | | | | 220 | | | | |
| Val | Ser | Gln | Ile | Gly | Gly | Phe | Pro | Asn | Gln | Ala | Glu | Asp | Gly | Gly | Leu |
| 225 | | | | | 230 | | | | | 235 | | | | | 240 |
| Pro | Gln | Ser | Gly | Arg | Ile | Val | Val | Asp | Tyr | Met | Val | Gln | Lys | Ser | Gly |

```
                    245                           250                          255
Lys  Thr  Gly  Thr  Ile  Thr  Tyr  Gln  Arg  Gly  Ile  Leu  Leu  Pro  Gln  Lys
               260                      265                      270

Val  Trp  Cys  Ala  Ser  Gly  Arg  Ser  Lys  Val  Ile  Lys  Gly  Ser  Leu  Pro
          275                      280                      285

Leu  Ile  Gly  Glu  Ala  Asp  Cys  Leu  His  Glu  Lys  Tyr  Gly  Gly  Leu  Asn
          290                      295                 300

Lys  Ser  Lys  Pro  Tyr  Tyr  Thr  Gly  Glu  His  Ala  Lys  Ala  Ile  Gly  Asn
305                      310                      315                      320

Cys  Pro  Ile  Trp  Val  Lys  Thr  Pro  Leu  Lys  Leu  Ala  Asn  Gly  Thr  Lys
                    325                      330                      335

Tyr  Arg  Pro  Pro  Ala  Lys  Leu  Leu  Lys  Glu  Arg
               340                      345
```

( 2 ) INFORMATION FOR SEQ ID NO:7:

( i ) SEQUENCE CHARACTERISTICS:
        ( A ) LENGTH: 1080 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 46..1080
        ( D ) OTHER INFORMATION: /label=GD89

( x i ) SEQUENCE DESCRIPTION: SEQ ID NO:7:

```
ATGAAGGCAA TAATTGTACT ACTCATGGTA GTAACATCCA ACGCA GAT CGA ATC                    54
                                                  Asp Arg Ile
                                                    1

TGC ACT GGG ATA ACA TCT TCA AAC TCA CCT CAT GTG GTC AAA ACA GCT                 102
Cys Thr Gly Ile Thr Ser Ser Asn Ser Pro His Val Val Lys Thr Ala
        5               10              15

ACT CAA GGG GAA GTC AAT GTG ACT GGT GTG ATA CCA CTG ACA ACA ACA                 150
Thr Gln Gly Glu Val Asn Val Thr Gly Val Ile Pro Leu Thr Thr Thr
 20              25              30                      35

CCA ACA AAA TCT CAT TTT GCA AAT CTC AAA GGA ACA AAG ACC AGA GGG                 198
Pro Thr Lys Ser His Phe Ala Asn Leu Lys Gly Thr Lys Thr Arg Gly
             40              45              50

AAA CTA TGC CCA AAC TGT CTC AAC TGC ACA GAT CTG GAT GTG GCC TTG                 246
Lys Leu Cys Pro Asn Cys Leu Asn Cys Thr Asp Leu Asp Val Ala Leu
             55              60              65

GCG AGA CCA ATG TGT ATG GGG ATC ATA CCT TCG GCA AAA GCT TCA ATA                 294
Ala Arg Pro Met Cys Met Gly Ile Ile Pro Ser Ala Lys Ala Ser Ile
         70              75              80

CTC CAC GAA GTC AGA CCT GTT ACA TCC GGG TGC TTT CCT ATA ATG CAC                 342
Leu His Glu Val Arg Pro Val Thr Ser Gly Cys Phe Pro Ile Met His
     85              90              95

GAC AGA ACA AAA ATC AGA CAG CTA CCC AAT CTT CTC AGA GGA TAT GAA                 390
Asp Arg Thr Lys Ile Arg Gln Leu Pro Asn Leu Leu Arg Gly Tyr Glu
100              105             110             115

AAT ATC AGA TTA TCA ACC CAT AAT GTT ATC AAC GCA GAA AGG GCA CCA                 438
Asn Ile Arg Leu Ser Thr His Asn Val Ile Asn Ala Glu Arg Ala Pro
                 120             125             130

GGA GGA CCC TAC AGA CTT GGA ACC TCA GGG TCT TGC CCT AAC GTT ACC                 486
Gly Gly Pro Tyr Arg Leu Gly Thr Ser Gly Ser Cys Pro Asn Val Thr
             135             140             145

AGT AGA AGC GGA TTC TTC GCA ACA ATG GCT TGG GCT GTC CCA AGG GAC                 534
Ser Arg Ser Gly Phe Phe Ala Thr Met Ala Trp Ala Val Pro Arg Asp
         150             155             160
```

| | | | | | | | | | | | | | | | | |
|---|---|---|---|---|---|---|---|---|---|---|---|---|---|---|---|---|
| AAC | AAA | ACA | GCA | ACG | AAT | CCA | CTA | ACA | GTA | GAA | GTA | CCA | TAC | ATT | TGT | 582 |
| Asn | Lys | Thr | Ala | Thr | Asn | Pro | Leu | Thr | Val | Glu | Val | Pro | Tyr | Ile | Cys | |
| | 165 | | | | 170 | | | | | 175 | | | | | | |
| ACA | AAA | GGA | GAA | GAC | CAA | ATT | ACT | GTT | TGG | GGG | TTC | CAT | TCT | GAT | AAA | 630 |
| Thr | Lys | Gly | Glu | Asp | Gln | Ile | Thr | Val | Trp | Gly | Phe | His | Ser | Asp | Lys | |
| 180 | | | | | 185 | | | | | 190 | | | | | 195 | |
| AAA | ACC | CAA | ATG | AAA | AAC | CTC | TAT | GGA | GAC | TCA | AAT | CCT | CAA | AAG | TTC | 678 |
| Lys | Thr | Gln | Met | Lys | Asn | Leu | Tyr | Gly | Asp | Ser | Asn | Pro | Gln | Lys | Phe | |
| | | | | 200 | | | | | 205 | | | | | 210 | | |
| ACC | TCA | TCT | GCC | AAT | GGA | GTA | ACC | ACA | CAT | TAT | GTT | TCT | CAG | ATT | GGT | 726 |
| Thr | Ser | Ser | Ala | Asn | Gly | Val | Thr | Thr | His | Tyr | Val | Ser | Gln | Ile | Gly | |
| | | | 215 | | | | | 220 | | | | | 225 | | | |
| GAC | TTC | CCA | AAT | CAA | ACA | GAA | GAC | GGA | GGG | CTA | CCA | CAA | AGC | GGC | AGA | 774 |
| Asp | Phe | Pro | Asn | Gln | Thr | Glu | Asp | Gly | Gly | Leu | Pro | Gln | Ser | Gly | Arg | |
| | | 230 | | | | | 235 | | | | | 240 | | | | |
| ATT | GTT | GTT | GAT | TAC | ATG | GTG | CAA | AAA | CCT | GGG | AAA | ACA | GGA | ACA | ATT | 822 |
| Ile | Val | Val | Asp | Tyr | Met | Val | Gln | Lys | Pro | Gly | Lys | Thr | Gly | Thr | Ile | |
| | 245 | | | | | 250 | | | | | 255 | | | | | |
| GTC | TAT | CAA | AGA | GGT | GTT | TTG | TTG | CCT | CAA | AAG | GTG | TGG | TGC | GCA | AGT | 870 |
| Val | Tyr | Gln | Arg | Gly | Val | Leu | Leu | Pro | Gln | Lys | Val | Trp | Cys | Ala | Ser | |
| 260 | | | | | 265 | | | | | 270 | | | | | 275 | |
| GGC | AGG | AGC | AAG | GTA | ATA | AAA | GGG | TCC | TTG | CCT | TTA | ATT | GGT | GAA | GCA | 918 |
| Gly | Arg | Ser | Lys | Val | Ile | Lys | Gly | Ser | Leu | Pro | Leu | Ile | Gly | Glu | Ala | |
| | | | | 280 | | | | | 285 | | | | | 290 | | |
| GAT | TGC | CTT | CAC | GCA | AAA | TAC | GGT | GGA | TTA | AAC | AAA | AGC | AAG | CCT | TAC | 966 |
| Asp | Cys | Leu | His | Ala | Lys | Tyr | Gly | Gly | Leu | Asn | Lys | Ser | Lys | Pro | Tyr | |
| | | | 295 | | | | | 300 | | | | | 305 | | | |
| TAC | ACA | GGA | GAA | CAT | GCA | AAA | GCC | ATA | GGA | AAT | TGC | CCA | ATA | TGG | GTG | 1014 |
| Tyr | Thr | Gly | Glu | His | Ala | Lys | Ala | Ile | Gly | Asn | Cys | Pro | Ile | Trp | Val | |
| | | 310 | | | | | 315 | | | | | 320 | | | | |
| AAA | ACA | CCT | TTG | AAG | CTT | GCC | AAT | GGA | ACC | AAA | TAT | AGA | CCT | CCT | GCA | 1062 |
| Lys | Thr | Pro | Leu | Lys | Leu | Ala | Asn | Gly | Thr | Lys | Tyr | Arg | Pro | Pro | Ala | |
| 325 | | | | | 330 | | | | | 335 | | | | | | |
| AAA | CTA | TTA | AAG | GAA | AGG | | | | | | | | | | | 1080 |
| Lys | Leu | Leu | Lys | Glu | Arg | | | | | | | | | | | |
| 340 | | | | 345 | | | | | | | | | | | | |

( 2 ) INFORMATION FOR SEQ ID NO:8:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | | |
|---|---|---|---|---|---|---|---|---|---|---|---|---|---|---|---|
| Asp | Arg | Ile | Cys | Thr | Gly | Ile | Thr | Ser | Ser | Asn | Ser | Pro | His | Val | Val |
| 1 | | | | 5 | | | | | 10 | | | | | 15 | |
| Lys | Thr | Ala | Thr | Gln | Gly | Glu | Val | Asn | Val | Thr | Gly | Val | Ile | Pro | Leu |
| | | | 20 | | | | | 25 | | | | | 30 | | |
| Thr | Thr | Thr | Pro | Thr | Lys | Ser | His | Phe | Ala | Asn | Leu | Lys | Gly | Thr | Lys |
| | | 35 | | | | | 40 | | | | | 45 | | | |
| Thr | Arg | Gly | Lys | Leu | Cys | Pro | Asn | Cys | Leu | Asn | Cys | Thr | Asp | Leu | Asp |
| | 50 | | | | | 55 | | | | | 60 | | | | |
| Val | Ala | Leu | Ala | Arg | Pro | Met | Cys | Met | Gly | Ile | Ile | Pro | Ser | Ala | Lys |
| 65 | | | | | 70 | | | | | 75 | | | | | 80 |
| Ala | Ser | Ile | Leu | His | Glu | Val | Arg | Pro | Val | Thr | Ser | Gly | Cys | Phe | Pro |
| | | | | 85 | | | | | 90 | | | | | 95 | |
| Ile | Met | His | Asp | Arg | Thr | Lys | Ile | Arg | Gln | Leu | Pro | Asn | Leu | Leu | Arg |
| | | | 100 | | | | | 105 | | | | | 110 | | |

| | | | | | | | | | | | | | | |
|---|---|---|---|---|---|---|---|---|---|---|---|---|---|---|
| Gly | Tyr | Glu | Asn | Ile | Arg | Leu | Ser | Thr | His | Asn | Val | Ile | Asn | Ala | Glu |
| | | 115 | | | | | 120 | | | | | 125 | | | |
| Arg | Ala | Pro | Gly | Gly | Pro | Tyr | Arg | Leu | Gly | Thr | Ser | Gly | Ser | Cys | Pro |
| | | 130 | | | | | 135 | | | | | 140 | | | |
| Asn | Val | Thr | Ser | Arg | Ser | Gly | Phe | Phe | Ala | Thr | Met | Ala | Trp | Ala | Val |
| 145 | | | | | 150 | | | | | 155 | | | | | 160 |
| Pro | Arg | Asp | Asn | Lys | Thr | Ala | Thr | Asn | Pro | Leu | Thr | Val | Glu | Val | Pro |
| | | | | 165 | | | | | 170 | | | | | 175 | |
| Tyr | Ile | Cys | Thr | Lys | Gly | Glu | Asp | Gln | Ile | Thr | Val | Trp | Gly | Phe | His |
| | | | 180 | | | | | 185 | | | | | 190 | | |
| Ser | Asp | Lys | Lys | Thr | Gln | Met | Lys | Asn | Leu | Tyr | Gly | Asp | Ser | Asn | Pro |
| | | 195 | | | | | 200 | | | | | 205 | | | |
| Gln | Lys | Phe | Thr | Ser | Ser | Ala | Asn | Gly | Val | Thr | Thr | His | Tyr | Val | Ser |
| | 210 | | | | | 215 | | | | | 220 | | | | |
| Gln | Ile | Gly | Asp | Phe | Pro | Asn | Gln | Thr | Glu | Asp | Gly | Gly | Leu | Pro | Gln |
| 225 | | | | | 230 | | | | | 235 | | | | | 240 |
| Ser | Gly | Arg | Ile | Val | Val | Asp | Tyr | Met | Val | Gln | Lys | Pro | Gly | Lys | Thr |
| | | | | 245 | | | | | 250 | | | | | 255 | |
| Gly | Thr | Ile | Val | Tyr | Gln | Arg | Gly | Val | Leu | Leu | Pro | Gln | Lys | Val | Trp |
| | | | 260 | | | | | 265 | | | | | 270 | | |
| Cys | Ala | Ser | Gly | Arg | Ser | Lys | Val | Ile | Lys | Gly | Ser | Leu | Pro | Leu | Ile |
| | | 275 | | | | | 280 | | | | | 285 | | | |
| Gly | Glu | Ala | Asp | Cys | Leu | His | Ala | Lys | Tyr | Gly | Gly | Leu | Asn | Lys | Ser |
| | 290 | | | | | 295 | | | | | 300 | | | | |
| Lys | Pro | Tyr | Tyr | Thr | Gly | Glu | His | Ala | Lys | Ala | Ile | Gly | Asn | Cys | Pro |
| 305 | | | | | 310 | | | | | 315 | | | | | 320 |
| Ile | Trp | Val | Lys | Thr | Pro | Leu | Lys | Leu | Ala | Asn | Gly | Thr | Lys | Tyr | Arg |
| | | | | 325 | | | | | 330 | | | | | 335 | |
| Pro | Pro | Ala | Lys | Leu | Leu | Lys | Glu | Arg | | | | | | | |
| | | | 340 | | | | | 345 | | | | | | | |

(2) INFORMATION FOR SEQ ID NO:9:

(i) SEQUENCE CHARACTERISTICS:
        (A) LENGTH: 1080 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 46..1080
        (D) OTHER INFORMATION: /label=HK89

(xi) SEQUENCE DESCRIPTION: SEQ ID NO:9:

| | | | | | | | | | | | |
|---|---|---|---|---|---|---|---|---|---|---|---|
| ATGAAGGCAA | TAATTGTACT | ACTCATGGTA | GTAACATCCA | ACGCA | GAT | CGA | ATC | | | | 54 |
| | | | | | Asp | Arg | Ile | | | | |
| | | | | | 1 | | | | | | |

| | | | | | | | | | | | | | | | | |
|---|---|---|---|---|---|---|---|---|---|---|---|---|---|---|---|---|
| TGC | ACT | GGG | ATA | ACA | TCT | TCA | AAC | TCA | CCT | CAT | GTG | GTC | AAA | ACA | GCT | 102 |
| Cys | Thr | Gly | Ile | Thr | Ser | Ser | Asn | Ser | Pro | His | Val | Val | Lys | Thr | Ala | |
| | 5 | | | | | 10 | | | | | 15 | | | | | |
| ACT | CAA | GGG | GAA | GTC | AAT | GTG | ACT | GGT | GTG | ATA | CCA | CTG | ACA | ACA | ACA | 150 |
| Thr | Gln | Gly | Glu | Val | Asn | Val | Thr | Gly | Val | Ile | Pro | Leu | Thr | Thr | Thr | |
| 20 | | | | | 25 | | | | | 30 | | | | | 35 | |
| CCA | ACA | AAA | TCT | CAT | TTT | GCA | AAT | CTC | AAA | GGA | ACA | AAG | ACC | AGA | GGG | 198 |
| Pro | Thr | Lys | Ser | His | Phe | Ala | Asn | Leu | Lys | Gly | Thr | Lys | Thr | Arg | Gly | |
| | | | | 40 | | | | | 45 | | | | | 50 | | |
| AAA | CTA | TGC | CCA | AAC | TGT | CTC | AAC | TGC | ACA | GAT | CTG | GAT | GTG | GCC | TTG | 246 |
| Lys | Leu | Cys | Pro | Asn | Cys | Leu | Asn | Cys | Thr | Asp | Leu | Asp | Val | Ala | Leu | |

| | | | | | | | | | | | | | | | | |
|---|---|---|---|---|---|---|---|---|---|---|---|---|---|---|---|---|
| | | | 55 | | | | 60 | | | | | 65 | | | | |
| GCG | AGA | CCA | ATG | TGT | ATG | GGG | ACC | ATA | CCT | TCG | GCA | AAA | GCT | TCA | ATA | 294 |
| Ala | Arg | Pro | Met | Cys | Met | Gly | Thr | Ile | Pro | Ser | Ala | Lys | Ala | Ser | Ile | |
| | | 70 | | | | 75 | | | | | 80 | | | | | |
| CTC | CAC | GAA | GTC | AGA | CCT | GTT | ACA | TCC | GGG | TGC | TTT | CCT | ATA | ATG | CAC | 342 |
| Leu | His | Glu | Val | Arg | Pro | Val | Thr | Ser | Gly | Cys | Phe | Pro | Ile | Met | His | |
| | 85 | | | | | 90 | | | | | 95 | | | | | |
| GAC | AGA | ACA | AAA | ATC | ATA | CAG | CTA | CCC | AAT | CTT | CTC | AGA | GGA | TAT | GAA | 390 |
| Asp | Arg | Thr | Lys | Ile | Ile | Gln | Leu | Pro | Asn | Leu | Leu | Arg | Gly | Tyr | Glu | |
| 100 | | | | | 105 | | | | | 110 | | | | | 115 | |
| AAT | ATT | AGA | TTA | TCA | ACC | CAT | AAC | GTT | ATC | AAC | GCA | GAA | AGG | GCA | CCA | 438 |
| Asn | Ile | Arg | Leu | Ser | Thr | His | Asn | Val | Ile | Asn | Ala | Glu | Arg | Ala | Pro | |
| | | | | 120 | | | | | 125 | | | | | 130 | | |
| GGA | GGA | CCC | TAC | AGA | CTT | GGA | ACC | TCA | GGA | TCT | TGC | CCT | AAC | GTT | ACC | 486 |
| Gly | Gly | Pro | Tyr | Arg | Leu | Gly | Thr | Ser | Gly | Ser | Cys | Pro | Asn | Val | Thr | |
| | | | 135 | | | | | 140 | | | | | 145 | | | |
| AGT | AGA | AGC | GGA | TTC | TTC | GCA | ACA | ATG | GCT | TGG | GCT | GTC | CCA | AGG | GAC | 534 |
| Ser | Arg | Ser | Gly | Phe | Phe | Ala | Thr | Met | Ala | Trp | Ala | Val | Pro | Arg | Asp | |
| | | 150 | | | | | 155 | | | | | 160 | | | | |
| AAC | AAA | ACA | GCA | ACG | AAT | CCA | CTA | ACA | GTA | GAA | GTA | CCA | TAC | ATT | TGT | 582 |
| Asn | Lys | Thr | Ala | Thr | Asn | Pro | Leu | Thr | Val | Glu | Val | Pro | Tyr | Ile | Cys | |
| | 165 | | | | | 170 | | | | | 175 | | | | | |
| ACA | AAA | GGA | GAA | GAC | CAA | ATT | ACT | GTT | TGG | GGG | TTC | CAT | TCT | GAT | AGC | 630 |
| Thr | Lys | Gly | Glu | Asp | Gln | Ile | Thr | Val | Trp | Gly | Phe | His | Ser | Asp | Ser | |
| 180 | | | | | 185 | | | | | 190 | | | | | 195 | |
| AAA | ACC | CAA | ATG | AAA | AAC | CTC | TAT | GGA | GAC | TCA | AAT | CCT | CAA | AAG | TTC | 678 |
| Lys | Thr | Gln | Met | Lys | Asn | Leu | Tyr | Gly | Asp | Ser | Asn | Pro | Gln | Lys | Phe | |
| | | | 200 | | | | | 205 | | | | | 210 | | | |
| ACC | TCA | TCT | GCC | AAT | GGA | GTA | ACC | ACA | CAT | TAT | GTT | TCT | CAG | ATT | GGT | 726 |
| Thr | Ser | Ser | Ala | Asn | Gly | Val | Thr | Thr | His | Tyr | Val | Ser | Gln | Ile | Gly | |
| | | | 215 | | | | | 220 | | | | | 225 | | | |
| GAC | TTC | CCA | AAT | CAA | ACA | GAA | GAC | GGA | GGG | CTA | CCA | CAA | AGC | GGC | AGA | 774 |
| Asp | Phe | Pro | Asn | Gln | Thr | Glu | Asp | Gly | Gly | Leu | Pro | Gln | Ser | Gly | Arg | |
| | | 230 | | | | | 235 | | | | | 240 | | | | |
| ATT | GTT | GTT | GAT | TAC | ATG | GTG | CAA | AAA | CCT | GGG | AAA | TCA | GGA | ACA | ATT | 822 |
| Ile | Val | Val | Asp | Tyr | Met | Val | Gln | Lys | Pro | Gly | Lys | Ser | Gly | Thr | Ile | |
| | 245 | | | | | 250 | | | | | 255 | | | | | |
| GTC | TAT | CAA | AGA | GGT | GTT | TTG | TTG | CCT | CAA | AAG | GTG | TGG | TGC | GCA | AGT | 870 |
| Val | Tyr | Gln | Arg | Gly | Val | Leu | Leu | Pro | Gln | Lys | Val | Trp | Cys | Ala | Ser | |
| 260 | | | | | 265 | | | | | 270 | | | | | 275 | |
| GGC | AGG | AGC | AAG | GTA | ATA | AAA | GGG | TCC | TTG | CCT | TTA | ATT | GGT | GAA | GCA | 918 |
| Gly | Arg | Ser | Lys | Val | Ile | Lys | Gly | Ser | Leu | Pro | Leu | Ile | Gly | Glu | Ala | |
| | | | | 280 | | | | | 285 | | | | | 290 | | |
| GAT | TGC | CTT | CAC | GAA | AAA | TAC | GGT | GGA | TTA | AAC | AAA | AGC | AAG | CCT | TAC | 966 |
| Asp | Cys | Leu | His | Glu | Lys | Tyr | Gly | Gly | Leu | Asn | Lys | Ser | Lys | Pro | Tyr | |
| | | | 295 | | | | | 300 | | | | | 305 | | | |
| TAC | ACA | GGA | GAA | CAT | GCA | AAA | GCC | ATA | GGG | AAT | TGC | CCG | ATA | TGG | GTG | 1014 |
| Tyr | Thr | Gly | Glu | His | Ala | Lys | Ala | Ile | Gly | Asn | Cys | Pro | Ile | Trp | Val | |
| | | 310 | | | | | 315 | | | | | 320 | | | | |
| AAA | ACA | CCT | TTG | AAG | CTT | GCC | AAT | GGA | ACC | AAA | TAT | AGA | CCT | CCT | GCA | 1062 |
| Lys | Thr | Pro | Leu | Lys | Leu | Ala | Asn | Gly | Thr | Lys | Tyr | Arg | Pro | Pro | Ala | |
| | 325 | | | | | 330 | | | | | 335 | | | | | |
| AAA | CTA | TTA | AAG | GAA | AGG | | | | | | | | | | | 1080 |
| Lys | Leu | Leu | Lys | Glu | Arg | | | | | | | | | | | |
| 340 | | | | | 345 | | | | | | | | | | | |

( 2 ) INFORMATION FOR SEQ ID NO:10:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| Asp | Arg | Ile | Cys | Thr | Gly | Ile | Thr | Ser | Ser | Asn | Ser | Pro | His | Val | Val |
|---|---|---|---|---|---|---|---|---|---|---|---|---|---|---|---|
| 1 | | | | 5 | | | | | 10 | | | | | 15 | |
| Lys | Thr | Ala | Thr | Gln | Gly | Glu | Val | Asn | Val | Thr | Gly | Val | Ile | Pro | Leu |
| | | | 20 | | | | | 25 | | | | | 30 | | |
| Thr | Thr | Thr | Pro | Thr | Lys | Ser | His | Phe | Ala | Asn | Leu | Lys | Gly | Thr | Lys |
| | | 35 | | | | | 40 | | | | | 45 | | | |
| Thr | Arg | Gly | Lys | Leu | Cys | Pro | Asn | Cys | Leu | Asn | Cys | Thr | Asp | Leu | Asp |
| | 50 | | | | | 55 | | | | | 60 | | | | |
| Val | Ala | Leu | Ala | Arg | Pro | Met | Cys | Met | Gly | Thr | Ile | Pro | Ser | Ala | Lys |
| 65 | | | | | 70 | | | | 75 | | | | | | 80 |
| Ala | Ser | Ile | Leu | His | Glu | Val | Arg | Pro | Val | Thr | Ser | Gly | Cys | Phe | Pro |
| | | | | 85 | | | | | 90 | | | | | 95 | |
| Ile | Met | His | Asp | Arg | Thr | Lys | Ile | Ile | Gln | Leu | Pro | Asn | Leu | Leu | Arg |
| | | | 100 | | | | | 105 | | | | | 110 | | |
| Gly | Tyr | Glu | Asn | Ile | Arg | Leu | Ser | Thr | His | Asn | Val | Ile | Asn | Ala | Glu |
| | | 115 | | | | | 120 | | | | | 125 | | | |
| Arg | Ala | Pro | Gly | Gly | Pro | Tyr | Arg | Leu | Gly | Thr | Ser | Gly | Ser | Cys | Pro |
| | 130 | | | | | 135 | | | | | 140 | | | | |
| Asn | Val | Thr | Ser | Arg | Ser | Gly | Phe | Phe | Ala | Thr | Met | Ala | Trp | Ala | Val |
| 145 | | | | | 150 | | | | | 155 | | | | | 160 |
| Pro | Arg | Asp | Asn | Lys | Thr | Ala | Thr | Asn | Pro | Leu | Thr | Val | Glu | Val | Pro |
| | | | | 165 | | | | | 170 | | | | | 175 | |
| Tyr | Ile | Cys | Thr | Lys | Gly | Glu | Asp | Gln | Ile | Thr | Val | Trp | Gly | Phe | His |
| | | | 180 | | | | | 185 | | | | | 190 | | |
| Ser | Asp | Ser | Lys | Thr | Gln | Met | Lys | Asn | Leu | Tyr | Gly | Asp | Ser | Asn | Pro |
| | | 195 | | | | | 200 | | | | | 205 | | | |
| Gln | Lys | Phe | Thr | Ser | Ser | Ala | Asn | Gly | Val | Thr | Thr | His | Tyr | Val | Ser |
| | 210 | | | | | 215 | | | | | 220 | | | | |
| Gln | Ile | Gly | Asp | Phe | Pro | Asn | Gln | Thr | Glu | Asp | Gly | Gly | Leu | Pro | Gln |
| 225 | | | | | 230 | | | | | 235 | | | | | 240 |
| Ser | Gly | Arg | Ile | Val | Val | Asp | Tyr | Met | Val | Gln | Lys | Pro | Gly | Lys | Ser |
| | | | | 245 | | | | | 250 | | | | | 255 | |
| Gly | Thr | Ile | Val | Tyr | Gln | Arg | Gly | Val | Leu | Leu | Pro | Gln | Lys | Val | Trp |
| | | | 260 | | | | | 265 | | | | | 270 | | |
| Cys | Ala | Ser | Gly | Arg | Ser | Lys | Val | Ile | Lys | Gly | Ser | Leu | Pro | Leu | Ile |
| | | 275 | | | | | 280 | | | | | 285 | | | |
| Gly | Glu | Ala | Asp | Cys | Leu | His | Glu | Lys | Tyr | Gly | Gly | Leu | Asn | Lys | Ser |
| | 290 | | | | | 295 | | | | | 300 | | | | |
| Lys | Pro | Tyr | Tyr | Thr | Gly | Glu | His | Ala | Lys | Ala | Ile | Gly | Asn | Cys | Pro |
| 305 | | | | | 310 | | | | | 315 | | | | | 320 |
| Ile | Trp | Val | Lys | Thr | Pro | Leu | Lys | Leu | Ala | Asn | Gly | Thr | Lys | Tyr | Arg |
| | | | | 325 | | | | | 330 | | | | | 335 | |
| Pro | Pro | Ala | Lys | Leu | Leu | Lys | Glu | Arg | | | | | | | |
| | | | 340 | | | | | 345 | | | | | | | |

( 2 ) INFORMATION FOR SEQ ID NO:11:

( i ) SEQUENCE CHARACTERISTICS:
( A ) LENGTH: 1080 base pairs
( B ) TYPE: nucleic acid
( C ) STRANDEDNESS: single
( D ) TOPOLOGY: linear ( i i ) MOLECULE TYPE: cDNA ( i x ) FEATURE:

(A) NAME/KEY: CDS
(B) LOCATION: 46..1080
(D) OTHER INFORMATION: /label=HK289

(xi) SEQUENCE DESCRIPTION: SEQ ID NO:11:

```
ATGAAGGCAA TAATTGTACT ACTCATGGTA GTAACATCCA ACGCA GAT CGA ATC         54
                                                   Asp Arg Ile
                                                    1

TGC ACT GGG ATA ACA TCT TCA AAC TCA CCT CAT GTG GTC AAA ACA GCT     102
Cys Thr Gly Ile Thr Ser Ser Asn Ser Pro His Val Val Lys Thr Ala
      5              10                  15

ACT CAA GGG GAA GTC AAT GTG ACT GGT GTG ATA CCA CTG ACA ACA ACA     150
Thr Gln Gly Glu Val Asn Val Thr Gly Val Ile Pro Leu Thr Thr Thr
 20              25                  30                      35

CCA ACA AAA TCT CAT TTT GCA AAT CTA AAA GGA ACA AAG ACC AGA GGG     198
Pro Thr Lys Ser His Phe Ala Asn Leu Lys Gly Thr Lys Thr Arg Gly
                  40                  45                  50

AAA CTA TGC CCA AAC TGT CTC AAC TGC ACA GAT CTG GAT GTG GCC TTG     246
Lys Leu Cys Pro Asn Cys Leu Asn Cys Thr Asp Leu Asp Val Ala Leu
              55                  60                  65

GCG AGA CCA ATG TGT GTG GGG ACC ACA CCT TCG GCA AAA GCT TCA ATA     294
Ala Arg Pro Met Cys Val Gly Thr Thr Pro Ser Ala Lys Ala Ser Ile
          70                  75                  80

CTC CAC GAA GTC AGA CCT GTT ACA TCC GGG TGC TTT CCT ATA ATG CAC     342
Leu His Glu Val Arg Pro Val Thr Ser Gly Cys Phe Pro Ile Met His
      85                  90                  95

GAC AGA ACA AAA ATC AGA CAG CTA CCC AAT CTT CTC AGA GGA TAT GAA     390
Asp Arg Thr Lys Ile Arg Gln Leu Pro Asn Leu Leu Arg Gly Tyr Glu
100                 105                 110                 115

AAT ATC AGA TTA TCA ACC CAA AAC GTT ATC AAT GCA GAA AGA GCA CCA     438
Asn Ile Arg Leu Ser Thr Gln Asn Val Ile Asn Ala Glu Arg Ala Pro
                 120                 125                 130

GGA GGA CCC TAC AGA CTT GGA ACC TCA GGA TCT TGC CCT AAC GTT ACC     486
Gly Gly Pro Tyr Arg Leu Gly Thr Ser Gly Ser Cys Pro Asn Val Thr
             135                 140                 145

AGT AGA GAC GGA TTC TTC GCA ACA ATG GCT TGG GCT GTC CCA AGG GAC     534
Ser Arg Asp Gly Phe Phe Ala Thr Met Ala Trp Ala Val Pro Arg Asp
         150                 155                 160

AAC AAA ACA GCA ACG AAT CCA CTA ACA GTA GAA GTA CCA TAC ATT TGT     582
Asn Lys Thr Ala Thr Asn Pro Leu Thr Val Glu Val Pro Tyr Ile Cys
165                 170                 175

ACA AAA GGA GAA GAC CAA ATT ACT GTT TGG GGG TTC CAT TCT GAT AGC     630
Thr Lys Gly Glu Asp Gln Ile Thr Val Trp Gly Phe His Ser Asp Ser
180                 185                 190                 195

AAA ACC CAA ATG AAA AAC CTC TAT GGA GAC TCA AAT CCT CAA AAG TTC     678
Lys Thr Gln Met Lys Asn Leu Tyr Gly Asp Ser Asn Pro Gln Lys Phe
                 200                 205                 210

ACC TCA TCT GCC AAT GGA GTA ACC ACA CAT TAT GTT TCT CAG ATT GGT     726
Thr Ser Ser Ala Asn Gly Val Thr Thr His Tyr Val Ser Gln Ile Gly
             215                 220                 225

GGC TTC CCA AAT CAA ACA GAA GAC GGA GGG CTA CCA CAA AGC GGC AGA     774
Gly Phe Pro Asn Gln Thr Glu Asp Gly Gly Leu Pro Gln Ser Gly Arg
         230                 235                 240

ATT GTT GTT GAT TAC ATG GTG CAA AAA CCT GGG AAA ACA GGA ACA ATT     822
Ile Val Val Asp Tyr Met Val Gln Lys Pro Gly Lys Thr Gly Thr Ile
245                 250                 255

GTC TAT CAA AGA GGT GTT TTG TTG CCT CAA AAG GTG TGG TGC GCA AGT     870
Val Tyr Gln Arg Gly Val Leu Leu Pro Gln Lys Val Trp Cys Ala Ser
260                 265                 270                 275

GGC AGG AGC AAG GTA ATA AAA GGG TCC TTG CCT TTA ATT GGT GAA GCA     918
Gly Arg Ser Lys Val Ile Lys Gly Ser Leu Pro Leu Ile Gly Glu Ala
             280                 285                 290
```

```
GAT TGC CTT CAC GAA AAA TAC GGT GGA TTA AAC AAA AGC AAG CCT TAC        966
Asp Cys Leu His Glu Lys Tyr Gly Gly Leu Asn Lys Ser Lys Pro Tyr
            295                 300                 305

TAC ACA GGA GAA CAT GCA AAA GCC ATA GGA AAT TGC CCA ATA TGG GTG       1014
Tyr Thr Gly Glu His Ala Lys Ala Ile Gly Asn Cys Pro Ile Trp Val
            310                 315                 320

AAA ACA CCT TTG AAG CTT GCC AAT GGA ACC AAA TAT AGA CCT CCT GCA       1062
Lys Thr Pro Leu Lys Leu Ala Asn Gly Thr Lys Tyr Arg Pro Pro Ala
            325                 330                 335

AAA CTA TTA AAG GAA AGG                                               1080
Lys Leu Leu Lys Glu Arg
340                 345
```

( 2 ) INFORMATION FOR SEQ ID NO:12:

( i ) SEQUENCE CHARACTERISTICS:
      ( A ) LENGTH: 345 amino acids
      ( B ) TYPE: amino acid
      ( D ) TOPOLOGY: linear ( i i ) MOLECULE TYPE: protein ( x i ) SEQUENCE DESCRIPTION: SEQ ID NO:12:

```
Asp Arg Ile Cys Thr Gly Ile Thr Ser Ser Asn Ser Pro His Val Val
 1            5                  10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Lys
            35                  40                  45

Thr Arg Gly Lys Leu Cys Pro Asn Cys Leu Asn Cys Thr Asp Leu Asp
        50                  55                  60

Val Ala Leu Ala Arg Pro Met Cys Val Gly Thr Thr Pro Ser Ala Lys
65                  70                  75                  80

Ala Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr Gln Asn Val Ile Asn Ala Glu
            115                 120                 125

Arg Ala Pro Gly Gly Pro Tyr Arg Leu Gly Thr Ser Gly Ser Cys Pro
        130                 135                 140

Asn Val Thr Ser Arg Asp Gly Phe Phe Ala Thr Met Ala Trp Ala Val
145                 150                 155                 160

Pro Arg Asp Asn Lys Thr Ala Thr Asn Pro Leu Thr Val Glu Val Pro
                165                 170                 175

Tyr Ile Cys Thr Lys Gly Glu Asp Gln Ile Thr Val Trp Gly Phe His
            180                 185                 190

Ser Asp Ser Lys Thr Gln Met Lys Asn Leu Tyr Gly Asp Ser Asn Pro
            195                 200                 205

Gln Lys Phe Thr Ser Ser Ala Asn Gly Val Thr Thr His Tyr Val Ser
        210                 215                 220

Gln Ile Gly Gly Phe Pro Asn Gln Thr Glu Asp Gly Gly Leu Pro Gln
225                 230                 235                 240

Ser Gly Arg Ile Val Val Asp Tyr Met Val Gln Lys Pro Gly Lys Thr
                245                 250                 255

Gly Thr Ile Val Tyr Gln Arg Gly Val Leu Leu Pro Gln Lys Val Trp
            260                 265                 270

Cys Ala Ser Gly Arg Ser Lys Val Ile Lys Gly Ser Leu Pro Leu Ile
            275                 280                 285
```

| | | | | | | | | | | | | | | | |
|---|---|---|---|---|---|---|---|---|---|---|---|---|---|---|---|
| Gly | Glu | Ala | Asp | Cys | Leu | His | Glu | Lys | Tyr | Gly | Gly | Leu | Asn | Lys | Ser |
| | 290 | | | | 295 | | | | | 300 | | | | | |
| Lys | Pro | Tyr | Tyr | Thr | Gly | Glu | His | Ala | Lys | Ala | Ile | Gly | Asn | Cys | Pro |
| 305 | | | | | 310 | | | | 315 | | | | | | 320 |
| Ile | Trp | Val | Lys | Thr | Pro | Leu | Lys | Leu | Ala | Asn | Gly | Thr | Lys | Tyr | Arg |
| | | | | 325 | | | | | 330 | | | | | 335 | |
| Pro | Pro | Ala | Lys | Leu | Leu | Lys | Glu | Arg | | | | | | | |
| | | | 340 | | | | | 345 | | | | | | | |

( 2 ) INFORMATION FOR SEQ ID NO:13:

( i ) SEQUENCE CHARACTERISTICS:
            ( A ) LENGTH: 1080 base pairs
            ( B ) TYPE: nucleic acid
            ( C ) STRANDEDNESS: single
            ( D ) TOPOLOGY: linear ( i i ) MOLECULE TYPE: cDNA ( i x ) FEATURE:
            ( A ) NAME/KEY: CDS
            ( B ) LOCATION: 46..1080
            ( D ) OTHER INFORMATION: /label=VI103

( x i ) SEQUENCE DESCRIPTION: SEQ ID NO:13:

| | | | | | | | | | | | | | | | | |
|---|---|---|---|---|---|---|---|---|---|---|---|---|---|---|---|---|
| ATGAAGGCAA | TAATTGTACT | ACTCATGGTA | GTAACATCCA | ACGCA | GAT | CGA | ATC | | | | | | | | | 54 |
| | | | | | Asp | Arg | Ile | | | | | | | | | |
| | | | | | 1 | | | | | | | | | | | |
| TGC | ACT | GGG | ATA | ACA | TCT | TCA | AAC | TCA | CCT | CAT | GTG | GTC | AAA | ACA | GCT | 102 |
| Cys | Thr | Gly | Ile | Thr | Ser | Ser | Asn | Ser | Pro | His | Val | Val | Lys | Thr | Ala | |
| | 5 | | | | | 10 | | | | | 15 | | | | | |
| ACT | CAA | GGG | GAA | GTC | AAT | GTG | ACT | GGT | GTG | ATA | CCA | CTG | ACA | ACA | ACA | 150 |
| Thr | Gln | Gly | Glu | Val | Asn | Val | Thr | Gly | Val | Ile | Pro | Leu | Thr | Thr | Thr | |
| 20 | | | | | 25 | | | | | 30 | | | | | 35 | |
| CCA | ACA | AAA | TCT | CAT | TTT | GCA | AAT | CTC | AAA | GGA | ACA | AAG | ACC | AGA | GGG | 198 |
| Pro | Thr | Lys | Ser | His | Phe | Ala | Asn | Leu | Lys | Gly | Thr | Lys | Thr | Arg | Gly | |
| | | | | 40 | | | | | 45 | | | | | 50 | | |
| AAA | CTA | TGC | CCA | AAC | TGT | CTC | AAC | TGC | ACA | GAT | CTG | GAT | GTG | GCC | TTG | 246 |
| Lys | Leu | Cys | Pro | Asn | Cys | Leu | Asn | Cys | Thr | Asp | Leu | Asp | Val | Ala | Leu | |
| | | | 55 | | | | | 60 | | | | | 65 | | | |
| GCG | AGA | CCA | ATG | TGT | GTG | GGG | ACC | ACA | CCT | TCG | GCA | AAA | GCT | TCA | ATA | 294 |
| Ala | Arg | Pro | Met | Cys | Val | Gly | Thr | Ile | Pro | Ser | Ala | Lys | Ala | Ser | Ile | |
| | | 70 | | | | | 75 | | | | | 80 | | | | |
| CTC | CAC | GAA | GTC | AGA | CCT | GTT | ACA | TCC | GGG | TGC | TTT | CCT | ATA | ATG | CAC | 342 |
| Leu | His | Glu | Val | Arg | Pro | Val | Thr | Ser | Gly | Cys | Phe | Pro | Ile | Met | His | |
| | 85 | | | | | 90 | | | | | 95 | | | | | |
| GAC | AGA | ACA | AAA | ATC | AGA | CAG | CTA | CCC | AAT | CTT | CTC | AGA | GGA | TAT | GAA | 390 |
| Asp | Arg | Thr | Lys | Ile | Arg | Gln | Leu | Pro | Asn | Leu | Leu | Arg | Gly | Tyr | Glu | |
| 100 | | | | | 105 | | | | | 110 | | | | | 115 | |
| AAT | ATC | AGA | TTA | TCA | ACC | CAT | AAC | GTT | ATC | AAC | GCA | GAA | GGG | GCA | CCA | 438 |
| Asn | Ile | Arg | Leu | Ser | Thr | His | Asn | Val | Ile | Asn | Ala | Glu | Gly | Ala | Pro | |
| | | | | 120 | | | | | 125 | | | | | 130 | | |
| GGA | GGA | CCC | TAC | AGA | CTT | GGA | ACC | TCA | GGA | TCT | TGC | CCT | AAC | GTT | ACC | 486 |
| Gly | Gly | Pro | Tyr | Arg | Leu | Gly | Thr | Ser | Gly | Ser | Cys | Pro | Asn | Val | Thr | |
| | | | 135 | | | | | 140 | | | | | 145 | | | |
| AGT | AGA | AAC | GGA | TTC | TTC | GCA | ACA | ATG | GCT | TGG | GCT | GTC | CCA | AGG | GAC | 534 |
| Ser | Arg | Asn | Gly | Phe | Phe | Ala | Thr | Met | Ala | Trp | Ala | Val | Pro | Arg | Asp | |
| | | 150 | | | | | 155 | | | | | 160 | | | | |
| AAC | AAA | ACA | GCA | ACG | AAT | CCA | CTA | ACA | GTA | GAA | GTA | CCA | TAC | ATT | TGT | 582 |
| Asn | Lys | Thr | Ala | Thr | Asn | Pro | Leu | Thr | Val | Glu | Val | Pro | Tyr | Ile | Cys | |
| | 165 | | | | | 170 | | | | | 175 | | | | | |
| GCA | AAA | GGA | GAA | GAC | CAA | ATT | ACT | GTT | TGG | GGG | TTC | CAC | TCT | GAT | AAC | 630 |
| Ala | Lys | Gly | Glu | Asp | Gln | Ile | Thr | Val | Trp | Gly | Phe | His | Ser | Asp | Asn | |

|  |  |  |  |  |  |  |  |  |  |  |  |  |  |  |  |  |
|---|---|---|---|---|---|---|---|---|---|---|---|---|---|---|---|---|
| 180 |  |  |  |  | 185 |  |  |  |  | 190 |  |  |  |  | 195 |  |
| AAA<br>Lys | GCC<br>Ala | CAA<br>Gln | ATG<br>Met<br>200 | AAA<br>Lys | AAC<br>Asn | CTC<br>Leu | TAT<br>Tyr | GGA<br>Gly | GAC<br>Asp<br>205 | TCA<br>Ser | AAT<br>Asn | CCT<br>Pro | CAA<br>Gln | AAG<br>Lys<br>210 | TTC<br>Phe | 678 |
| ACC<br>Thr | TCA<br>Ser | TCT<br>Ser | GCC<br>Ala | AAT<br>Asn<br>215 | GGA<br>Gly | GTA<br>Val | ACC<br>Thr | ACA<br>Thr | CAT<br>His<br>220 | TAT<br>Tyr | GTT<br>Val | TCT<br>Ser | CAG<br>Gln | ATT<br>Ile<br>225 | GGT<br>Gly | 726 |
| GGC<br>Gly | TTC<br>Phe | CCA<br>Pro<br>230 | AAT<br>Asn | CAA<br>Gln | ACA<br>Thr | GAA<br>Glu | GAC<br>Asp<br>235 | GGA<br>Gly | GGG<br>Gly | CTA<br>Leu | CCA<br>Pro | CAA<br>Gln<br>240 | AGC<br>Ser | GGC<br>Gly | AGA<br>Arg | 774 |
| ATT<br>Ile | GTT<br>Val | GTT<br>Val<br>245 | GAT<br>Asp | TAC<br>Tyr | ATG<br>Met | GTG<br>Val<br>250 | CAA<br>Gln | AAA<br>Lys | CCT<br>Pro | GGG<br>Gly | AAA<br>Lys<br>255 | ACA<br>Thr | GGA<br>Gly | ACA<br>Thr | ATT<br>Ile | 822 |
| GTC<br>Val<br>260 | TAT<br>Tyr | CAA<br>Gln | AGA<br>Arg | GGT<br>Gly | GTT<br>Val<br>265 | TTG<br>Leu | TTG<br>Leu | CCT<br>Pro | CAA<br>Gln | AAG<br>Lys<br>270 | GTG<br>Val | TGG<br>Trp | TGC<br>Cys | GCA<br>Ala | AGT<br>Ser<br>275 | 870 |
| GGC<br>Gly | AGG<br>Arg | AGC<br>Ser | AAG<br>Lys | GTA<br>Val<br>280 | ATA<br>Ile | AAA<br>Lys | GGG<br>Gly | TCC<br>Ser | TTG<br>Leu<br>285 | CCT<br>Pro | TTA<br>Leu | ATT<br>Ile | GGT<br>Gly | GAA<br>Glu<br>290 | GCA<br>Ala | 918 |
| GAT<br>Asp | TGC<br>Cys | CTT<br>Leu | CAC<br>His<br>295 | GCA<br>Ala | AAA<br>Lys | TAC<br>Tyr | GGT<br>Gly | GGA<br>Gly<br>300 | TTA<br>Leu | AAC<br>Asn | AAA<br>Lys | AGC<br>Ser | AAG<br>Lys<br>305 | CCT<br>Pro | TAC<br>Tyr | 966 |
| TAC<br>Tyr | ACA<br>Thr | GGA<br>Gly<br>310 | GAA<br>Glu | CAT<br>His | GCA<br>Ala | AAA<br>Lys | GCC<br>Ala<br>315 | ATA<br>Ile | GGA<br>Gly | AAT<br>Asn | TGC<br>Cys | CCA<br>Pro<br>320 | ATA<br>Ile | TGG<br>Trp | GTG<br>Val | 1014 |
| AAA<br>Lys | ACA<br>Thr | CCT<br>Pro<br>325 | TTG<br>Leu | AAG<br>Lys | CTT<br>Leu | GCC<br>Ala | AAT<br>Asn<br>330 | GGA<br>Gly | ACC<br>Thr | AAA<br>Lys | TAT<br>Tyr | AGA<br>Arg<br>335 | CCT<br>Pro | CCT<br>Pro | GCA<br>Ala | 1062 |
| AAA<br>Lys<br>340 | CTA<br>Leu | TTA<br>Leu | AAG<br>Lys | GAA<br>Glu | AGG<br>Arg<br>345 |  |  |  |  |  |  |  |  |  |  | 1080 |

( 2 ) INFORMATION FOR SEQ ID NO:14:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| Asp<br>1 | Arg | Ile | Cys | Thr<br>5 | Gly | Ile | Thr | Ser | Ser<br>10 | Asn | Ser | Pro | His | Val<br>15 | Val |
|---|---|---|---|---|---|---|---|---|---|---|---|---|---|---|---|
| Lys | Thr | Ala | Thr<br>20 | Gln | Gly | Glu | Val | Asn<br>25 | Val | Thr | Gly | Val | Ile<br>30 | Pro | Leu |
| Thr | Thr | Thr<br>35 | Pro | Thr | Lys | Ser | His<br>40 | Phe | Ala | Asn | Leu | Lys<br>45 | Gly | Thr | Lys |
| Thr | Arg<br>50 | Gly | Lys | Leu | Cys | Pro<br>55 | Asn | Cys | Leu | Asn | Cys<br>60 | Thr | Asp | Leu | Asp |
| Val<br>65 | Ala | Leu | Ala | Arg | Pro<br>70 | Met | Cys | Val | Gly | Thr<br>75 | Ile | Pro | Ser | Ala | Lys<br>80 |
| Ala | Ser | Ile | Leu | His<br>85 | Glu | Val | Arg | Pro | Val<br>90 | Thr | Ser | Gly | Cys | Phe<br>95 | Pro |
| Ile | Met | His | Asp<br>100 | Arg | Thr | Lys | Ile | Arg<br>105 | Gln | Leu | Pro | Asn | Leu<br>110 | Leu | Arg |
| Gly | Tyr | Glu<br>115 | Asn | Ile | Arg | Leu | Ser<br>120 | Thr | Gln | Asn | Val | Ile<br>125 | Asn | Ala | Glu |
| Gly | Ala<br>130 | Pro | Gly | Gly | Pro | Tyr<br>135 | Arg | Leu | Gly | Thr | Ser<br>140 | Gly | Ser | Cys | Pro |
| Asn | Val | Thr | Ser | Arg | Asn | Gly | Phe | Phe | Ala | Thr | Met | Ala | Trp | Ala | Val |

| | | | | | | | | | | | | | | | |
|---|---|---|---|---|---|---|---|---|---|---|---|---|---|---|---|
|145| | | | |150| | | | |155| | | | |160|

Pro Arg Asp Asn Lys Thr Ala Thr Asn Pro Leu Thr Val Glu Val Pro
                         165                      170                   175

Tyr Ile Cys Ala Lys Gly Glu Asp Gln Ile Thr Val Trp Gly Phe His
               180                      185                   190

Ser Asp Asn Lys Ala Gln Met Lys Asn Leu Tyr Gly Asp Ser Asn Pro
           195                       200                 205

Gln Lys Phe Thr Ser Ser Ala Asn Gly Val Thr Thr His Tyr Val Ser
210                    215                      220

Gln Ile Gly Gly Phe Pro Asn Gln Thr Glu Asp Gly Gly Leu Pro Gln
225                    230                  235                   240

Ser Gly Arg Ile Val Val Asp Tyr Met Val Gln Lys Pro Gly Lys Thr
               245                      250                 255

Gly Thr Ile Val Tyr Gln Arg Gly Val Leu Leu Pro Gln Lys Val Trp
           260                       265                 270

Cys Ala Ser Gly Arg Ser Lys Val Ile Lys Gly Ser Leu Pro Leu Ile
        275                      280                 285

Gly Glu Ala Asp Cys Leu His Ala Lys Tyr Gly Gly Leu Asn Lys Ser
   290                      295                     300

Lys Pro Tyr Tyr Thr Gly Glu His Ala Lys Ala Ile Gly Asn Cys Pro
305                    310                  315                 320

Ile Trp Val Lys Thr Pro Leu Lys Leu Ala Asn Gly Thr Lys Tyr Arg
               325                      330                 335

Pro Pro Ala Lys Leu Leu Lys Glu Arg
           340                      345

( 2 ) INFORMATION FOR SEQ ID NO:15:

( i ) SEQUENCE CHARACTERISTICS:
        ( A ) LENGTH: 1080 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 46..1080
        ( D ) OTHER INFORMATION: /label=SD89

( x i ) SEQUENCE DESCRIPTION: SEQ ID NO:15:

ATGAAGGCAA TAATTGTACT ACTCATGGTA GTAACATCCA ACGCA GAT CGA ATC    54
                                                                         Asp Arg Ile
                                                                            1

TGC ACT GGG ATA ACA TCT TCA AAC TCA CCT CAT GTG GTC AAA ACA GCT    102
Cys Thr Gly Ile Thr Ser Ser Asn Ser Pro His Val Val Lys Thr Ala
     5                       10                      15

ACT CAA GGG GAA GTC AAT GTG ACT GGT GTG ATA CCA CTG ACA ACA ACA    150
Thr Gln Gly Glu Val Asn Val Thr Gly Val Ile Pro Leu Thr Thr Thr
20                    25                     30                 35

CCA ACA AAA TCT CAT TTT GCA AAT CTC AAA GGA ACA AAG ACC AGA GGG    198
Pro Thr Lys Ser His Phe Ala Asn Leu Lys Gly Thr Lys Thr Arg Gly
               40                      45                 50

AAA CTA TGC CCA AAC TGT CTC AAC TGC ACA GAT CTG GAT GTG GCC TTG    246
Lys Leu Cys Pro Asn Cys Leu Asn Cys Thr Asp Leu Asp Val Ala Leu
             55                     60                   65

GCG AGA CCA ATG TGT ATA GGG ACC ATA CCT TCG GCA AAA GCT TCA ATA    294
Ala Arg Pro Met Cys Ile Gly Thr Ile Pro Ser Ala Lys Ala Ser Ile
        70                      75                    80

CTC CAC GAA GTC AGA CCT GTT ACA TCC GGG TGC TTT CCT ATA ATG CAC    342

|  |  |  |  |  |  |  |  |  |  |  |  |  |  |  |  |
|---|---|---|---|---|---|---|---|---|---|---|---|---|---|---|---|
| Leu | His | Glu | Val | Arg | Pro | Val | Thr | Ser | Gly | Cys | Phe | Pro | Ile | Met | His |
|  | 85 |  |  |  | 90 |  |  |  |  | 95 |  |  |  |  |  |

| GAC | AGA | ACA | AAA | ATT | AGA | CAG | CTA | CCC | AAT | CTT | CTC | AGA | GGA | TAT | GAA | 390 |
|---|---|---|---|---|---|---|---|---|---|---|---|---|---|---|---|---|
| Asp | Arg | Thr | Lys | Ile | Arg | Gln | Leu | Pro | Asn | Leu | Leu | Arg | Gly | Tyr | Glu |  |
| 100 |  |  |  |  | 105 |  |  |  |  | 110 |  |  |  |  | 115 |  |

| AAT | ATC | AGA | TTA | TCA | ACC | CAT | AAC | GTT | ATC | AAT | GCA | GAA | AGG | GCA | CCA | 438 |
|---|---|---|---|---|---|---|---|---|---|---|---|---|---|---|---|---|
| Asn | Ile | Arg | Leu | Ser | Thr | His | Asn | Val | Ile | Asn | Ala | Glu | Arg | Ala | Pro |  |
|  |  |  |  | 120 |  |  |  |  | 125 |  |  |  |  | 130 |  |  |

| GGA | GGA | CCC | TAC | AGA | CTT | GGA | ACC | TCA | GGA | TCT | TGC | CCT | AAT | GTT | ACC | 486 |
|---|---|---|---|---|---|---|---|---|---|---|---|---|---|---|---|---|
| Gly | Gly | Pro | Tyr | Arg | Leu | Gly | Thr | Ser | Gly | Ser | Cys | Pro | Asn | Val | Thr |  |
|  |  |  | 135 |  |  |  |  | 140 |  |  |  |  | 145 |  |  |  |

| AGT | AGA | AGC | GGA | TTC | TTC | GCA | ACA | ATG | GCT | TGG | GCT | GTC | CCA | AGG | GAC | 534 |
|---|---|---|---|---|---|---|---|---|---|---|---|---|---|---|---|---|
| Ser | Arg | Ser | Gly | Phe | Phe | Ala | Thr | Met | Ala | Trp | Ala | Val | Pro | Arg | Asp |  |
|  |  | 150 |  |  |  |  | 155 |  |  |  |  | 160 |  |  |  |  |

| AAC | AAA | ACA | GCA | ACG | AAC | CCA | CTA | ACA | GTA | GAA | GTA | CCA | TAC | ATT | TGT | 582 |
|---|---|---|---|---|---|---|---|---|---|---|---|---|---|---|---|---|
| Asn | Lys | Thr | Ala | Thr | Asn | Pro | Leu | Thr | Val | Glu | Val | Pro | Tyr | Ile | Cys |  |
|  | 165 |  |  |  |  | 170 |  |  |  |  | 175 |  |  |  |  |  |

| ACA | AAA | GGA | GAA | GAC | CAA | ACT | ACT | GTT | TGG | GGG | TTC | CAT | TCT | GAT | AGC | 630 |
|---|---|---|---|---|---|---|---|---|---|---|---|---|---|---|---|---|
| Thr | Lys | Gly | Glu | Asp | Gln | Thr | Thr | Val | Trp | Gly | Phe | His | Ser | Asp | Ser |  |
| 180 |  |  |  |  | 185 |  |  |  |  | 190 |  |  |  |  | 195 |  |

| AAA | ACC | CAA | ATG | AAA | AAA | CTC | TAT | GGA | GAC | TCA | AAT | CCT | CAA | AAG | TTC | 678 |
|---|---|---|---|---|---|---|---|---|---|---|---|---|---|---|---|---|
| Lys | Thr | Gln | Met | Lys | Lys | Leu | Tyr | Gly | Asp | Ser | Asn | Pro | Gln | Lys | Phe |  |
|  |  |  |  | 200 |  |  |  |  | 205 |  |  |  |  | 210 |  |  |

| ACC | TCA | TCT | GCC | AAT | GGA | GTA | ACC | ACA | CAT | TAT | GTT | TCT | CAG | ATT | GGT | 726 |
|---|---|---|---|---|---|---|---|---|---|---|---|---|---|---|---|---|
| Thr | Ser | Ser | Ala | Asn | Gly | Val | Thr | Thr | His | Tyr | Val | Ser | Gln | Ile | Gly |  |
|  |  |  | 215 |  |  |  |  | 220 |  |  |  |  | 225 |  |  |  |

| GGC | TTC | CCA | AAT | CAA | ACA | GAA | GAC | GGA | GGG | CTA | CCA | CAA | AGC | GGC | AGA | 774 |
|---|---|---|---|---|---|---|---|---|---|---|---|---|---|---|---|---|
| Gly | Phe | Pro | Asn | Gln | Thr | Glu | Asp | Gly | Gly | Leu | Pro | Gln | Ser | Gly | Arg |  |
|  |  | 230 |  |  |  |  | 235 |  |  |  |  | 240 |  |  |  |  |

| ATT | GTT | GTT | GAT | TAC | ATG | GTG | CAA | AAA | CCT | GGG | AAA | ACA | GGA | ACA | ATT | 822 |
|---|---|---|---|---|---|---|---|---|---|---|---|---|---|---|---|---|
| Ile | Val | Val | Asp | Tyr | Met | Val | Gln | Lys | Pro | Gly | Lys | Thr | Gly | Thr | Ile |  |
|  | 245 |  |  |  |  | 250 |  |  |  |  | 255 |  |  |  |  |  |

| GTC | TAT | CAA | AGA | GGT | GTT | TTG | TTG | CCT | CAA | AAG | GTG | TGG | TGT | GCA | AGT | 870 |
|---|---|---|---|---|---|---|---|---|---|---|---|---|---|---|---|---|
| Val | Tyr | Gln | Arg | Gly | Val | Leu | Leu | Pro | Gln | Lys | Val | Trp | Cys | Ala | Ser |  |
| 260 |  |  |  |  | 265 |  |  |  |  | 270 |  |  |  |  | 275 |  |

| GGC | AGG | AGC | AAG | GTA | ATA | AAA | GGG | TCC | TTG | CCT | TTA | ATT | GGT | GAA | GCA | 918 |
|---|---|---|---|---|---|---|---|---|---|---|---|---|---|---|---|---|
| Gly | Arg | Ser | Lys | Val | Ile | Lys | Gly | Ser | Leu | Pro | Leu | Ile | Gly | Glu | Ala |  |
|  |  |  |  | 280 |  |  |  |  | 285 |  |  |  |  | 290 |  |  |

| GAT | TGC | CTT | CAC | GAA | AAA | TAC | GGT | GGA | TTA | AAC | AAA | AGC | AAG | CCT | TAC | 966 |
|---|---|---|---|---|---|---|---|---|---|---|---|---|---|---|---|---|
| Asp | Cys | Leu | His | Glu | Lys | Tyr | Gly | Gly | Leu | Asn | Lys | Ser | Lys | Pro | Tyr |  |
|  |  |  | 295 |  |  |  |  | 300 |  |  |  |  | 305 |  |  |  |

| TAC | ACA | GGA | GAA | CAT | GCA | AAA | GCC | ATA | GGA | AAT | TGC | CCA | ATA | TGG | GTG | 1014 |
|---|---|---|---|---|---|---|---|---|---|---|---|---|---|---|---|---|
| Tyr | Thr | Gly | Glu | His | Ala | Lys | Ala | Ile | Gly | Asn | Cys | Pro | Ile | Trp | Val |  |
|  |  | 310 |  |  |  |  | 315 |  |  |  |  | 320 |  |  |  |  |

| AAA | ACA | CCT | TTG | AAG | CTT | GCC | AAT | GGA | ACC | AAA | TAT | AGA | CCT | CCC | GCA | 1062 |
|---|---|---|---|---|---|---|---|---|---|---|---|---|---|---|---|---|
| Lys | Thr | Pro | Leu | Lys | Leu | Ala | Asn | Gly | Thr | Lys | Tyr | Arg | Pro | Pro | Ala |  |
|  | 325 |  |  |  |  | 330 |  |  |  |  | 335 |  |  |  |  |  |

| AAA | CTA | TTA | AAG | GAA | AGG |  |  |  |  |  |  |  |  |  |  | 1080 |
|---|---|---|---|---|---|---|---|---|---|---|---|---|---|---|---|---|
| Lys | Leu | Leu | Lys | Glu | Arg |  |  |  |  |  |  |  |  |  |  |  |
| 340 |  |  |  |  | 345 |  |  |  |  |  |  |  |  |  |  |  |

( 2 ) INFORMATION FOR SEQ ID NO:16:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| Asp | Arg | Ile | Cys | Thr | Gly | Ile | Thr | Ser | Ser | Asn | Ser | Pro | His | Val | Val |
|---|---|---|---|---|---|---|---|---|---|---|---|---|---|---|---|
| 1 |  |  |  | 5 |  |  |  |  | 10 |  |  |  |  | 15 |  |

| Lys | Thr | Ala | Thr | Gln | Gly | Glu | Val | Asn | Val | Thr | Gly | Val | Ile | Pro | Leu |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Thr | Thr | Thr | Pro | Thr | Lys | Ser | His | Phe | Ala | Asn | Leu | Lys | Gly | Thr | Lys |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Thr | Arg | Gly | Lys | Leu | Cys | Pro | Asn | Cys | Leu | Asn | Cys | Thr | Asp | Leu | Asp |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Val | Ala | Leu | Ala | Arg | Pro | Met | Cys | Ile | Gly | Thr | Ile | Pro | Ser | Ala | Lys |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ala | Ser | Ile | Leu | His | Glu | Val | Arg | Pro | Val | Thr | Ser | Gly | Cys | Phe | Pro |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Ile | Met | His | Asp | Arg | Thr | Lys | Ile | Arg | Gln | Leu | Pro | Asn | Leu | Leu | Arg |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Gly | Tyr | Glu | Asn | Ile | Arg | Leu | Ser | Thr | His | Asn | Val | Ile | Asn | Ala | Glu |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Arg | Ala | Pro | Gly | Gly | Pro | Tyr | Arg | Leu | Gly | Thr | Ser | Gly | Ser | Cys | Pro |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Asn | Val | Thr | Ser | Arg | Ser | Gly | Phe | Phe | Ala | Thr | Met | Ala | Trp | Ala | Val |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Pro | Arg | Asp | Asn | Lys | Thr | Ala | Thr | Asn | Pro | Leu | Thr | Val | Glu | Val | Pro |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Tyr | Ile | Cys | Thr | Lys | Gly | Glu | Asp | Gln | Thr | Thr | Val | Trp | Gly | Phe | His |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Ser | Asp | Ser | Lys | Thr | Gln | Met | Lys | Lys | Leu | Tyr | Gly | Asp | Ser | Asn | Pro |
|-----|-----|-----|-----|-----|-----|-----|-----|-----|-----|-----|-----|-----|-----|-----|-----|
|     |     |     | 195 |     |     |     |     | 200 |     |     |     |     | 205 |     |     |

| Gln | Lys | Phe | Thr | Ser | Ser | Ala | Asn | Gly | Val | Thr | Thr | His | Tyr | Val | Ser |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Gln | Ile | Gly | Gly | Phe | Pro | Asn | Gln | Thr | Glu | Asp | Gly | Gly | Leu | Pro | Gln |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Ser | Gly | Arg | Ile | Val | Val | Asp | Tyr | Met | Val | Gln | Lys | Pro | Gly | Lys | Thr |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Gly | Thr | Ile | Val | Tyr | Gln | Arg | Gly | Val | Leu | Leu | Pro | Gln | Lys | Val | Trp |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Cys | Ala | Ser | Gly | Arg | Ser | Lys | Val | Ile | Lys | Gly | Ser | Leu | Pro | Leu | Ile |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Gly | Glu | Ala | Asp | Cys | Leu | His | Glu | Lys | Tyr | Gly | Gly | Leu | Asn | Lys | Ser |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Lys | Pro | Tyr | Tyr | Thr | Gly | Glu | His | Ala | Lys | Ala | Ile | Gly | Asn | Cys | Pro |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Ile | Trp | Val | Lys | Thr | Pro | Leu | Lys | Leu | Ala | Asn | Gly | Thr | Lys | Tyr | Arg |
|-----|-----|-----|-----|-----|-----|-----|-----|-----|-----|-----|-----|-----|-----|-----|-----|
|     |     |     |     | 325 |     |     |     |     | 330 |     |     |     |     | 335 |     |

| Pro | Pro | Ala | Lys | Leu | Leu | Lys | Glu | Arg |
|-----|-----|-----|-----|-----|-----|-----|-----|-----|
|     |     |     | 340 |     |     |     |     | 345 |

( 2 ) INFORMATION FOR SEQ ID NO:17:

( i ) SEQUENCE CHARACTERISTICS:
        ( A ) LENGTH: 1080 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 46..1080
        ( D ) OTHER INFORMATION: /label=PN90

( x i ) SEQUENCE DESCRIPTION: SEQ ID NO:17:

ATGAAGGCAA TAATTGTACT ACTCATGGTA GTAACATCCA ACGCA GAT CGA ATC     54

|   |   |   |   |   |   |   |   |   | Asp | Arg | Ile |   |   |   |   |   |
|---|---|---|---|---|---|---|---|---|-----|-----|-----|---|---|---|---|---|
|   |   |   |   |   |   |   |   |   |     | 1   |     |   |   |   |   |   |

```
TGC ACT GGG ATA ACA TCT TCA AAC TCA CCT CAT GTG GTC AAA ACA GCT      102
Cys Thr Gly Ile Thr Ser Ser Asn Ser Pro His Val Val Lys Thr Ala
      5               10                  15

ACT CAA GGG GAA GTC AAT GTG ACT GGT GTG ATA CCA CTG ACA ACA ACA      150
Thr Gln Gly Glu Val Asn Val Thr Gly Val Ile Pro Leu Thr Thr Thr
 20              25                  30                      35

CCA ACA AAA TCT CAT TTT GCA AAT CTA AAA GGA ACA AAG ACC AGA GGG      198
Pro Thr Lys Ser His Phe Ala Asn Leu Lys Gly Thr Lys Thr Arg Gly
             40                  45                      50

AAA CTA TGC CCA AAC TGT CTC AAC TGC ACA GAT CTG GAT GTG GCC TTG      246
Lys Leu Cys Pro Asn Cys Leu Asn Cys Thr Asp Leu Asp Val Ala Leu
         55                  60                      65

GCG AGA CCA ATG TGT GTG GGG ACC ACA CCT TCG GCA AAA GCT TCA ATA      294
Ala Arg Pro Met Cys Val Gly Thr Thr Pro Ser Ala Lys Ala Ser Ile
     70                  75                      80

CTC CAC GAA GTC AGA CCT GTT ACA TCC GGG TGC TTT CCT ATA ATG CAC      342
Leu His Glu Val Arg Pro Val Thr Ser Gly Cys Phe Pro Ile Met His
 85                  90                      95

GAC AGA ACA AAA ATC AGA CAG CTA CCC AAT CTT CTC AGA GGA TAT GAA      390
Asp Arg Thr Lys Ile Arg Gln Leu Pro Asn Leu Leu Arg Gly Tyr Glu
100             105                 110                     115

AAT ATC AGA TTA TCA ACC CAA AAC GTT ATC AAT GCA GAA AGA GCA CCA      438
Asn Ile Arg Leu Ser Thr Gln Asn Val Ile Asn Ala Glu Arg Ala Pro
                120                 125                     130

GGA GGA CCC TAC AGA CTT GGA ACC TCA GGA TCT TGC CCT AAC GTT ACC      486
Gly Gly Pro Tyr Arg Leu Gly Thr Ser Gly Ser Cys Pro Asn Val Thr
            135                 140                     145

AGT AGA GAC GGA TTC TTC GCA ACA ATG GCT TGG GCT GTC CCA AGG GAC      534
Ser Arg Asp Gly Phe Phe Ala Thr Met Ala Trp Ala Val Pro Arg Asp
        150                 155                     160

AAC AAA ACA GCA ACG AAT CCA CTA ACA GTA GAA GTA CCA TAC ATT TGT      582
Asn Lys Thr Ala Thr Asn Pro Leu Thr Val Glu Val Pro Tyr Ile Cys
    165                 170                     175

ACA AAA GGA GAA GAC CAA ACT ACT GTT TGG GGG TTC CAT TCT GAT AGC      630
Thr Lys Gly Glu Asp Gln Thr Thr Val Trp Gly Phe His Ser Asp Ser
180                 185                     190                 195

AAA ACC CAA ATG AAA AAC CTC TAT GGA GAC TCA AAT CCT CAA AAG TTC      678
Asn Thr Gln Met Lys Asn Leu Tyr Gly Asp Ser Asn Pro Gln Lys Phe
                200                 205                     210

ACC TCA TCT GCC AAT GGA GTA ACC ACA CAT TAT GTT TCT CAG ATT GGT      726
Thr Ser Ser Ala Asn Gly Val Thr Thr His Tyr Val Ser Gln Ile Gly
            215                 220                     225

GGC TTC CCA AAT CAA ACA GAA GAC GGA GGG CTA CCA CAA AGC GGC AGA      774
Gly Phe Pro Asn Gln Thr Glu Asp Gly Gly Leu Pro Gln Ser Gly Arg
        230                 235                     240

ATT GTT GTT GAT TAC ATG GTG CAA AAA CCT GGG AAA ACA GGA ACA ATT      822
Ile Val Val Asp Tyr Met Val Gln Lys Pro Gly Lys Thr Gly Thr Ile
    245                 250                     255

GTC TAT CAA AGA GGT GTT TTG TTG CCT CAA AAG GTG TGG TGC GCA AGT      870
Val Tyr Gln Arg Gly Val Leu Leu Pro Gln Lys Val Trp Cys Ala Ser
260                 265                     270                 275

GGC AGG AGC AAG GTA ATA AAA GGG TCC TTG CCT TTA ATT GGT GAA GCA      918
Gly Arg Ser Lys Val Ile Lys Gly Ser Leu Pro Leu Ile Gly Glu Ala
                280                 285                     290

GAT TGC CTT CAC GCA AAA TAC GGT GGA TTA AAC AAA AGC AAG CCT TAC      966
Asp Cys Leu His Ala Lys Tyr Gly Gly Leu Asn Lys Ser Lys Pro Tyr
            295                 300                     305

TAC ACA GGA GAA CAT GCA AAA GCC ATA GGA AAT TGC CCA ATA TGG GTA     1014
Tyr Thr Gly Glu His Ala Lys Ala Ile Gly Asn Cys Pro Ile Trp Val
```

|   | 310 |   |   |   | 315 |   |   |   | 320 |   |   |   |   |
|---|---|---|---|---|---|---|---|---|---|---|---|---|---|
| AAA | ACA | CCT | TTG | AAG | CTT | GCC | AAT | GGA | ACC | AAA | TAT | AGA | CCT | CCT | GCA | 1062 |
| Lys | Thr | Pro | Leu | Lys | Leu | Ala | Asn | Gly | Thr | Lys | Tyr | Arg | Pro | Pro | Ala |   |
|   | 325 |   |   |   | 330 |   |   |   | 335 |   |   |   |   |   |   |   |
| AAA | CTA | TTA | AAG | GAA | AGG |   |   |   |   |   |   |   |   |   |   | 1080 |
| Lys | Leu | Leu | Lys | Glu | Arg |   |   |   |   |   |   |   |   |   |   |   |
| 340 |   |   |   |   | 345 |   |   |   |   |   |   |   |   |   |   |   |

( 2 ) INFORMATION FOR SEQ ID NO:18:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| Asp | Arg | Ile | Cys | Thr | Gly | Ile | Thr | Ser | Ser | Asn | Ser | Pro | His | Val | Val |
|---|---|---|---|---|---|---|---|---|---|---|---|---|---|---|---|
| 1 |   |   |   | 5 |   |   |   |   | 10 |   |   |   |   | 15 |   |
| Lys | Thr | Ala | Thr | Gln | Gly | Glu | Val | Asn | Val | Thr | Gly | Val | Ile | Pro | Leu |
|   |   |   | 20 |   |   |   |   | 25 |   |   |   |   | 30 |   |   |
| Thr | Thr | Thr | Pro | Thr | Lys | Ser | His | Phe | Ala | Asn | Leu | Lys | Gly | Thr | Lys |
|   |   | 35 |   |   |   |   | 40 |   |   |   |   | 45 |   |   |   |
| Thr | Arg | Gly | Lys | Leu | Cys | Pro | Asn | Cys | Leu | Asn | Cys | Thr | Asp | Leu | Asp |
|   | 50 |   |   |   |   | 55 |   |   |   |   | 60 |   |   |   |   |
| Val | Ala | Leu | Ala | Arg | Pro | Met | Cys | Val | Gly | Thr | Thr | Pro | Ser | Ala | Lys |
| 65 |   |   |   |   | 70 |   |   |   |   | 75 |   |   |   |   | 80 |
| Ala | Ser | Ile | Leu | His | Glu | Val | Arg | Pro | Val | Thr | Ser | Gly | Cys | Phe | Pro |
|   |   |   |   | 85 |   |   |   |   | 90 |   |   |   |   | 95 |   |
| Ile | Met | His | Asp | Arg | Thr | Lys | Ile | Arg | Gln | Leu | Pro | Asn | Leu | Leu | Arg |
|   |   |   | 100 |   |   |   |   | 105 |   |   |   |   | 110 |   |   |
| Gly | Tyr | Glu | Asn | Ile | Arg | Leu | Ser | Thr | Gln | Asn | Val | Ile | Asn | Ala | Glu |
|   |   |   | 115 |   |   |   | 120 |   |   |   |   | 125 |   |   |   |
| Arg | Ala | Pro | Gly | Gly | Pro | Tyr | Arg | Leu | Gly | Thr | Ser | Gly | Ser | Cys | Pro |
|   |   | 130 |   |   |   | 135 |   |   |   |   | 140 |   |   |   |   |
| Asn | Val | Thr | Ser | Arg | Asp | Gly | Phe | Phe | Ala | Thr | Met | Ala | Trp | Ala | Val |
| 145 |   |   |   |   | 150 |   |   |   |   | 155 |   |   |   |   | 160 |
| Pro | Arg | Asp | Asn | Lys | Thr | Ala | Thr | Asn | Pro | Leu | Thr | Val | Glu | Val | Pro |
|   |   |   |   | 165 |   |   |   |   | 170 |   |   |   |   | 175 |   |
| Tyr | Ile | Cys | Thr | Lys | Gly | Glu | Asp | Gln | Thr | Thr | Val | Trp | Gly | Phe | His |
|   |   |   | 180 |   |   |   |   | 185 |   |   |   |   | 190 |   |   |
| Ser | Asp | Ser | Asn | Thr | Gln | Met | Lys | Asn | Leu | Tyr | Gly | Asp | Ser | Asn | Pro |
|   |   | 195 |   |   |   |   | 200 |   |   |   |   | 205 |   |   |   |
| Gln | Lys | Phe | Thr | Ser | Ser | Ala | Asn | Gly | Val | Thr | Thr | His | Tyr | Val | Ser |
|   | 210 |   |   |   |   | 215 |   |   |   |   | 220 |   |   |   |   |
| Gln | Ile | Gly | Gly | Phe | Pro | Asn | Gln | Thr | Glu | Asp | Gly | Gly | Leu | Pro | Gln |
| 225 |   |   |   |   | 230 |   |   |   |   | 235 |   |   |   |   | 240 |
| Ser | Gly | Arg | Ile | Val | Val | Asp | Tyr | Met | Val | Gln | Lys | Pro | Gly | Lys | Thr |
|   |   |   |   | 245 |   |   |   |   | 250 |   |   |   |   | 255 |   |
| Gly | Thr | Ile | Val | Tyr | Gln | Arg | Gly | Val | Leu | Leu | Pro | Gln | Lys | Val | Trp |
|   |   |   | 260 |   |   |   |   | 265 |   |   |   |   | 270 |   |   |
| Cys | Ala | Ser | Gly | Arg | Ser | Lys | Val | Ile | Lys | Gly | Ser | Leu | Pro | Leu | Ile |
|   |   | 275 |   |   |   |   | 280 |   |   |   |   | 285 |   |   |   |
| Gly | Glu | Ala | Asp | Cys | Leu | His | Ala | Lys | Tyr | Gly | Gly | Leu | Asn | Lys | Ser |
|   | 290 |   |   |   |   | 295 |   |   |   |   | 300 |   |   |   |   |
| Lys | Pro | Tyr | Tyr | Thr | Gly | Glu | His | Ala | Lys | Ala | Ile | Gly | Asn | Cys | Pro |
| 305 |   |   |   |   | 310 |   |   |   |   | 315 |   |   |   |   | 320 |

| | | | | | | | | | | | | | | | |
|---|---|---|---|---|---|---|---|---|---|---|---|---|---|---|---|
|Ile|Trp|Val|Lys|Thr<br>325|Pro|Leu|Lys|Leu|Ala<br>330|Asn|Gly|Thr|Lys|Tyr<br>335|Arg|
|Pro|Pro|Ala|Lys<br>340|Leu|Leu|Lys|Glu|Arg<br>345| | | | | | | |

(2) INFORMATION FOR SEQ ID NO:19:

(i) SEQUENCE CHARACTERISTICS:
        (A) LENGTH: 1080 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 46..1080
        (D) OTHER INFORMATION: /label=NY90

(xi) SEQUENCE DESCRIPTION: SEQ ID NO:19:

```
ATGAAGGCAA TAATTGTACT ACTCATGGTA GTAACATCCA ACGCA GAT CGA ATC           54
                                                 Asp Arg Ile
                                                  1
```

| | | | | | | | | | | | | | | | |
|---|---|---|---|---|---|---|---|---|---|---|---|---|---|---|---|
|TGC|ACT|GGG|ATA|ACA|TCT|TCA|AAC|TCA|CCT|CAT|GTG|GTC|AAA|ACA|GCT|
|Cys|Thr<br>5|Gly|Ile|Thr|Ser|Ser<br>10|Asn|Ser|Pro|His|Val<br>15|Val|Lys|Thr|Ala|

102

| | | | | | | | | | | | | | | | |
|---|---|---|---|---|---|---|---|---|---|---|---|---|---|---|---|
|ACT|CAA|GGG|GAA|GTC|AAT|GTG|ACT|GGT|GTG|ATA|CCA|CTG|ACA|ACA|ACA|
|Thr<br>20|Gln|Gly|Glu|Val|Asn<br>25|Val|Thr|Gly|Val|Ile<br>30|Pro|Leu|Thr|Thr|Thr<br>35|

150

| | | | | | | | | | | | | | | | |
|---|---|---|---|---|---|---|---|---|---|---|---|---|---|---|---|
|CCA|ACA|AAA|TCT|CAT|TTT|GCA|AAT|CTC|AAA|GGA|ACA|AAG|ACC|AGA|GGG|
|Pro|Thr|Lys|Ser|His<br>40|Phe|Ala|Asn|Leu|Lys<br>45|Gly|Thr|Lys|Thr|Arg|Gly<br>50|

198

| | | | | | | | | | | | | | | | |
|---|---|---|---|---|---|---|---|---|---|---|---|---|---|---|---|
|AAA|CTA|TGC|CCA|AAC|TGT|CTC|AAC|TGC|ACA|GAT|CTG|GAT|GTG|GCC|TTG|
|Lys|Leu|Cys|Pro<br>55|Asn|Cys|Leu|Asn|Cys<br>60|Thr|Asp|Leu|Asp|Val<br>65|Ala|Leu|

246

| | | | | | | | | | | | | | | | |
|---|---|---|---|---|---|---|---|---|---|---|---|---|---|---|---|
|GCG|AGA|CCA|ATG|TGT|ATA|GGG|ACC|ATA|CCT|TCG|GCA|AAA|GCT|TCA|ATA|
|Ala|Arg|Pro<br>70|Met|Cys|Ile|Gly|Thr<br>75|Ile|Pro|Ser|Ala|Lys<br>80|Ala|Ser|Ile|

294

| | | | | | | | | | | | | | | | |
|---|---|---|---|---|---|---|---|---|---|---|---|---|---|---|---|
|CTC|CAC|GAA|GTC|AGA|CCT|GTT|ACA|TCC|GGG|TGC|TTT|CCT|ATA|ATG|CAC|
|Leu|His<br>85|Glu|Val|Arg|Pro|Val<br>90|Thr|Ser|Gly|Cys|Phe<br>95|Pro|Ile|Met|His|

342

| | | | | | | | | | | | | | | | |
|---|---|---|---|---|---|---|---|---|---|---|---|---|---|---|---|
|GAC|AGA|ACA|AAA|ATC|AGA|CAG|CTA|CCC|AAT|CTT|CTC|AGA|GGA|TAT|GAA|
|Asp|Arg|Thr|Lys<br>100|Ile|Arg|Gln|Leu|Pro<br>105|Asn|Leu|Leu|Arg|Gly<br>110|Tyr|Glu<br>115|

390

| | | | | | | | | | | | | | | | |
|---|---|---|---|---|---|---|---|---|---|---|---|---|---|---|---|
|AAT|ATC|AGA|TTA|TCA|ACC|CAT|AAC|GTT|ATC|AAT|GCA|GAA|AGG|GCA|CCA|
|Asn|Ile|Arg|Leu|Ser<br>120|Thr|His|Asn|Val|Ile<br>125|Asn|Ala|Glu|Arg|Ala<br>130|Pro|

438

| | | | | | | | | | | | | | | | |
|---|---|---|---|---|---|---|---|---|---|---|---|---|---|---|---|
|GGA|GGA|CCC|TAC|AGA|CTT|GGA|ACC|TCA|GGA|TCT|TGC|CCT|AAC|GTT|ACC|
|Gly|Gly|Pro|Tyr<br>135|Arg|Leu|Gly|Thr|Ser<br>140|Gly|Ser|Cys|Pro|Asn<br>145|Val|Thr|

486

| | | | | | | | | | | | | | | | |
|---|---|---|---|---|---|---|---|---|---|---|---|---|---|---|---|
|AGT|AGA|AGC|GGA|TTC|TTC|GCA|ACA|ATG|GCT|TGG|GCT|GTC|CCA|AGG|GAC|
|Ser|Arg|Ser<br>150|Gly|Phe|Phe|Ala|Thr<br>155|Met|Ala|Trp|Ala|Val<br>160|Pro|Arg|Asp|

534

| | | | | | | | | | | | | | | | |
|---|---|---|---|---|---|---|---|---|---|---|---|---|---|---|---|
|AAC|AAA|ACA|GCA|ACG|AAC|CCA|CTA|ACA|GTA|GAA|GTA|CCA|TAC|ATT|TGT|
|Asn|Lys<br>165|Thr|Ala|Thr|Asn|Pro<br>170|Leu|Thr|Val|Glu|Val<br>175|Pro|Tyr|Ile|Cys|

582

| | | | | | | | | | | | | | | | |
|---|---|---|---|---|---|---|---|---|---|---|---|---|---|---|---|
|ACA|AAA|GGA|GAA|GAC|CAA|ACT|ACT|GTT|TGG|GGG|TTC|CAT|TCT|GAT|AAC|
|Thr|Lys|Gly|Glu|Asp<br>180|Gln|Thr|Thr|Val|Trp<br>185|Gly|Phe|His|Ser|Asp<br>190|Asn<br>195|

630

| | | | | | | | | | | | | | | | |
|---|---|---|---|---|---|---|---|---|---|---|---|---|---|---|---|
|AAA|ACC|CAA|ATG|AAA|AAC|CTC|TAT|GGA|GAC|TCA|AAT|CCT|CAA|AAG|TTC|
|Lys|Thr|Gln|Met|Lys<br>200|Asn|Leu|Tyr|Gly|Asp<br>205|Ser|Asn|Pro|Gln|Lys<br>210|Phe|

678

| | | | | | | | | | | | | | | | |
|---|---|---|---|---|---|---|---|---|---|---|---|---|---|---|---|
|ACC|TCA|TCT|GCC|AAT|GGA|GTA|ACC|ACA|CAT|TAT|GTT|TCT|CAG|ATT|GGT|

726

|  |  |  |  |  |  |  |  |  |  |  |  |  |  |  |  |
|---|---|---|---|---|---|---|---|---|---|---|---|---|---|---|---|
| Thr | Ser | Ser | Ala<br>215 | Asn | Gly | Val | Thr | Thr<br>220 | His | Tyr | Val | Ser | Gln<br>225 | Ile | Gly |

| GGC | TTC | CCA | AAT | CAA | ACA | GAA | GAC | GGA | GGG | CTA | CCA | CAA | AGC | GGC | AGA | 774 |
|---|---|---|---|---|---|---|---|---|---|---|---|---|---|---|---|---|
| Gly | Phe | Pro<br>230 | Asn | Gln | Thr | Glu | Asp<br>235 | Gly | Gly | Leu | Pro | Gln<br>240 | Ser | Gly | Arg | |

| ATT | GTT | GTT | GAT | TAC | ATG | GTG | CAA | AAA | CCT | GGG | AAA | ACA | GGA | ACG | ATT | 822 |
|---|---|---|---|---|---|---|---|---|---|---|---|---|---|---|---|---|
| Ile | Val<br>245 | Val | Asp | Tyr | Met | Val<br>250 | Gln | Lys | Pro | Gly | Lys<br>255 | Thr | Gly | Thr | Ile | |

| GTC | TAT | CAA | AGA | GGT | GTT | TTG | TTG | CCT | CAA | AAG | GTG | TGG | TGT | GCA | AGT | 870 |
|---|---|---|---|---|---|---|---|---|---|---|---|---|---|---|---|---|
| Val<br>260 | Tyr | Gln | Arg | Gly | Val<br>265 | Leu | Leu | Pro | Gln | Lys<br>270 | Val | Trp | Cys | Ala | Ser<br>275 | |

| GGC | AGG | AGC | AAG | GTA | ATA | AAA | GGG | TCC | TTG | CCT | TTA | ATT | GGT | GAA | GCA | 918 |
|---|---|---|---|---|---|---|---|---|---|---|---|---|---|---|---|---|
| Gly | Arg | Ser | Lys | Val<br>280 | Ile | Lys | Gly | Ser | Leu<br>285 | Pro | Leu | Ile | Gly | Glu<br>290 | Ala | |

| GAT | TGC | CTT | CAC | GAA | AAA | TAC | GGT | GGA | TTA | AAC | AAA | AGC | AAG | CCT | TAC | 966 |
|---|---|---|---|---|---|---|---|---|---|---|---|---|---|---|---|---|
| Asp | Cys | Leu | His<br>295 | Glu | Lys | Tyr | Gly | Gly<br>300 | Leu | Asn | Lys | Ser | Lys<br>305 | Pro | Tyr | |

| TAT | ACA | GGA | GAA | CAT | GCA | AAA | GCC | ATA | GGA | AAT | TGC | CCA | ATA | TGG | GTG | 1014 |
|---|---|---|---|---|---|---|---|---|---|---|---|---|---|---|---|---|
| Tyr | Thr | Gly<br>310 | Glu | His | Ala | Lys | Ala<br>315 | Ile | Gly | Asn | Cys | Pro<br>320 | Ile | Trp | Val | |

| AAA | ACA | CCT | TTG | AAG | CTT | GCC | AAT | GGA | ACC | AAA | TAC | AGA | CCT | CCC | GCA | 1062 |
|---|---|---|---|---|---|---|---|---|---|---|---|---|---|---|---|---|
| Lys | Thr<br>325 | Pro | Leu | Lys | Leu | Ala<br>330 | Asn | Gly | Thr | Lys | Tyr<br>335 | Arg | Pro | Pro | Ala | |

| AAA | CTA | TTA | AAG | GAA | AGG |  |  |  |  |  |  |  |  |  |  | 1080 |
|---|---|---|---|---|---|---|---|---|---|---|---|---|---|---|---|---|
| Lys | Leu | Leu | Lys | Glu | Arg<br>345 |  |  |  |  |  |  |  |  |  |  | |
| 340 | | | | | | | | | | | | | | | | |

( 2 ) INFORMATION FOR SEQ ID NO:20:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

|  |  |  |  |  |  |  |  |  |  |  |  |  |  |  |
|---|---|---|---|---|---|---|---|---|---|---|---|---|---|---|
| Asp<br>1 | Arg | Ile | Cys | Thr<br>5 | Gly | Ile | Thr | Ser | Ser<br>10 | Asn | Ser | Pro | His | Val<br>15 | Val |

| Lys | Thr | Ala | Thr<br>20 | Gln | Gly | Glu | Val | Asn<br>25 | Val | Thr | Gly | Val | Ile<br>30 | Pro | Leu |
|---|---|---|---|---|---|---|---|---|---|---|---|---|---|---|---|

| Thr | Thr | Thr<br>35 | Pro | Thr | Lys | Ser | His<br>40 | Phe | Ala | Asn | Leu | Lys<br>45 | Gly | Thr | Lys |
|---|---|---|---|---|---|---|---|---|---|---|---|---|---|---|---|

| Thr | Arg<br>50 | Gly | Lys | Leu | Cys | Pro<br>55 | Asn | Cys | Leu | Asn | Cys<br>60 | Thr | Asp | Leu | Asp |
|---|---|---|---|---|---|---|---|---|---|---|---|---|---|---|---|

| Val<br>65 | Ala | Leu | Ala | Arg | Pro<br>70 | Met | Cys | Ile | Gly | Thr<br>75 | Ile | Pro | Ser | Ala | Lys<br>80 |
|---|---|---|---|---|---|---|---|---|---|---|---|---|---|---|---|

| Ala | Ser | Ile | Leu | His<br>85 | Glu | Val | Arg | Pro | Val<br>90 | Thr | Ser | Gly | Cys | Phe<br>95 | Pro |
|---|---|---|---|---|---|---|---|---|---|---|---|---|---|---|---|

| Ile | Met | His | Asp<br>100 | Arg | Thr | Lys | Ile | Arg<br>105 | Gln | Leu | Pro | Asn | Leu<br>110 | Leu | Arg |
|---|---|---|---|---|---|---|---|---|---|---|---|---|---|---|---|

| Gly | Tyr | Glu<br>115 | Asn | Ile | Arg | Leu | Ser<br>120 | Thr | His | Asn | Val | Ile<br>125 | Asn | Ala | Glu |
|---|---|---|---|---|---|---|---|---|---|---|---|---|---|---|---|

| Arg | Ala<br>130 | Pro | Gly | Gly | Pro | Tyr<br>135 | Arg | Leu | Gly | Thr | Ser<br>140 | Gly | Ser | Cys | Pro |
|---|---|---|---|---|---|---|---|---|---|---|---|---|---|---|---|

| Asn<br>145 | Val | Thr | Ser | Arg | Ser<br>150 | Gly | Phe | Phe | Ala | Thr<br>155 | Met | Ala | Trp | Ala | Val<br>160 |
|---|---|---|---|---|---|---|---|---|---|---|---|---|---|---|---|

| Pro | Arg | Asp | Asn | Lys<br>165 | Thr | Ala | Thr | Asn | Pro<br>170 | Leu | Thr | Val | Glu | Val<br>175 | Pro |
|---|---|---|---|---|---|---|---|---|---|---|---|---|---|---|---|

| Tyr | Ile | Cys | Thr<br>180 | Lys | Gly | Glu | Asp | Gln<br>185 | Thr | Thr | Val | Trp | Gly<br>190 | Phe | His |
|---|---|---|---|---|---|---|---|---|---|---|---|---|---|---|---|

```
Ser Asp Asn Lys Thr Gln Met Lys Asn Leu Tyr Gly Asp Ser Asn Pro
        195                 200                 205
Gln Lys Phe Thr Ser Ser Ala Asn Gly Val Thr Thr His Tyr Val Ser
        210                 215                 220
Gln Ile Gly Gly Phe Pro Asn Gln Thr Glu Asp Gly Gly Leu Pro Gln
225                     230                 235                 240
Ser Gly Arg Ile Val Val Asp Tyr Met Val Gln Lys Pro Gly Lys Thr
                245                 250                 255
Gly Thr Ile Val Tyr Gln Arg Gly Val Leu Leu Pro Gln Lys Val Trp
                260                 265                 270
Cys Ala Ser Gly Arg Ser Lys Val Ile Lys Gly Ser Leu Pro Leu Ile
            275                 280                 285
Gly Glu Ala Asp Cys Leu His Glu Lys Tyr Gly Gly Leu Asn Lys Ser
        290                 295                 300
Lys Pro Tyr Tyr Thr Gly Glu His Ala Lys Ala Ile Gly Asn Cys Pro
305                     310                 315                 320
Ile Trp Val Lys Thr Pro Leu Lys Leu Ala Asn Gly Thr Lys Tyr Arg
                325                 330                 335
Pro Pro Ala Lys Leu Leu Lys Glu Arg
            340                 345
```

( 2 ) INFORMATION FOR SEQ ID NO:21:

( i ) SEQUENCE CHARACTERISTICS:
        ( A ) LENGTH: 1080 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 46..1080
        ( D ) OTHER INFORMATION: /label=TX90

( x i ) SEQUENCE DESCRIPTION: SEQ ID NO:21:

```
ATGAAGGCAA TAATTGTACT ACTCATGGTA GTAACATCCA ACGCA GAT CGA ATC         54
                                                 Asp Arg Ile
                                                  1

TGC ACT GGG ATA ACA TCT TCA AAC TCA CCT CAT GTG GTC AAA ACA GCT    102
Cys Thr Gly Ile Thr Ser Ser Asn Ser Pro His Val Val Lys Thr Ala
         5                  10                  15

ACT CAA GGG GAA GTC AAT GTG ACT GGT GTG ATA CCA CTG ACA ACA ACA    150
Thr Gln Gly Glu Val Asn Val Thr Gly Val Ile Pro Leu Thr Thr Thr
 20                  25                  30                   35

CCA ACA AAA TCT CAT TTT GCA AAT CTC AAA GGA ACA AAG ACC AGA GGG    198
Pro Thr Lys Ser His Phe Ala Asn Leu Lys Gly Thr Lys Thr Arg Gly
                 40                  45                  50

AAA CTA TGC CCA AAC TGT CTC AAC TGC ACA GAT CTG GAT GTG GCC TTG    246
Lys Leu Cys Pro Asn Cys Leu Asn Cys Thr Asp Leu Asp Val Ala Leu
             55                  60                  65

GCG AGA CCA ATG TGT ATA GGG ACC ATA CCT TCG GCA AAA GCT TCA ATA    294
Ala Arg Pro Met Cys Ile Gly Thr Ile Pro Ser Ala Lys Ala Ser Ile
         70                  75                  80

CTC CAC GAA GTC AGG CCT GTT ACA TCC AGG TGC TTT CCT ATA ATG CAC    342
Leu His Glu Val Arg Pro Val Thr Ser Arg Cys Phe Pro Ile Met His
     85                   90                  95

GAC AGA ACA AAA ATC AGA CAG CTA CCC AAT CTT CTC AGA GGA TAT GAA    390
Asp Arg Thr Lys Ile Arg Gln Leu Pro Asn Leu Leu Arg Gly Tyr Glu
100                  105                 110                 115
```

| AAT<br>Asn | ATC<br>Ile | AGA<br>Arg<br>120 | TTA<br>Leu | TCA<br>Ser | ACC<br>Thr | CAT<br>His | AAC<br>Asn<br>125 | GTT<br>Val | ATC<br>Ile | AAC<br>Asn | GCA<br>Ala | GAA<br>Glu<br>130 | AGG<br>Arg | GCA<br>Ala | CCA<br>Pro | 438 |
| --- | --- | --- | --- | --- | --- | --- | --- | --- | --- | --- | --- | --- | --- | --- | --- | --- |
| GGA<br>Gly | GGA<br>Gly | CCC<br>Pro<br>135 | TAC<br>Tyr | AGA<br>Arg | CTT<br>Leu | GGA<br>Gly | ACC<br>Thr<br>140 | TCA<br>Ser | GGA<br>Gly | TCT<br>Ser | TGC<br>Cys | CCT<br>Pro<br>145 | AAC<br>Asn | GTT<br>Val | ACC<br>Thr | 486 |
| AGT<br>Ser | AGA<br>Arg | AGC<br>Ser<br>150 | GGA<br>Gly | TTC<br>Phe | TTC<br>Phe | GCA<br>Ala | ACA<br>Thr<br>155 | ATG<br>Met | GCT<br>Ala | TGG<br>Trp | GCT<br>Ala | GTC<br>Val<br>160 | CCA<br>Pro | AGG<br>Arg | GAC<br>Asp | 534 |
| AAC<br>Asn | AAA<br>Lys<br>165 | ACA<br>Thr | GCA<br>Ala | ACG<br>Thr | AAC<br>Asn | CCA<br>Pro<br>170 | CTA<br>Leu | ACA<br>Thr | GTA<br>Val | GAA<br>Glu | GTA<br>Val<br>175 | CCA<br>Pro | TAC<br>Tyr | ATT<br>Ile | TGT<br>Cys | 582 |
| ACA<br>Thr<br>180 | AAA<br>Lys | GGA<br>Gly | GAA<br>Glu | GAC<br>Asp | CAA<br>Gln<br>185 | ACT<br>Thr | ACT<br>Thr | GTT<br>Val | TGG<br>Trp | GGG<br>Gly<br>190 | TTC<br>Phe | CAT<br>His | TCT<br>Ser | GAT<br>Asp | AAC<br>Asn<br>195 | 630 |
| AAA<br>Lys | ACC<br>Thr | CAA<br>Gln | ATG<br>Met | AAA<br>Lys<br>200 | AAC<br>Asn | CTC<br>Leu | TAT<br>Tyr | GGA<br>Gly | GAC<br>Asp<br>205 | TCA<br>Ser | AAT<br>Asn | CCT<br>Pro | CAA<br>Gln | AAA<br>Lys<br>210 | TTC<br>Phe | 678 |
| ACC<br>Thr | TCA<br>Ser | TCT<br>Ser | GCC<br>Ala<br>215 | AAT<br>Asn | GGA<br>Gly | GTA<br>Val | ACC<br>Thr | ACA<br>Thr<br>220 | CAT<br>His | TAT<br>Tyr | GTT<br>Val | TCT<br>Ser | CAG<br>Gln<br>225 | ATT<br>Ile | GGT<br>Gly | 726 |
| GGC<br>Gly | TTC<br>Phe | CCA<br>Pro<br>230 | AAT<br>Asn | CAA<br>Gln | ACA<br>Thr | GAA<br>Glu | GAC<br>Asp<br>235 | GGA<br>Gly | GGG<br>Gly | CTA<br>Leu | CCA<br>Pro | CAA<br>Gln<br>240 | AGC<br>Ser | GGC<br>Gly | AGA<br>Arg | 774 |
| ATT<br>Ile | GTT<br>Val<br>245 | GTT<br>Val | GAT<br>Asp | TAC<br>Tyr | ATG<br>Met | GTG<br>Val<br>250 | CAA<br>Gln | AAA<br>Lys | CCT<br>Pro | GGG<br>Gly | AAA<br>Lys<br>255 | ACA<br>Thr | GGA<br>Gly | ACA<br>Thr | ATT<br>Ile | 822 |
| GTC<br>Val<br>260 | TAT<br>Tyr | CAA<br>Gln | AGA<br>Arg | GGT<br>Gly | GTT<br>Val<br>265 | TTG<br>Leu | TTA<br>Leu | CCT<br>Pro | CAA<br>Gln | AAG<br>Lys<br>270 | GTG<br>Val | TGG<br>Trp | TGC<br>Cys | GCA<br>Ala | AGT<br>Ser<br>275 | 870 |
| GGC<br>Gly | AGG<br>Arg | AGC<br>Ser | AAG<br>Lys | GTA<br>Val<br>280 | ATA<br>Ile | AAA<br>Lys | GGG<br>Gly | TCC<br>Ser | TTG<br>Leu<br>285 | CCT<br>Pro | TTA<br>Leu | ATT<br>Ile | GGT<br>Gly | GAA<br>Glu<br>290 | GCA<br>Ala | 918 |
| GAT<br>Asp | TGC<br>Cys | CTT<br>Leu | CAC<br>His<br>295 | GCA<br>Ala | AAA<br>Lys | TAC<br>Tyr | GGT<br>Gly | GGA<br>Gly<br>300 | TTA<br>Leu | AAC<br>Asn | AAA<br>Lys | AGC<br>Ser | AAG<br>Lys<br>305 | CCT<br>Pro | TAC<br>Tyr | 966 |
| TAC<br>Tyr | ACA<br>Thr | GGA<br>Gly<br>310 | GAA<br>Glu | CAT<br>His | GCA<br>Ala | AAA<br>Lys | GCC<br>Ala<br>315 | ATA<br>Ile | GGA<br>Gly | AAT<br>Asn | TGC<br>Cys | CCA<br>Pro<br>320 | ATA<br>Ile | TGG<br>Trp | GTG<br>Val | 1014 |
| AAA<br>Lys | ACA<br>Thr<br>325 | CCT<br>Pro | TTG<br>Leu | AAG<br>Lys | CTT<br>Leu | GCC<br>Ala<br>330 | AAT<br>Asn | GGA<br>Gly | ACC<br>Thr | AAA<br>Lys | TAT<br>Tyr<br>335 | AGA<br>Arg | CCT<br>Pro | CCT<br>Pro | GCA<br>Ala | 1062 |
| AAA<br>Lys<br>340 | CTA<br>Leu | TTA<br>Leu | AAG<br>Lys | GAA<br>Glu | AGG<br>Arg<br>345 | | | | | | | | | | | 1080 |

( 2 ) INFORMATION FOR SEQ ID NO:22:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

| Asp<br>1 | Arg | Ile | Cys | Thr<br>5 | Gly | Ile | Thr | Ser | Ser<br>10 | Asn | Ser | Pro | His | Val<br>15 | Val |
| --- | --- | --- | --- | --- | --- | --- | --- | --- | --- | --- | --- | --- | --- | --- | --- |
| Lys | Thr | Ala | Thr<br>20 | Gln | Gly | Glu | Val | Asn<br>25 | Val | Thr | Gly | Val | Ile<br>30 | Pro | Leu |
| Thr | Thr | Thr<br>35 | Pro | Thr | Lys | Ser | His<br>40 | Phe | Ala | Asn | Leu | Lys<br>45 | Gly | Thr | Lys |
| Thr | Arg | Gly | Lys | Leu | Cys | Pro | Asn | Cys | Leu | Asn | Cys | Thr | Asp | Leu | Asp |

```
                  50                          55                          60
Val  Ala  Leu  Ala  Arg  Pro  Met  Cys  Ile  Gly  Thr  Ile  Pro  Ser  Ala  Lys
65                       70                       75                       80

Ala  Ser  Ile  Leu  His  Glu  Val  Arg  Pro  Val  Thr  Ser  Arg  Cys  Phe  Pro
                    85                       90                       95

Ile  Met  His  Asp  Arg  Thr  Lys  Ile  Arg  Gln  Leu  Pro  Asn  Leu  Leu  Arg
               100                      105                      110

Gly  Tyr  Glu  Asn  Ile  Arg  Leu  Ser  Thr  His  Asn  Val  Ile  Asn  Ala  Glu
          115                      120                      125

Arg  Ala  Pro  Gly  Gly  Pro  Tyr  Arg  Leu  Gly  Thr  Ser  Gly  Ser  Cys  Pro
     130                      135                      140

Asn  Val  Thr  Ser  Arg  Ser  Gly  Phe  Phe  Ala  Thr  Met  Ala  Trp  Ala  Val
145                      150                      155                      160

Pro  Arg  Asp  Asn  Lys  Thr  Ala  Thr  Asn  Pro  Leu  Thr  Val  Glu  Val  Pro
                    165                      170                      175

Tyr  Ile  Cys  Thr  Lys  Gly  Glu  Asp  Gln  Thr  Thr  Val  Trp  Gly  Phe  His
               180                      185                      190

Ser  Asp  Asn  Lys  Thr  Gln  Met  Lys  Asn  Leu  Tyr  Gly  Asp  Ser  Asn  Pro
          195                      200                      205

Gln  Lys  Phe  Thr  Ser  Ser  Ala  Asn  Gly  Val  Thr  Thr  His  Tyr  Val  Ser
     210                      215                      220

Gln  Ile  Gly  Gly  Phe  Pro  Asn  Gln  Thr  Glu  Asp  Gly  Gly  Leu  Pro  Gln
225                      230                      235                      240

Ser  Gly  Arg  Ile  Val  Val  Asp  Tyr  Met  Val  Gln  Lys  Pro  Gly  Lys  Thr
                    245                      250                      255

Gly  Thr  Ile  Val  Tyr  Gln  Arg  Gly  Val  Leu  Leu  Pro  Gln  Lys  Val  Trp
               260                      265                      270

Cys  Ala  Ser  Gly  Arg  Ser  Lys  Val  Ile  Lys  Gly  Ser  Leu  Pro  Leu  Ile
          275                      280                      285

Gly  Glu  Ala  Asp  Cys  Leu  His  Ala  Lys  Tyr  Gly  Gly  Leu  Asn  Lys  Ser
     290                      295                      300

Lys  Pro  Tyr  Tyr  Thr  Gly  Glu  His  Ala  Lys  Ala  Ile  Gly  Asn  Cys  Pro
305                      310                      315                      320

Ile  Trp  Val  Lys  Thr  Pro  Leu  Lys  Leu  Ala  Asn  Gly  Thr  Lys  Tyr  Arg
                    325                      330                      335

Pro  Pro  Ala  Lys  Leu  Leu  Lys  Glu  Arg
                    340                      345
```

( 2 ) INFORMATION FOR SEQ ID NO:23:

( i ) SEQUENCE CHARACTERISTICS:
        ( A ) LENGTH: 1080 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 46..1080
        ( D ) OTHER INFORMATION: /label=BK91

( x i ) SEQUENCE DESCRIPTION: SEQ ID NO:23:

```
ATGAAGGCAA  TAATTGTACT  ACTCATGGTA  GTAACATCCA  ACGCA GAT CGA ATC             54
                                                      Asp Arg Ile
                                                       1

TGC ACT GGG ATA ACA TCT TCA AAC TCA CCT CAT GTG GTC AAA ACA GCT              102
Cys Thr Gly Ile Thr Ser Ser Asn Ser Pro His Val Val Lys Thr Ala
     5                   10                      15
```

| | | | | | | | | | | | | | | | | |
|---|---|---|---|---|---|---|---|---|---|---|---|---|---|---|---|---|
| ACT | CAA | GGG | GAA | GTC | AAT | GTG | ACT | GGT | GTG | ATA | CCA | CTG | ACA | ACA | ACA | 150 |
| Thr | Gln | Gly | Glu | Val | Asn | Val | Thr | Gly | Val | Ile | Pro | Leu | Thr | Thr | Thr | |
| 20 | | | | 25 | | | | | 30 | | | | | | 35 | |
| CCA | ACA | AAA | TCT | CAT | TTT | GCA | AAT | CTC | AAA | GGA | ACA | AAG | ACC | AGA | GGG | 198 |
| Pro | Thr | Lys | Ser | His | Phe | Ala | Asn | Leu | Lys | Gly | Thr | Lys | Thr | Arg | Gly | |
| | | | | 40 | | | | | 45 | | | | | 50 | | |
| AAA | CTA | TGC | CCA | AAC | TGT | CTC | AAC | TGC | ACA | GAT | CTG | GAT | GTG | GCC | TTG | 246 |
| Lys | Leu | Cys | Pro | Asn | Cys | Leu | Asn | Cys | Thr | Asp | Leu | Asp | Val | Ala | Leu | |
| | | | 55 | | | | | 60 | | | | | 65 | | | |
| GCG | AGA | CCA | ATG | TGT | ATA | GGG | ACC | ATA | CCT | TCG | GCA | AAA | GCT | TCA | ATA | 294 |
| Ala | Arg | Pro | Met | Cys | Ile | Gly | Thr | Ile | Pro | Ser | Ala | Lys | Ala | Ser | Ile | |
| | | 70 | | | | | 75 | | | | | 80 | | | | |
| CTC | CAC | GAA | GTC | AGA | CCT | GTT | ACA | TCC | GGG | TGC | TTT | CCT | ATA | ATG | CAC | 342 |
| Leu | His | Glu | Val | Arg | Pro | Val | Thr | Ser | Gly | Cys | Phe | Pro | Ile | Met | His | |
| | 85 | | | | | 90 | | | | | 95 | | | | | |
| GAC | AGA | ACA | AAA | ATC | AGA | CAA | CTA | CCC | AAT | CTT | CTC | AGA | GGA | TAT | GAA | 390 |
| Asp | Arg | Thr | Lys | Ile | Arg | Gln | Leu | Pro | Asn | Leu | Leu | Arg | Gly | Tyr | Glu | |
| 100 | | | | | 105 | | | | | 110 | | | | | 115 | |
| AAT | ATC | AGA | TTA | TCA | ACC | CAT | AAC | GTT | ATC | AAC | GCA | GAA | AGG | GCA | CCA | 438 |
| Asn | Ile | Arg | Leu | Ser | Thr | His | Asn | Val | Ile | Asn | Ala | Glu | Arg | Ala | Pro | |
| | | | | 120 | | | | | 125 | | | | | 130 | | |
| GGA | GGA | CCC | TAC | AGA | CTT | GGA | ACC | TCA | GGA | TCT | TGC | CCT | AAC | GTT | ACC | 486 |
| Gly | Gly | Pro | Tyr | Arg | Leu | Gly | Thr | Ser | Gly | Ser | Cys | Pro | Asn | Val | Thr | |
| | | | 135 | | | | | 140 | | | | | 145 | | | |
| AGT | AAA | AGC | GGA | TTC | TTC | GCA | ACA | ATG | GCT | TGG | GCT | GTC | CCA | AGG | GAC | 534 |
| Ser | Lys | Ser | Gly | Phe | Phe | Ala | Thr | Met | Ala | Trp | Ala | Val | Pro | Arg | Asp | |
| | | 150 | | | | | 155 | | | | | 160 | | | | |
| AAC | AAA | ACA | GCA | ACG | AAC | CCA | CTA | ACA | GTA | GAA | GTA | CCA | TAC | ATT | TGT | 582 |
| Asn | Lys | Thr | Ala | Thr | Asn | Pro | Leu | Thr | Val | Glu | Val | Pro | Tyr | Ile | Cys | |
| | 165 | | | | | 170 | | | | | 175 | | | | | |
| ACA | AAA | GGA | GAA | GAC | CAA | ACT | ACT | GTT | TGG | GGG | TTC | CAT | TCT | GAT | AAC | 630 |
| Thr | Lys | Gly | Glu | Asp | Gln | Thr | Thr | Val | Trp | Gly | Phe | His | Ser | Asp | Asn | |
| 180 | | | | | 185 | | | | | 190 | | | | | 195 | |
| AAG | AAC | CAA | ATG | AAC | AAA | CTC | TAT | GGA | GAC | TCA | AAT | CCT | CAA | AAG | TTC | 678 |
| Lys | Asn | Gln | Met | Asn | Lys | Leu | Tyr | Gly | Asp | Ser | Asn | Pro | Gln | Lys | Phe | |
| | | | | 200 | | | | | 205 | | | | | 210 | | |
| ACC | TCA | TCT | GTC | AAT | GGA | GTA | ACC | ACA | CAT | TAT | GTT | TCT | CAG | ATT | GGT | 726 |
| Thr | Ser | Ser | Val | Asn | Gly | Val | Thr | Thr | His | Tyr | Val | Ser | Gln | Ile | Gly | |
| | | | 215 | | | | | 220 | | | | | 225 | | | |
| GGC | TTC | CCA | AAT | CAA | ACA | GAA | GAC | GGA | GGG | CTA | CCA | CAA | AGC | GGC | AGA | 774 |
| Gly | Phe | Pro | Asn | Gln | Thr | Glu | Asp | Gly | Gly | Leu | Pro | Gln | Ser | Gly | Arg | |
| | | 230 | | | | | 235 | | | | | 240 | | | | |
| ATT | GTT | GTT | GAT | TAC | ATG | GTG | CAA | AAA | CCT | GGG | AAA | ACA | GGA | ACA | ATT | 822 |
| Ile | Val | Val | Asp | Tyr | Met | Val | Gln | Lys | Pro | Gly | Lys | Thr | Gly | Thr | Ile | |
| | 245 | | | | | 250 | | | | | 255 | | | | | |
| GTC | TAT | CAA | AGA | GGT | GTT | TTG | TTG | CCT | CAA | AAG | GTG | TGG | TGT | GCA | AGT | 870 |
| Val | Tyr | Gln | Arg | Gly | Val | Leu | Leu | Pro | Gln | Lys | Val | Trp | Cys | Ala | Ser | |
| 260 | | | | | 265 | | | | | 270 | | | | | 275 | |
| GGC | AGG | AGC | AAG | GTA | ATA | AAA | GGG | TCC | TTG | CCT | TTA | ATT | GGT | GAA | GCA | 918 |
| Gly | Arg | Ser | Lys | Val | Ile | Lys | Gly | Ser | Leu | Pro | Leu | Ile | Gly | Glu | Ala | |
| | | | | 280 | | | | | 285 | | | | | 290 | | |
| GAT | TGC | CTT | CAC | GAA | AAA | TAC | GGT | GGA | TTA | AAC | AAA | AGC | AAG | CCT | TAC | 966 |
| Asp | Cys | Leu | His | Glu | Lys | Tyr | Gly | Gly | Leu | Asn | Lys | Ser | Lys | Pro | Tyr | |
| | | | 295 | | | | | 300 | | | | | 305 | | | |
| TAC | ACA | GGA | GAA | CAT | GCA | AAA | GCC | ATA | GGA | AAT | TGC | CCA | ATA | TGG | GTG | 1014 |
| Tyr | Thr | Gly | Glu | His | Ala | Lys | Ala | Ile | Gly | Asn | Cys | Pro | Ile | Trp | Val | |
| | | 310 | | | | | 315 | | | | | 320 | | | | |
| AAA | ACA | CCT | TTG | AAG | CTT | GCC | AAT | GGA | ACC | AAA | TAT | AGA | CCT | CCT | GCA | 1062 |
| Lys | Thr | Pro | Leu | Lys | Leu | Ala | Asn | Gly | Thr | Lys | Tyr | Arg | Pro | Pro | Ala | |
| | 325 | | | | | 330 | | | | | 335 | | | | | |
| AAA | CTA | TTA | AAG | GAA | AGG | | | | | | | | | | | 1080 |

Lys Leu Leu Lys Glu Arg
340              345

(2) INFORMATION FOR SEQ ID NO:24:

(i) SEQUENCE CHARACTERISTICS:
        (A) LENGTH: 345 amino acids
        (B) TYPE: amino acid
        (D) TOPOLOGY: linear (ii) MOLECULE TYPE: protein (xi) SEQUENCE DESCRIPTION: SEQ ID NO:24:

```
Asp Arg Ile Cys Thr Gly Ile Thr Ser Ser Asn Ser Pro His Val Val
 1           5                  10                  15

Lys Thr Ala Thr Gln Gly Glu Val Asn Val Thr Gly Val Ile Pro Leu
             20                  25                  30

Thr Thr Thr Pro Thr Lys Ser His Phe Ala Asn Leu Lys Gly Thr Lys
         35                  40                  45

Thr Arg Gly Lys Leu Cys Pro Asn Cys Leu Asn Cys Thr Asp Leu Asp
     50                  55                  60

Val Ala Leu Ala Arg Pro Met Cys Ile Gly Thr Ile Pro Ser Ala Lys
 65              70                  75                  80

Ala Ser Ile Leu His Glu Val Arg Pro Val Thr Ser Gly Cys Phe Pro
                 85                  90                  95

Ile Met His Asp Arg Thr Lys Ile Arg Gln Leu Pro Asn Leu Leu Arg
             100                 105                 110

Gly Tyr Glu Asn Ile Arg Leu Ser Thr His Asn Val Ile Asn Ala Glu
         115                 120                 125

Arg Ala Pro Gly Gly Pro Tyr Arg Leu Gly Thr Ser Gly Ser Cys Pro
     130                 135                 140

Asn Val Thr Ser Lys Ser Gly Phe Phe Ala Thr Met Ala Trp Ala Val
145                 150                 155                 160

Pro Arg Asp Asn Lys Thr Ala Thr Asn Pro Leu Thr Val Glu Val Pro
                 165                 170                 175

Tyr Ile Cys Thr Lys Gly Glu Asp Gln Thr Thr Val Trp Gly Phe His
             180                 185                 190

Ser Asp Asn Lys Asn Gln Met Asn Lys Leu Tyr Gly Asp Ser Asn Pro
         195                 200                 205

Gln Lys Phe Thr Ser Ser Val Asn Gly Val Thr Thr His Tyr Val Ser
     210                 215                 220

Gln Ile Gly Gly Phe Pro Asn Gln Thr Glu Asp Gly Gly Leu Pro Gln
225                 230                 235                 240

Ser Gly Arg Ile Val Val Asp Tyr Met Val Gln Lys Pro Gly Lys Thr
                 245                 250                 255

Gly Thr Ile Val Tyr Gln Arg Gly Val Leu Leu Pro Gln Lys Val Trp
             260                 265                 270

Cys Ala Ser Gly Arg Ser Lys Val Ile Lys Gly Ser Leu Pro Leu Ile
         275                 280                 285

Gly Glu Ala Asp Cys Leu His Glu Lys Tyr Gly Gly Leu Asn Lys Ser
     290                 295                 300

Lys Pro Tyr Tyr Thr Gly Glu His Ala Lys Ala Ile Gly Asn Cys Pro
305                 310                 315                 320

Ile Trp Val Lys Thr Pro Leu Lys Leu Ala Asn Gly Thr Lys Tyr Arg
                 325                 330                 335

Pro Pro Ala Lys Leu Leu Lys Glu Arg
                 340                 345
```

(2) INFORMATION FOR SEQ ID NO:25:

(i) SEQUENCE CHARACTERISTICS:
        (A) LENGTH: 1080 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 46..1080
        (D) OTHER INFORMATION: /label=TX91

(xi) SEQUENCE DESCRIPTION: SEQ ID NO:25:

```
ATGAAGGCAA TAATTGTACT ACTCATGGTA GTAACATCCA ACGCA GAT CGA ATC            54
                                                  Asp Arg Ile
                                                   1

TGC ACT GGG ATA ACA TCT TCA AAC TCA CCT CAT GTG GTC AAA ACA GCT         102
Cys Thr Gly Ile Thr Ser Ser Asn Ser Pro His Val Val Lys Thr Ala
         5              10              15

ACT CAA GGG GAA GTC AAT GTG ACT GGT GTG ATA CCA CTG ACA ACA ACA         150
Thr Gln Gly Glu Val Asn Val Thr Gly Val Ile Pro Leu Thr Thr Thr
 20              25              30                          35

CCA ACA AAA TCT CAT TTT GCA AAT CTC AAA GGA ACA AAG ACC AGA GGG         198
Pro Thr Lys Ser His Phe Ala Asn Leu Lys Gly Thr Lys Thr Arg Gly
                 40              45                  50

AAA CTA TGC CCA AAC TGT CTC AAC TGC ACA GAT CTG GAT GTG GCC TTG         246
Lys Leu Cys Pro Asn Cys Leu Asn Cys Thr Asp Leu Asp Val Ala Leu
             55              60              65

GCG AGA CCA ATG TGT ATA GGG ACC ATA CCT TCG GCA AAA GCT TCA ATA         294
Ala Arg Pro Met Cys Ile Gly Thr Ile Pro Ser Ala Lys Ala Ser Ile
         70              75              80

CTC CAC GAA GTC AGG CCT GTT ACA TCC GGG TGC TTT CCT ATA ATG CAC         342
Leu His Glu Val Arg Pro Val Thr Ser Gly Cys Phe Pro Ile Met His
     85              90              95

GAC AGA ACA AAA ATC AGA CAG CTA CCC AAT CTT CTC AGA GGA TAT GAA         390
Asp Arg Thr Lys Ile Arg Gln Leu Pro Asn Leu Leu Arg Gly Tyr Glu
100             105             110                     115

AAT ATC AGA TTA TCA ACC CAT AAC GTT ATC AAC GCA GAA AGG GCA CCA         438
Asn Ile Arg Leu Ser Thr His Asn Val Ile Asn Ala Glu Arg Ala Pro
                120             125             130

GGA GGA CCC TAC AGA CTT GGA ACC TCA GGA TCT TGC CCT AAC GTT ACC         486
Gly Gly Pro Tyr Arg Leu Gly Thr Ser Gly Ser Cys Pro Asn Val Thr
             135             140             145

AGT AGA AGC GGA TTC TTC GCA ACA ATG GCT TGG GCT GTC CCA AGG GAC         534
Ser Arg Ser Gly Phe Phe Ala Thr Met Ala Trp Ala Val Pro Arg Asp
        150             155             160

AAC AAA ACA GCA ACG AAC CCA CTA ACA GTA GAA GTA CCA TAC ATT TGT         582
Asn Lys Thr Ala Thr Asn Pro Leu Thr Val Glu Val Pro Tyr Ile Cys
165             170             175

ACA AAA GGA GAA GAC CAA ACT ACT GTT TGG GGG TTC CAT TCT GAT AAC         630
Thr Lys Gly Glu Asp Gln Thr Thr Val Trp Gly Phe His Ser Asp Asn
180             185             190                     195

AAA ATC CAA ATG AAC AAA CTC TAT GGA GAC TCA AAT CCT CAA AAA TTC         678
Lys Ile Gln Met Asn Lys Leu Tyr Gly Asp Ser Asn Pro Gln Lys Phe
                200             205             210

ACC TCA TCT GCC AAT GGA GTA ACC ACA CAT TAT GTT TCT CAG ATT GGT         726
Thr Ser Ser Ala Asn Gly Val Thr Thr His Tyr Val Ser Gln Ile Gly
             215             220             225

GGC TTC CCA AAT CAA ACA GAA GAC GGA GGG CTA CCA CAA AGC GGC AGA         774
Gly Phe Pro Asn Gln Thr Glu Asp Gly Gly Leu Pro Gln Ser Gly Arg
        230             235             240
```

```
ATT GTT GTT GAT TAC ATG GTG CAA AAA CCT GGG AAA ACA GGA ACA ATT      822
Ile Val Val Asp Tyr Met Val Gln Lys Pro Gly Lys Thr Gly Thr Ile
    245             250                 255

GTC TAT CAA AGA GGT GTT TTA TTA CCT CAA AAG GTG TGG TGT GCA AGT      870
Val Tyr Gln Arg Gly Val Leu Leu Pro Gln Lys Val Trp Cys Ala Ser
260             265                 270                 275

GGC AGG AGC AAG GTA ATA AAA GGG TCC TTG CCT TTA ATT GGT GAA GCA      918
Gly Arg Ser Lys Val Ile Lys Gly Ser Leu Pro Leu Ile Gly Glu Ala
                280             285                 290

GAT TGC CTT CAC GAA AAA TAC GGT GGA TTA AAC AAA AGC AAG CCT TAC      966
Asp Cys Leu His Glu Lys Tyr Gly Gly Leu Asn Lys Ser Lys Pro Tyr
            295                 300                 305

TAC ACA GGT GAA CAT GCA AAA GCC ATA GGA AAT TGC CCA ATA TGG GTG     1014
Tyr Thr Gly Glu His Ala Lys Ala Ile Gly Asn Cys Pro Ile Trp Val
        310                 315                 320

AAA ACA CCT TTG AAG CTT GCC AAT GGA ACC AAA TAT AGA CCT CCT GCA     1062
Lys Thr Pro Leu Lys Leu Ala Asn Gly Thr Lys Tyr Arg Pro Pro Ala
    325                 330                 335

AAA CTA TTA AAG GAA AGG                                              1080
Lys Leu Leu Lys Glu Arg
340             345
```

( 2 ) INFORMATION FOR SEQ ID NO:26:

( i ) SEQUENCE CHARACTERISTICS:
        ( A ) LENGTH: 345 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Asp Arg Ile Cys Thr Gly Ile Thr Ser Ser Asn Ser Pro His Val Val
 1               5                  10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Lys
        35                  40                  45

Thr Arg Gly Lys Leu Cys Pro Asn Cys Leu Asn Cys Thr Asp Leu Asp
    50                  55                  60

Val Ala Leu Ala Arg Pro Met Cys Ile Gly Thr Ile Pro Ser Ala Lys
65                  70                  75                  80

Ala Ser Ile Leu His Glu Val Arg Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr His Asn Val Ile Asn Ala Glu
        115                 120                 125

Arg Ala Pro Gly Gly Pro Tyr Arg Leu Gly Thr Ser Gly Ser Cys Pro
    130                 135                 140

Asn Val Thr Ser Arg Ser Gly Phe Phe Ala Thr Met Ala Trp Ala Val
145                 150                 155                 160

Pro Arg Asp Asn Lys Thr Ala Thr Asn Pro Leu Thr Val Glu Val Pro
                165                 170                 175

Tyr Ile Cys Thr Lys Gly Glu Asp Gln Thr Thr Val Trp Gly Phe His
            180                 185                 190

Ser Asp Asn Lys Ile Gln Met Asn Lys Leu Tyr Gly Asp Ser Asn Pro
        195                 200                 205

Gln Lys Phe Thr Ser Ser Ala Asn Gly Val Thr Thr His Tyr Val Ser
    210                 215                 220
```

```
Gln  Ile  Gly  Gly  Phe  Pro  Asn  Gln  Thr  Glu  Asp  Gly  Gly  Leu  Pro  Gln
225                      230                      235                      240

Ser  Gly  Arg  Ile  Val  Val  Asp  Tyr  Met  Val  Gln  Lys  Pro  Gly  Lys  Thr
                    245                      250                      255

Gly  Thr  Ile  Val  Tyr  Gln  Arg  Gly  Val  Leu  Leu  Pro  Gln  Lys  Val  Trp
                    260                      265                      270

Cys  Ala  Ser  Gly  Arg  Ser  Lys  Val  Ile  Lys  Gly  Ser  Leu  Pro  Leu  Ile
               275                      280                      285

Gly  Glu  Ala  Asp  Cys  Leu  His  Glu  Lys  Tyr  Gly  Gly  Leu  Asn  Lys  Ser
     290                      295                      300

Lys  Pro  Tyr  Tyr  Thr  Gly  Glu  His  Ala  Lys  Ala  Ile  Gly  Asn  Cys  Pro
305                      310                      315                      320

Ile  Trp  Val  Lys  Thr  Pro  Leu  Lys  Leu  Ala  Asn  Gly  Thr  Lys  Tyr  Arg
                    325                      330                      335

Pro  Pro  Ala  Lys  Leu  Leu  Lys  Glu  Arg
               340                      345
```

(2) INFORMATION FOR SEQ ID NO:27:

(i) SEQUENCE CHARACTERISTICS:
        (A) LENGTH: 1086 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 46..1086
        (D) OTHER INFORMATION: /label=VI87

(xi) SEQUENCE DESCRIPTION: SEQ ID NO:27:

```
ATGAAGGCAA  TAATTGTACT  ACTCATGGTA  GTAACATCCA  ATGCA GAT CGA ATC                54
                                                     Asp Arg Ile
                                                      1

TGC ACT GGG ATA ACA TCG TCA AAC TCA CCC CAT GTG GTC AAA ACT GCT                102
Cys Thr Gly Ile Thr Ser Ser Asn Ser Pro His Val Val Lys Thr Ala
          5                   10                  15

ACT CAA GGG GAA GTC AAT GTG ACT GGT GTG ATA CCA CTG ACA ACA ACA                150
Thr Gln Gly Glu Val Asn Val Thr Gly Val Ile Pro Leu Thr Thr Thr
 20                  25                  30                  35

CCA ACC AAA TCT CAT TTT GCA AAT CTC AAA GGA ACA AAA ACC AGA GGG                198
Pro Thr Lys Ser His Phe Ala Asn Leu Lys Gly Thr Lys Thr Arg Gly
                 40                  45                  50

AAA CTA TGC CCA AAG TGT CTC AAC TGC ACA GAT CTG GAC GTG GCC TTG                246
Lys Leu Cys Pro Lys Cys Leu Asn Cys Thr Asp Leu Asp Val Ala Leu
             55                  60                  65

GCG AGA CCA AAG TGC ATG GGG ACC ATA CCT TCG GCA AAA GCT TCA ATA                294
Ala Arg Pro Lys Cys Met Gly Thr Ile Pro Ser Ala Lys Ala Ser Ile
         70                  75                  80

CTC CAT GAA GTC AAA CCT GTT ACA TCT GGG TGC TTT CCT ATA ATG CAC                342
Leu His Glu Val Lys Pro Val Thr Ser Gly Cys Phe Pro Ile Met His
     85                  90                  95

GAC AGA ACA AAA ATT AGA CAG CTA CCC AAT CTT CTC AGA GGA TAC GAA                390
Asp Arg Thr Lys Ile Arg Gln Leu Pro Asn Leu Leu Arg Gly Tyr Glu
100                 105                 110                 115

CAT ATC AGG TTA TCA ACC CAT AAC GTT ATC AAC GCA GAA ACG GCA CCA                438
His Ile Arg Leu Ser Thr His Asn Val Ile Asn Ala Glu Thr Ala Pro
                120                 125                 130

GGA GGA CCC TAC AAA GTT GGA ACC TCA GGG TCT TGC CCT AAC GTT ACC                486
Gly Gly Pro Tyr Lys Val Gly Thr Ser Gly Ser Cys Pro Asn Val Thr
            135                 140                 145
```

| | | | | | | | | | | | | | | | | |
|---|---|---|---|---|---|---|---|---|---|---|---|---|---|---|---|---|
| AAT | GGA | AAC | GGA | TTC | TTC | GCA | ACA | ATG | GCT | TGG | GCT | GTC | CCA | AAA | AAC | 534 |
| Asn | Gly | Asn | Gly | Phe | Phe | Ala | Thr | Met | Ala | Trp | Ala | Val | Pro | Lys | Asn | |
| | | 150 | | | | | 155 | | | | | 160 | | | | |
| GAC | AAC | AAC | AAA | ACA | GCA | ACA | AAT | CCA | TTA | ACA | GTA | GAA | GTA | CCA | TAC | 582 |
| Asp | Asn | Asn | Lys | Thr | Ala | Thr | Asn | Pro | Leu | Thr | Val | Glu | Val | Pro | Tyr | |
| | 165 | | | | | 170 | | | | | 175 | | | | | |
| ATT | TGT | ACA | GAA | GGA | GAA | GAC | CAA | ATT | ACT | GTT | TGG | GGG | TTC | CAC | TCT | 630 |
| Ile | Cys | Thr | Glu | Gly | Glu | Asp | Gln | Ile | Thr | Val | Trp | Gly | Phe | His | Ser | |
| 180 | | | | | 185 | | | | | 190 | | | | | 195 | |
| GAT | AGC | GAA | ACC | CAA | ATG | GTA | AAA | CTC | TAT | GGA | GAC | TCA | AAG | CCT | CAG | 678 |
| Asp | Ser | Glu | Thr | Gln | Met | Val | Lys | Leu | Tyr | Gly | Asp | Ser | Lys | Pro | Gln | |
| | | | | 200 | | | | | 205 | | | | | 210 | | |
| AAG | TTC | ACC | TCA | TCT | GCC | AAT | GGA | GTA | ACC | ACA | CAT | TAC | GTT | TCA | CAG | 726 |
| Lys | Phe | Thr | Ser | Ser | Ala | Asn | Gly | Val | Thr | Thr | His | Tyr | Val | Ser | Gln | |
| | | | 215 | | | | | 220 | | | | | 225 | | | |
| ATT | GGT | GGC | TTC | CCA | AAT | CAA | GCA | GAA | GAC | GGA | GGG | CTA | CCA | CAA | AGC | 774 |
| Ile | Gly | Gly | Phe | Pro | Asn | Gln | Ala | Glu | Asp | Gly | Gly | Leu | Pro | Gln | Ser | |
| | | 230 | | | | | 235 | | | | | 240 | | | | |
| GGT | AGA | ATT | GTT | GTT | GAT | TAC | ATG | GTG | CAA | AAA | TCT | GGA | AAA | ACA | GGA | 822 |
| Gly | Arg | Ile | Val | Val | Asp | Tyr | Met | Val | Gln | Lys | Ser | Gly | Lys | Thr | Gly | |
| | 245 | | | | | 250 | | | | | 255 | | | | | |
| ACA | ATT | ACC | TAC | CAA | AGA | GGT | ATT | TTA | TTG | CCT | CAA | AAA | GTG | TGG | TGC | 870 |
| Thr | Ile | Thr | Tyr | Gln | Arg | Gly | Ile | Leu | Leu | Pro | Gln | Lys | Val | Trp | Cys | |
| 260 | | | | | 265 | | | | | 270 | | | | | 275 | |
| GCA | AGT | GGC | AGG | AGC | AAG | GTA | ATA | AAA | GGG | TCC | TTG | CCT | TTA | ATT | GGT | 918 |
| Ala | Ser | Gly | Arg | Ser | Lys | Val | Ile | Lys | Gly | Ser | Leu | Pro | Leu | Ile | Gly | |
| | | | | 280 | | | | | 285 | | | | | 290 | | |
| GAA | GCA | GAT | TGC | CTC | CAC | GAA | AAA | TAC | GGT | GGA | TTA | AAC | AAA | AGC | AAG | 966 |
| Glu | Ala | Asp | Cys | Leu | His | Glu | Lys | Tyr | Gly | Gly | Leu | Asn | Lys | Ser | Lys | |
| | | | 295 | | | | | 300 | | | | | 305 | | | |
| CCT | TAC | TAC | ACA | GGA | GAA | CAT | GCA | AAA | GCC | ATA | GGA | AAT | TGC | CCA | ATA | 1014 |
| Pro | Tyr | Tyr | Thr | Gly | Glu | His | Ala | Lys | Ala | Ile | Gly | Asn | Cys | Pro | Ile | |
| | | 310 | | | | | 315 | | | | | 320 | | | | |
| TGG | GTG | AAA | ACA | CCC | TTG | AAG | CTG | GCC | AAT | GGA | ACC | AAA | TAT | AGA | CCT | 1062 |
| Trp | Val | Lys | Thr | Pro | Leu | Lys | Leu | Ala | Asn | Gly | Thr | Lys | Tyr | Arg | Pro | |
| | 325 | | | | | 330 | | | | | 335 | | | | | |
| CCT | GCA | AAA | CTA | TTA | AAG | GAA | AGG | | | | | | | | | 1086 |
| Pro | Ala | Lys | Leu | Leu | Lys | Glu | Arg | | | | | | | | | |
| 340 | | | | | 345 | | | | | | | | | | | |

( 2 ) INFORMATION FOR SEQ ID NO:28:

( i ) SEQUENCE CHARACTERISTICS:
        ( A ) LENGTH: 347 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

| | | | | | | | | | | | | | | |
|---|---|---|---|---|---|---|---|---|---|---|---|---|---|---|
| Asp | Arg | Ile | Cys | Thr | Gly | Ile | Thr | Ser | Ser | Asn | Ser | Pro | His | Val | Val |
| 1 | | | | 5 | | | | | 10 | | | | | 15 | |
| Lys | Thr | Ala | Thr | Gln | Gly | Glu | Val | Asn | Val | Thr | Gly | Val | Ile | Pro | Leu |
| | | | 20 | | | | | 25 | | | | | 30 | | |
| Thr | Thr | Thr | Pro | Thr | Lys | Ser | His | Phe | Ala | Asn | Leu | Lys | Gly | Thr | Lys |
| | | 35 | | | | | 40 | | | | | 45 | | | |
| Thr | Arg | Gly | Lys | Leu | Cys | Pro | Lys | Cys | Leu | Asn | Cys | Thr | Asp | Leu | Asp |
| | 50 | | | | | 55 | | | | | 60 | | | | |
| Val | Ala | Leu | Ala | Arg | Pro | Lys | Cys | Met | Gly | Thr | Ile | Pro | Ser | Ala | Lys |
| 65 | | | | 70 | | | | | 75 | | | | | 80 | |
| Ala | Ser | Ile | Leu | His | Glu | Val | Lys | Pro | Val | Thr | Ser | Gly | Cys | Phe | Pro |
| | | | | 85 | | | | | 90 | | | | | 95 | |

Ile Met His Asp Arg Thr Lys Ile Arg Gln Leu Pro Asn Leu Leu Arg
        100                 105                 110

Gly Tyr Glu His Ile Arg Leu Ser Thr His Asn Val Ile Asn Ala Glu
            115                 120                 125

Thr Ala Pro Gly Gly Pro Tyr Lys Val Gly Thr Ser Gly Ser Cys Pro
        130                 135                 140

Asn Val Thr Asn Gly Asn Gly Phe Phe Ala Thr Met Ala Trp Ala Val
145                     150                 155                 160

Pro Lys Asn Asp Asn Asn Lys Thr Ala Thr Asn Pro Leu Thr Val Glu
                165                 170                 175

Val Pro Tyr Ile Cys Thr Glu Gly Glu Asp Gln Ile Thr Val Trp Gly
            180                 185                 190

Phe His Ser Asp Ser Glu Thr Gln Met Val Lys Leu Tyr Gly Asp Ser
            195                 200                 205

Lys Pro Gln Lys Phe Thr Ser Ser Ala Asn Gly Val Thr Thr His Tyr
        210                 215                 220

Val Ser Gln Ile Gly Gly Phe Pro Asn Gln Ala Glu Asp Gly Gly Leu
225                     230                 235                 240

Pro Gln Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
        275                 280                 285

Leu Ile Gly Glu Ala Asp Cys Leu His Glu Lys Tyr Gly Gly Leu Asn
        290                 295                 300

Lys Ser Lys Pro Tyr Tyr Thr Gly Glu His Ala Lys Ala Ile Gly Asn
305                     310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Arg
            340                 345

( 2 ) INFORMATION FOR SEQ ID NO:29:

( i ) SEQUENCE CHARACTERISTICS:
        ( A ) LENGTH: 347 amino acids
        ( B ) TYPE: amino acid
        ( D ) TOPOLOGY: linear ( i i ) MOLECULE TYPE: protein ( x i ) SEQUENCE DESCRIPTION: SEQ ID NO:29:

Asp Arg Ile Cys Thr Gly Ile Thr Ser Ser Asn Ser Pro His Val Val
1                   5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Lys
        35                  40                  45

Thr Arg Gly Lys Leu Cys Pro Lys Cys Leu Asn Cys Thr Asp Leu Asp
    50                  55                  60

Val Ala Leu Ala Arg Pro Lys Cys Met Gly Thr Ile Pro Ser Ala Lys
65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
        100                 105                 110

```
Gly Tyr Glu His Ile Arg Leu Ser Thr His Asn Val Ile Asn Ala Glu
            115                 120                 125
Thr Ala Pro Gly Gly Pro Tyr Lys Val Gly Thr Ser Gly Ser Cys Pro
        130                 135                 140
Asn Val Thr Asn Gly Asn Gly Phe Phe Ala Thr Met Ala Trp Ala Val
145                 150                 155                 160
Pro Lys Asn Asn Asn Asn Lys Thr Ala Thr Asn Pro Leu Thr Val Glu
                165                 170                 175
Val Pro Tyr Ile Cys Thr Glu Gly Glu Asp Gln Ile Thr Val Trp Gly
            180                 185                 190
Phe His Ser Asp Asn Glu Ala Gln Met Val Lys Leu Tyr Gly Asp Ser
            195                 200                 205
Lys Pro Gln Lys Phe Thr Ser Ser Ala Asn Gly Val Thr Thr His Tyr
        210                 215                 220
Val Ser Gln Ile Gly Gly Phe Pro Asn Gln Ala Glu Asp Gly Gly Leu
225                 230                 235                 240
Pro Gln Ser Gly Arg Ile Val Val Asp Tyr Met Val Gln Lys Ser Gly
                245                 250                 255
Lys Thr Gly Thr Ile Thr Tyr Gln Arg Gly Ile Leu Leu Pro Gln Lys
            260                 265                 270
Val Trp Cys Ala Ser Gly Arg Ser Lys Val Ile Lys Gly Ser Leu Pro
        275                 280                 285
Leu Ile Gly Glu Arg Asp Cys Leu His Glu Lys Tyr Gly Gly Leu Asn
        290                 295                 300
Lys Ser Lys Pro Tyr Tyr Thr Gly Glu His Ala Lys Ala Ile Gly Asn
305                 310                 315                 320
Cys Pro Ile Trp Val Lys Thr Pro Leu Lys Leu Ala Asn Gly Thr Lys
                325                 330                 335
Tyr Arg Pro Pro Ala Lys Leu Leu Lys Glu Arg
            340                 345
```

( 2 ) INFORMATION FOR SEQ ID NO:30:

( i ) SEQUENCE CHARACTERISTICS:
        ( A ) LENGTH: 1080 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 46..1080
        ( D ) OTHER INFORMATION: /label=YM88

( x i ) SEQUENCE DESCRIPTION: SEQ ID NO:30:

```
ATGAAGGCAA TAATTGTACT ACTCATGGTA GTAACATCCA ACGCA GAT CGA ATC        54
                                                 Asp Arg Ile
                                                  1
TGC ACT GGG ATA ACA TCT TCA AAC TCA CCT CAT GTG GTC AAA ACA GCT     102
Cys Thr Gly Ile Thr Ser Ser Asn Ser Pro His Val Val Lys Thr Ala
      5              10                 15
ACT CAA GGG GAA GTT AAT GTG ACT GGT GTG ATA CCA CTG ACA ACA ACA     150
Thr Gln Gly Glu Val Asn Val Thr Gly Val Ile Pro Leu Thr Thr Thr
 20              25                 30                         35
CCA ACA AAA TCT CAT TTT GCA AAT CTC AAA GGA ACA AAG ACC AGA GGG     198
Pro Thr Lys Ser His Phe Ala Asn Leu Lys Gly Thr Lys Thr Arg Gly
             40                 45                 50
AAA CTA TGC CCA AAC TGT CTC AAC TGC ACA GAT CTG GAT GTG GCC TTG     246
Lys Leu Cys Pro Asn Cys Leu Asn Cys Thr Asp Leu Asp Val Ala Leu
```

|  |  |  |  |  |  |  |  |  |  |  |  |  |  |  |  |
|---|---|---|---|---|---|---|---|---|---|---|---|---|---|---|---|
| GCG | AGA | CCA | ATG | TGT | ATG | GGG | ACC | ATA | CCT | TCG | GCA | AAA | GCT | TCA | ATA | 294
| Ala | Arg | Pro | Met | Cys | Met | Gly | Thr | Ile | Pro | Ser | Ala | Lys | Ala | Ser | Ile |
|  | 70 |  |  |  |  | 75 |  |  |  |  | 80 |  |  |  |  |
| CTC | CAC | GAA | GTC | AGA | CCT | GTT | ACA | TCC | GGG | TGC | TTT | CCT | ATA | ATG | CAC | 342
| Leu | His | Glu | Val | Arg | Pro | Val | Thr | Ser | Gly | Cys | Phe | Pro | Ile | Met | His |
|  | 85 |  |  |  |  | 90 |  |  |  |  | 95 |  |  |  |  |
| GAC | AGA | ACA | AAA | ATC | AGA | CAG | CTA | CCC | AAT | CTT | CTC | AGA | GGA | TAT | GAA | 390
| Asp | Arg | Thr | Lys | Ile | Arg | Gln | Leu | Pro | Asn | Leu | Leu | Arg | Gly | Tyr | Glu |
| 100 |  |  |  |  | 105 |  |  |  |  | 110 |  |  |  |  | 115 |
| AAT | ATC | AGA | TTA | TCA | ACC | CAT | AAC | GTT | ATC | AAC | GCA | GAA | AGG | GCA | CCA | 438
| Asn | Ile | Arg | Leu | Ser | Thr | His | Asn | Val | Ile | Asn | Ala | Glu | Arg | Ala | Pro |
|  |  |  |  | 120 |  |  |  |  | 125 |  |  |  |  | 130 |  |
| GGA | GGA | CCC | TAC | AGA | CTT | GGA | ACC | TCA | GGA | TCT | TGC | CCT | AAC | GTT | ACC | 486
| Gly | Gly | Pro | Tyr | Arg | Leu | Gly | Thr | Ser | Gly | Ser | Cys | Pro | Asn | Val | Thr |
|  |  |  | 135 |  |  |  |  | 140 |  |  |  |  | 145 |  |  |
| AGT | AGA | AAC | GGA | TTC | TTC | GCA | ACA | ATG | GCT | TGG | GCT | GTC | CCA | AGG | GAC | 534
| Ser | Arg | Asn | Gly | Phe | Phe | Ala | Thr | Met | Ala | Trp | Ala | Val | Pro | Arg | Asp |
|  |  | 150 |  |  |  |  | 155 |  |  |  |  | 160 |  |  |  |
| AAC | AAA | ACA | GCA | ACG | AAT | CCA | CTA | ACA | GTA | GAA | GTA | CCA | TAC | ATT | TGC | 582
| Asn | Lys | Thr | Ala | Thr | Asn | Pro | Leu | Thr | Val | Glu | Val | Pro | Tyr | Ile | Cys |
|  | 165 |  |  |  |  | 170 |  |  |  |  | 175 |  |  |  |  |
| ACA | AAA | GGA | GAA | GAC | CAA | ATT | ACT | GTT | TGG | GGG | TTC | CAT | TCT | GAT | GAC | 630
| Thr | Lys | Gly | Glu | Asp | Gln | Ile | Thr | Val | Trp | Gly | Phe | His | Ser | Asp | Asp |
| 180 |  |  |  |  | 185 |  |  |  |  | 190 |  |  |  |  | 195 |
| AAA | ACC | CAA | ATG | AAA | AAA | CTC | TAT | GGA | GAC | TCA | AAT | CCT | CAA | AAG | TTC | 678
| Lys | Thr | Gln | Met | Lys | Lys | Leu | Tyr | Gly | Asp | Ser | Asn | Pro | Gln | Lys | Phe |
|  |  |  | 200 |  |  |  |  | 205 |  |  |  |  | 210 |  |  |
| ACC | TCA | TCT | GCC | AAT | GGA | GTA | ACC | ACA | CAT | TAT | GTT | TCT | CAG | ATT | GGT | 726
| Thr | Ser | Ser | Ala | Asn | Gly | Val | Thr | Thr | His | Tyr | Val | Ser | Gln | Ile | Gly |
|  |  | 215 |  |  |  |  | 220 |  |  |  |  | 225 |  |  |  |
| GAC | TTC | CCA | AAT | CAA | ACA | GAA | GAC | GGA | GGG | CTA | CCA | CAA | AGC | GGC | AGA | 774
| Asp | Phe | Pro | Asn | Gln | Thr | Glu | Asp | Gly | Gly | Leu | Pro | Gln | Ser | Gly | Arg |
|  |  | 230 |  |  |  |  | 235 |  |  |  |  | 240 |  |  |  |
| ATT | GTT | GTT | GAT | TAC | ATG | GTG | CAA | AAA | CCT | GGG | AAA | ACA | GGA | ACA | ATA | 822
| Ile | Val | Val | Asp | Tyr | Met | Val | Gln | Lys | Pro | Gly | Lys | Thr | Gly | Thr | Ile |
|  | 245 |  |  |  |  | 250 |  |  |  |  | 255 |  |  |  |  |
| GTC | TAT | CAA | AGA | GGT | GTT | TTG | TTG | CCT | CAA | AAG | GTG | TGG | TGC | GCA | AGT | 870
| Val | Tyr | Gln | Arg | Gly | Val | Leu | Leu | Pro | Gln | Lys | Val | Trp | Cys | Ala | Ser |
| 260 |  |  |  |  | 265 |  |  |  |  | 270 |  |  |  |  | 275 |
| GGC | AGG | AGC | AAG | GTA | ATA | AAA | GGG | TCC | TTG | CCT | TTA | ATT | GGT | GAA | GCA | 918
| Gly | Arg | Ser | Lys | Val | Ile | Lys | Gly | Ser | Leu | Pro | Leu | Ile | Gly | Glu | Ala |
|  |  |  | 280 |  |  |  |  | 285 |  |  |  |  | 290 |  |  |
| GAT | TGC | CTT | CAC | GCA | AAA | TAC | GGT | GGA | TTA | AAC | AAA | AGC | AAG | CCT | TAC | 966
| Asp | Cys | Leu | His | Ala | Lys | Tyr | Gly | Gly | Leu | Asn | Lys | Ser | Lys | Pro | Tyr |
|  |  |  | 295 |  |  |  |  | 300 |  |  |  |  | 305 |  |  |
| TAC | ACA | GGA | GAA | CAT | GCA | AAA | GCC | ATA | GGA | AAT | TGC | CCA | ATA | TGG | GTG | 1014
| Tyr | Thr | Gly | Glu | His | Ala | Lys | Ala | Ile | Gly | Asn | Cys | Pro | Ile | Trp | Val |
|  |  | 310 |  |  |  |  | 315 |  |  |  |  | 320 |  |  |  |
| AAA | ACA | CCT | TTG | AAG | CTT | GCC | AAT | GGA | ACC | AAA | TAT | AGA | CCT | CCT | GCA | 1062
| Lys | Thr | Pro | Leu | Lys | Leu | Ala | Asn | Gly | Thr | Lys | Tyr | Arg | Pro | Pro | Ala |
| 325 |  |  |  |  | 330 |  |  |  |  | 335 |  |  |  |  |  |
| AAA | CTA | TTA | AAG | GAA | AGG |  |  |  |  |  |  |  |  |  |  | 1080
| Lys | Leu | Leu | Lys | Glu | Arg |  |  |  |  |  |  |  |  |  |  |
| 340 |  |  |  |  | 345 |  |  |  |  |  |  |  |  |  |  |

( 2 ) INFORMATION FOR SEQ ID NO:31:

( i ) SEQUENCE CHARACTERISTICS:
        ( A ) LENGTH: 345 amino acids
        ( B ) TYPE: amino acid
        ( D ) TOPOLOGY: linear (ii) MOLECULE TYPE: protein (xi) SEQUENCE DESCRIPTION: SEQ ID NO:31:

| Asp | Arg | Ile | Cys | Thr | Gly | Ile | Thr | Ser | Ser | Asn | Ser | Pro | His | Val | Val |
|---|---|---|---|---|---|---|---|---|---|---|---|---|---|---|---|
| 1 |  |  |  | 5 |  |  |  |  | 10 |  |  |  |  | 15 |  |

| Lys | Thr | Ala | Thr | Gln | Gly | Glu | Val | Asn | Val | Thr | Gly | Val | Ile | Pro | Leu |
|---|---|---|---|---|---|---|---|---|---|---|---|---|---|---|---|
|  |  |  | 20 |  |  |  |  | 25 |  |  |  |  | 30 |  |  |

| Thr | Thr | Thr | Pro | Thr | Lys | Ser | His | Phe | Ala | Asn | Leu | Lys | Gly | Thr | Lys |
|---|---|---|---|---|---|---|---|---|---|---|---|---|---|---|---|
|  |  | 35 |  |  |  |  | 40 |  |  |  |  | 45 |  |  |  |

| Thr | Arg | Gly | Lys | Leu | Cys | Pro | Asn | Cys | Leu | Asn | Cys | Thr | Asp | Leu | Asp |
|---|---|---|---|---|---|---|---|---|---|---|---|---|---|---|---|
|  | 50 |  |  |  |  | 55 |  |  |  |  | 60 |  |  |  |  |

| Val | Ala | Leu | Ala | Arg | Pro | Met | Cys | Met | Gly | Thr | Ile | Pro | Ser | Ala | Lys |
|---|---|---|---|---|---|---|---|---|---|---|---|---|---|---|---|
| 65 |  |  |  |  | 70 |  |  |  |  | 75 |  |  |  |  | 80 |

| Ala | Ser | Ile | Leu | His | Glu | Val | Arg | Pro | Val | Thr | Ser | Gly | Cys | Phe | Pro |
|---|---|---|---|---|---|---|---|---|---|---|---|---|---|---|---|
|  |  |  |  | 85 |  |  |  |  | 90 |  |  |  |  | 95 |  |

| Ile | Met | His | Asp | Arg | Thr | Lys | Ile | Arg | Gln | Leu | Pro | Asn | Leu | Leu | Arg |
|---|---|---|---|---|---|---|---|---|---|---|---|---|---|---|---|
|  |  |  | 100 |  |  |  |  | 105 |  |  |  |  | 110 |  |  |

| Gly | Tyr | Glu | Asn | Ile | Arg | Leu | Ser | Thr | His | Asn | Val | Ile | Asn | Ala | Glu |
|---|---|---|---|---|---|---|---|---|---|---|---|---|---|---|---|
|  |  | 115 |  |  |  |  | 120 |  |  |  |  | 125 |  |  |  |

| Arg | Ala | Pro | Gly | Gly | Pro | Tyr | Arg | Leu | Gly | Thr | Ser | Gly | Ser | Cys | Pro |
|---|---|---|---|---|---|---|---|---|---|---|---|---|---|---|---|
|  | 130 |  |  |  |  | 135 |  |  |  |  | 140 |  |  |  |  |

| Asn | Val | Thr | Ser | Arg | Asn | Gly | Phe | Phe | Ala | Thr | Met | Ala | Trp | Ala | Val |
|---|---|---|---|---|---|---|---|---|---|---|---|---|---|---|---|
| 145 |  |  |  |  | 150 |  |  |  |  | 155 |  |  |  |  | 160 |

| Pro | Arg | Asp | Asn | Lys | Thr | Ala | Thr | Asn | Pro | Leu | Thr | Val | Glu | Val | Pro |
|---|---|---|---|---|---|---|---|---|---|---|---|---|---|---|---|
|  |  |  |  | 165 |  |  |  |  | 170 |  |  |  |  | 175 |  |

| Tyr | Ile | Cys | Thr | Lys | Gly | Glu | Asp | Gln | Ile | Thr | Val | Trp | Gly | Phe | His |
|---|---|---|---|---|---|---|---|---|---|---|---|---|---|---|---|
|  |  |  | 180 |  |  |  |  | 185 |  |  |  |  | 190 |  |  |

| Ser | Asp | Asp | Lys | Thr | Gln | Met | Lys | Lys | Leu | Tyr | Gly | Asp | Ser | Asn | Pro |
|---|---|---|---|---|---|---|---|---|---|---|---|---|---|---|---|
|  |  | 195 |  |  |  |  | 200 |  |  |  |  | 205 |  |  |  |

| Gln | Lys | Phe | Thr | Ser | Ser | Ala | Asn | Gly | Val | Thr | Thr | His | Tyr | Val | Ser |
|---|---|---|---|---|---|---|---|---|---|---|---|---|---|---|---|
|  | 210 |  |  |  |  | 215 |  |  |  |  | 220 |  |  |  |  |

| Gln | Ile | Gly | Asp | Phe | Pro | Asn | Gln | Thr | Glu | Asp | Gly | Gly | Leu | Pro | Gln |
|---|---|---|---|---|---|---|---|---|---|---|---|---|---|---|---|
| 225 |  |  |  |  | 230 |  |  |  |  | 235 |  |  |  |  | 240 |

| Ser | Gly | Arg | Ile | Val | Val | Asp | Tyr | Met | Val | Gln | Lys | Pro | Gly | Lys | Thr |
|---|---|---|---|---|---|---|---|---|---|---|---|---|---|---|---|
|  |  |  |  | 245 |  |  |  |  | 250 |  |  |  |  | 255 |  |

| Gly | Thr | Ile | Val | Tyr | Gln | Arg | Gly | Val | Leu | Leu | Pro | Gln | Lys | Val | Trp |
|---|---|---|---|---|---|---|---|---|---|---|---|---|---|---|---|
|  |  |  | 260 |  |  |  |  | 265 |  |  |  |  | 270 |  |  |

| Cys | Ala | Ser | Gly | Arg | Ser | Lys | Val | Ile | Lys | Gly | Ser | Leu | Pro | Leu | Ile |
|---|---|---|---|---|---|---|---|---|---|---|---|---|---|---|---|
|  |  | 275 |  |  |  |  | 280 |  |  |  |  | 285 |  |  |  |

| Gly | Glu | Ala | Asp | Cys | Leu | His | Ala | Lys | Tyr | Gly | Gly | Leu | Asn | Lys | Ser |
|---|---|---|---|---|---|---|---|---|---|---|---|---|---|---|---|
|  | 290 |  |  |  |  | 295 |  |  |  |  | 300 |  |  |  |  |

| Lys | Pro | Tyr | Tyr | Thr | Gly | Glu | His | Ala | Lys | Ala | Ile | Gly | Asn | Cys | Pro |
|---|---|---|---|---|---|---|---|---|---|---|---|---|---|---|---|
| 305 |  |  |  |  | 310 |  |  |  |  | 315 |  |  |  |  | 320 |

| Ile | Trp | Val | Lys | Thr | Pro | Leu | Lys | Leu | Ala | Asn | Gly | Thr | Lys | Tyr | Arg |
|---|---|---|---|---|---|---|---|---|---|---|---|---|---|---|---|
|  |  |  |  | 325 |  |  |  |  | 330 |  |  |  |  | 335 |  |

| Pro | Pro | Ala | Lys | Leu | Leu | Lys | Glu | Arg |
|---|---|---|---|---|---|---|---|---|
|  |  |  | 340 |  |  |  |  | 345 |

SEQUENCES OF THE HEMAGGLUTININS OF RECENT STRAINS OF INFLUENZA TYPE B VIRUS

BACKGROUND OF THE INVENTION

Influenza type B viruses have been isolated during periods of widespread influenza activity during five of the last ten influenza seasons in the United States. During this time, each major peak of influenza B activity has been associated with the emergence of a new antigenic variant of the virus. As with influenza type A viruses, antigenic drift in influenza type B virus occurs through the accumulation of amino acid changes in the HA1 subunit of the major vital structural glycoprotein, the hemagglutinin (HA).

Analysis of antigenic drift variants of influenza A using molecular modeling techniques has shown that, although the major antigenic domains are clearly identified, nearly the entire outer surface of the globular head region of the HA1 subunit has changed in 10 years. While the structure of the HA of influenza type B viruses appears to be analogous to that of the type A virus HA, the spatial arrangement of the antibody combining sites on the HA of influenza B virus are undetermined since the three-dimensional structure of this protein is uncertain.

Antigenic sites on the HA of influenza type B have been delineated by sequence analysis of both circulating viruses and laboratory derived variants and may not be identical to those of influenza type A viruses. Data from sequencing studies, in conjunction with routine antigenic analysis, helped determine the evolutionary relationships between currently circulating strains of influenza virus. For recent influenza B viruses, at least two main lineages have co-existed since at least 1983. Viruses from each of these two lineages, B/Yamagata/16/88 (B/YM/88) and B/Victoria/2/87 (B/VI/87), had as many as 27 amino acid differences between their HA1 proteins by 1988 and were distinct antigenically. The B/YM/88-like viruses were found to be descendants of viruses similar to an earlier reference strain, B/USSR/100/83, while the B/VI/87-like viruses were related to the more recent epidemic variant, B/Ann Arbor/1/86.

During 1989-1990, influenza B viruses that were antigenically related to both B/VI/87 and B/YM/88 were isolated sporadically throughout the world and comprised less than 1% of the isolates reported in the United States. In spite of this limited circulation, antigenic drift variants were identified from each lineage. During 1990-1991, the majority of influenza isolates in many countries were type B. In the United States, approximately 90% of the reported influenza isolates were type B. Though viruses closely related to both B/VI/87 and B/YM/88 were identified, the majority of these influenza B isolates were antigenically related to a drift variant of B/YM/88, B/Hong Kong/22/89.

Current influenza vaccines typically comprise inactivated whole virus or "split" virus. Split virus is a membrane extract of a whole virus preparation and is usually used in children. The vaccine is produced by growing the virus in eggs, concentrating and purifying the virus, followed by inactivation with formalin. Presently, the vaccine is trivalent and comprises two type A viruses (H3N2 and H1N1 subtypes) and a type B component. B/Hong Kong/22/89, a virus whose sequence is described in this invention, is currently the type B component. The current dose is 45 micrograms ($\mu$g) or 15 $\mu$g of each component and the vaccine is administered intramuscularly. Influenza vaccine is typically given to high risk individuals every year in the late fall. High risk individuals include the elderly and those with chronic upper respiratory tract illness.

Because of antigenic drift of the virus, the viruses used as vaccine components are updated frequently, typically every 2 to 3 years, based on epidemiological data. The invention includes sequence data and antigenic data that can be used to describe a series of field isolates of influenza B. The sequence data would allow, for example, verification that the virus in the vaccine is in fact, B/Hong Kong/22/89. The vaccine manufacturers do not usually sequence their vaccine seed stocks.

The invention characterizes, by molecular and serologic methods, influenza B viruses representative of viruses isolated during the 1989 to 1990 and 1990 to 1991 influenza seasons. Amino acid changes potentially involved in altered antigenic reactivity are identified for both the B/VI/87-like and B/YM/88-like viruses and the genetic relationships between the HA of these drift variants are analyzed. Nucleic acid sequences and amino acid sequences for the viral strains are provided. Methods of vaccination and diagnosis are also included.

SUMMARY OF THE INVENTION

The antigenic and genetic characteristics of the hemagglutinin genes of influenza type B viruses isolated since 1988 during periods of both widespread and sporadic activity were examined using microneutralization tests and direct RNA sequencing. During this time, influenza B viruses representative of two distinct lineages that are antigenically and genetically related to either B/Victoria/2/87 or B/Yamagata/16/88 were isolated.

Sequence analysis of the HA1 domains of representative viruses confirmed the continued existence of two main lineages among recent strains of influenza B and identified unique amino acid changes that could account for the altered antigenic reactivity of some variants. Sequence analysis of the HA2 domains of some of the recent influenza B viruses allowed for a comparison of the evolutionary rates and patterns between the HA1 and HA2 domains.

The invention includes a method for vaccinating a mammal against influenza type B comprising administering an effective amount of a recombinant protein having an antigenic determinant derived from a sequence selected from the group consisting of SEQ. I.D. Nos. 1-26. Preferably, the protein includes an immunodominant region such as amino acids 100-200 from the HA1 domain. The protein is competent to induce a protective immune response to influenza type B in a mammal to which the protein has been administered. The protein can be derived from a nucleic acid sequence selected from the group consisting of SEQ. I.D. Nos. 1-26.

Preferably the effective amount is selected from a range from about 0.1 $\mu$g to about 50 $\mu$g, the administration is parenteral such as intramuscular, and the mammal is a human. A more preferable dosage range is from about 15 $\mu$g to about 45 $\mu$g. Typically, a pharmaceutically appropriate additive, such as a diluent and an adjuvant, is administered concurrently with the protein. Nucleotide sequences and their corresponding amino acid sequences are provided.

Although vaccines of the invention can be prepared recombinantly, they can also be prepared using standard techniques applied to one of the strains sequenced in the invention.

The invention provides a method for identification of a strain of influenza type B comprising selecting a nucleotide sequence from the group consisting of SEQ. I.D. Nos. 1–26, producing a probe derived from the sequence, and using the probe to detect the viral strain. The probe is specific for the sequence under stringent hybridization conditions. The probe can be adapted for various techniques, such as a nucleic acid hybridization technique or a polymerase chain reaction technique.

Also included is a method of diagnosis of an infection of a mammal with influenza type B. This method includes selecting an antigenic determinant encoded by a nucleotide sequence selected from the group consisting of SEQ. I.D. Nos. 1–26, contacting the determinant to a biological sample from the mammal to be evaluated, and observing for a reactivity between the sequence and the serum. This method can be adapted for use in a variety of tests. For example, an enzyme immunoassay can be employed. In this case, a monoclonal antibody to a human immunoglobulin against an influenza B hemagglutinin is preferably used. Other tests are included. For instance, the observation step can include observing for inhibition of hemagglutinin or for fixation of complement. Preferably, the mammal is a human and the sample is selected from the group consisting of throat swab specimens, nasal swab specimens, nasal wash specimens, sputum, tracheal secretions, blood, and serum.

DEFINITIONS

"Antibody" refers to an immunoglobulin molecule able to bind to a specific epitope on an antigen. Antibodies can be a polyclonal mixture or monoclonal. Antibodies can be intact immunoglobulins derived from natural sources or from recombinant sources and can be immunoreactive portions of intact immunoglobulins. Affinity constants of $1 \times 10^8$ liters/mole are preferred. Antibodies may exist in a variety of forms including, for example, Fv, Fab, and $F(ab)_2$, as well as in single chains. (See Huston, et al., *Proc. Nat. Acad. Sci.* U.S.A., 85:5879–5883 (1988) and Bird, et al., Science 242:423–426 (1988), which are incorporated herein by reference. See generally, Hood, et al., "Immunology", Benjamin, N.Y., 2nd ed. (1984), and Hunkapiller and Hood, Nature, 323:15–16 (1986), which are incorporated herein by reference.

"Protein" refers to amino acid sequences, peptides, and polypeptides as well as proteins having tertiary structure.

"Antigen" refers to an entity or fragment thereof which can induce an immune response in a mammal. The term includes immunogens and regions responsible for antigenicity or antigenic determinants.

"Antigenic determinant" refers to a region of immunodominance.

"Complementary" means that one nucleic acid is identical to, or hybridizes selectively to, another nucleic acid. Selectivity of hybridization exists when hybridization occurs that is more selective than total lack of specificity. Typically, selective hybridization will occur when there is at least about 55% identity over a stretch of at least 14–25 nucleotides, preferably at least about 65%, more preferably at least about 75%, and most preferably at least about 90%. See, M. Kanehisa *Nucleic Acids Res.* 12:203 (1984), incorporated herein by reference.

"Isolated" or "substantially pure", when referring to nucleic acids, refers to those that have been purified away from other chromosomal or extrachromosomal DNA or RNA by standard techniques, including alkaline/SDS treatment, CsCl banding, column chromatography, and other techniques well known in the art. See, F. Ausubel, et al., ed. Current *Protocols in Molecular Biology*, Greene Publishing and Wiley-Interscience, New York (1987), incorporated herein by reference.

"Isolated DNA sequence" refers to deoxyribonucleic acid sequences which are cDNA when derived from reverse transcription of a messenger RNA.

"95% amino acid identity" refers to a comparison of the amino acids of two polypeptides which when optimally aligned have approximately 95% of the same amino acids.

"Nucleic acids", as used herein, may be DNA or RNA. Additionally, substantial nucleic acid sequence identity exists when a nucleic acid segment will hybridize, under stringent hybridization conditions, to a complement of another nucleic acid strand.

"Nucleic acid probes" may be RNA or DNA fragments prepared, for example, by digesting plasmid nucleic acid, or by PCR, or synthesized by methods such as the phosphoramidite method described by Beaucage and Carruthers, *Tetrahedron Lett.* 22:1859–1862 (1981), or by the triester method according to Matteucci, et al., *J. Am. Chem. Soc.*, 103:3185 (1981), both incorporated herein by reference. Where a specific nucleic acid sequence is given, it is understood that the complementary strand is also identified and included. The complementary strand will work equally well in situations where the target is a double-stranded nucleic acid.

A nucleic acid probe is complementary to a target nucleic acid when it will anneal only to a single desired position on that target nucleic acid under stringent hybridization conditions, $1\times$ SSC at 65°. Proper annealing conditions depend, for example, upon a probe's length, base composition, and the number of mismatches and their position on the probe, and must often be determined empirically.

For discussions of nucleic acid probe design and annealing conditions, see, for example, Sambrook et al., *Molecular Cloning: A Laboratory Manual* (2nd ed.), Vols. 1–3, Cold Spring Harbor Laboratory, (1989) or *Current Protocols in Molecular Biology*, F. Ausubel et al., ed. Greene Publishing and Wiley-Interscience, New York (1987), both of which are incorporated herein by reference.

"Nucleic acid sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

"Specifically immunoreactive" refers to a binding reaction between an antibody and antigen which is determinative of the presence of the antigen in the presence of a heterogeneous population of proteins and other biologics.

"Substantially pure" as used herein means that the protein is as pure as can be obtained by standard isolation and purification means. Typically this means at least 80% pure as determined by SDS polyacrylamide gel electrophoresis.

BRIEF DESCRIPTION OF THE DRAWINGS

FIG. 5A–D. Shows how restriction endonucleases can be used to differentiate between a prior variant, BTX88 and a new virus B/HK289.

DESCRIPTION OF THE PREFERRED EMBODIMENT

Figure 1:
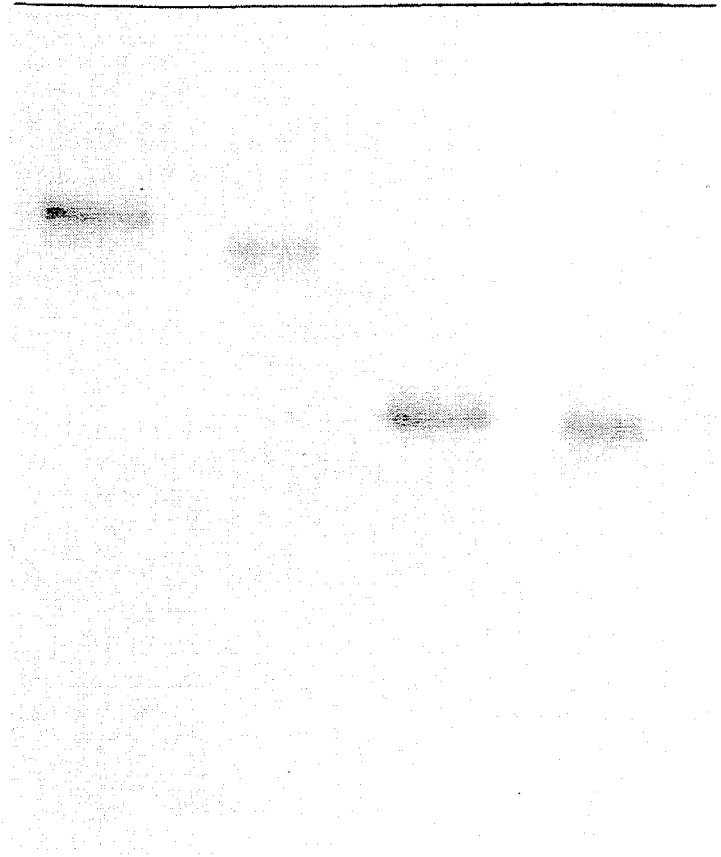
FIG. 1 Electrophoretic analysis of the HAs of influenza B viruses. Preparations of B/IN/89 (lanes 1,3) or B/VI/89 (lanes 2,4) virus were subjected to electrophoresis through 8.0% 4 M urea polyacrylamide gels before being transferred to nitrocellulose and hybridized to rabbit antiserum against influenza B HA. Lanes 3 and 4 show preparations after treatment with Endo F.

This invention relates to isolated nucleic acid sequences encoding viral HA of selected influenza B strains and the gene product, HA types 1 and 2. The nucleic acid compositions, whether RNA, cDNA, or a hybrid of combinations, may be isolated from natural sources or may be synthesized in vitro. The preferred natural sources are the isolates on deposit at the Centers for Disease Control (CDC). See Example 1 and Table 1. The nucleic acids claimed may be present in transformed or transfected whole cells, in a transformed or transfected cell lysate, or in a partially purified or substantially pure form.

Techniques for nucleic acid manipulation of genes encoding HA, such as subcloning nucleic acid sequences encoding polypeptides into expression vectors, labelling probes, nucleic acid hybridization, and the like are described generally, for example in Sambrook et al. (1989) op. cit., or Ausubel et al., ed. (1987) op. cit., both of which are incorporated herein by reference.

Nucleic acid probes for isolating mammalian genes encoding HA are also included in the claimed invention. Such probes are useful for detecting the presence of HA in physiological samples, such as a nasal wash, and as primers for gene amplification using polymerase chain reaction PCR. The nucleic acid probes will usually be at least about 20 nucleotides in length, more typically they will be more than 500 nucleotides in length. The probes preferably include amino acids 100–200 of the HA1 domain.

Alternatively, those of skill may use polymerase chain reaction (PCR) technology to amplify nucleic acid sequences of the HA gene. PCR or other in vitro amplification methods may also be useful, for example, to clone nucleic acid sequences that code for proteins to be expressed, to make nucleic acids to use as probes for detecting the presence of HA or HA mRNA in physiological samples, for nucleic acid sequencing, or for other purposes. For a general overview of PCR see PCR Protocols: *A Guide to Methods and Applications.* (Innis, M, Gelfand, D., Sninsky, J. and White, T., eds.), Academic Press, San Diego (1990), incorporated herein by reference.

The HA gene may be expressed in a recombinantly engineered cell such as bacteria, yeast, filamentous fungal, insect (especially employing baculoviral vectors), and mammalian cells. Those of skill in the art are knowledgeable in the numerous expression systems available for expression of the HA gene. See U.S. Pat. Nos. 4,752,473 and 4,659,669 for expression and purification of HA proteins. Both of these patents are incorporated by reference herein.

Briefly, the expression of natural or synthetic nucleic acids encoding viral HA will typically be achieved by operably linking the gene or portion thereof to a promoter (which is either constitutive or inducible), and incorporated into an expression vector. The vectors are suitable for replication and integration in either prokaryotes or eukaryotes. Typical cloning vectors contain transcription and translation terminators, initiation sequences, and promoters useful for regulation of the expression of the HA gene. The vectors may also comprise generic expression cassettes containing at least one independent terminator sequence, sequences permitting replication of the plasmid in both eukaryotes and prokaryotes, i.e., shuttle vectors, and selection markers for both prokaryotic and eukaryotic systems.

Methods for the expression of cloned genes in bacteria are also well known. In general to obtain high level expression of a cloned gene in a prokaryotic system, it is advisable to construct expression vectors containing a strong promoter to direct mRNA transcription termination. The inclusion of selection markers in DNA vectors transformed in *E. coli* is also useful. Examples of such markers include genes specifying resistance to ampicillin, tetracycline, or chloramphenicol. See Sambrook for details concerning selection markers and promoters for use in *E. coli.* Suitable eukaryote hosts may include plant cells, insect cells, mammalian cells, yeast, and filamentous fungi.

The protein encoded by the HA gene which is produced by recombinant technology may be purified by standard techniques well known to those of skill in the art. Recombinantly produced HA can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired HA.

The purified HA when described as "isolated" or and "substantially pure" describes a protein that has been separated from components which naturally accompany it. Typically, a monomeric protein is substantially pure when at least about 85% or more of a sample exhibits a single polypeptide backbone. Minor variants or chemical modifications may typically share the same polypeptide sequence. Depending on the purification procedure, purities of 85%, and preferably over 95% pure are possible. Protein purity or homogeneity may be indicated by a number of means well known in the art, such as polyacrylamide gel electrophoresis of a protein sample, followed by visualizing a single polypeptide band on a polyacrylamide gel upon staining. For certain purposes high resolution will be needed and HPLC or a similar means for purification utilized.

The proteins of this invention may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: New York (1982), incorporated herein by reference.

The present invention also provides methods for detecting the presence or absence and certain types of HA in a physiological specimen. One method involves a Southern transfer and is well known to those of skill in the art. Hybridization is carried out using probes. Visualization of the hybridized portions allows the qualitative determination of the presence or absence of HA genes.

Similarly, a Northern transfer may be used for the detection of HA message in samples of RNA. This procedure is also well known in the art. See, Maniatis, et al., *Molecular Cloning: A laboratory manual*, Cold Spring Harbor Laboratory, Cold Spring Harbor, N.Y. (1982). In brief, the mRNA is isolated from a given cell sample using an acid guanidinium-phenol-chloroform extraction method. The mRNA is then electrophoresed to separate the mRNA species and the mRNA is transferred from the gel to a nitrocellulose membrane. As with the Southern blots, labeled probes are used to identify the presence or absence of the HA transcript.

An alternative means for determining the level of expression of the HA gene is in situ hybridization. In situ hybridization assays are well known and are generally described in Angerer, etal., *Methods Enzymol.*, 152:649–660 (1987). In an in situ hybridization cells are fixed to a solid support, typically a glass slide. The cells are then contacted with a hybridization solution at a moderate temperature to permit annealing of HA specific probes that are labelled. The probes are preferably labelled with radioisotopes or fluorescent reporters.

In addition to the detection of HA genes using nucleic acid hybridization technology, one can use immunoassays to qualitatively and quantitatively evaluate HA. A general overview of the applicable technology is in Harlow and Lane, *Antibodies: A Laboratory Manual*, Cold Spring Harbor Pubs., N.Y. (1988). In brief, HA or a fragment thereof is expressed in transfected cells, preferably bacterial cells, and purified as generally described above. The product is then injected into a mammal capable of producing antibodies. Either monoclonal or polyclonal antibodies specific for the gene product can be used in various immunoassays. Such assays include competitive immunoassays, radioimmunoassays, Western blots, ELISA, indirect immunofluorescent assays and the like. For competitive immunoassays, see Harlow and Lane (1988) at pages 567–573 and 584–589.

Monoclonal antibodies may be obtained by various techniques familiar to those skilled in the art. Briefly, spleen cells from an animal immunized with a desired antigen are immortalized, commonly by fusion with a myeloma cell (see, Kohler and Milstein, *Eur. J. Immunol.* 6:511–519 (1976), incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host.

Hemagglutination Inhibition (HI) and Complement Fixation (CF) are two laboratory tests most frequently used to detect infection with an influenza virus by testing for the presence of antibodies against the virus or antigens of the virus. HI is based on the observation that viral hemagglutination will not occur if antibody specific for the virus is added before addition of red blood cells. The inhibition is specific and is useful for vital identification and antibody determination.

Hemagglutination is a sensitive semiquantitative technique involving the agglutination by antibodies of red blood cells coated with an antigen which is not endogenous to the red cell surface. See Paul, W., *Fundamentals of Immunology*, Raven Press, 2d (1989) at 343–344. Untreated red blood cells do not normally agglutinate. Following treatment with tannic acid (0.02 mg/ml for 10 min at 37° C.), however, they clump readily.

Untreated red blood cells are coated with polysaccharide antigens. Antigen purity is important for the absorption step since impurities may compete for protein-binding sites. After tanning and absorption, the red blood cells are stored in 1% serum solution to prevent spontaneous aggregation. If tanning does not work, chromic chloride treatment facilitates adsorption of some protein antigens. Also, covalent attachment of antigens to the cell surface has been achieved through bivalent cross-linking reagents such as bis diazobenzidine or glutaraldehyde, or through carbodiimide intermediates.

Testing for specific antibodies is done by serially diluting the antiserum in the wells of a microtiter plate. 0.1 ml of 1% solution of antigen-coated red cells is added. After mixing, the red cells are allowed to settle for 2 hr. In the presence of specific 2antibodies, agglutinated cells settle evenly on the bottom of the well. Unagglutinated red cells slide down the sides and form a button at the very bottom of the well. The liter of a sample is the highest dilution at which definite agglutination occurs. Agglutinated cells form a fragile network that can even be resuspended after settling, and they give the same end-point on resettling. To assure antigen specificity, the antiserum is absorbed against uncoated red cells before the assay, and an uncoated red cell control is included with each assay. This test is advantageous because it is more sensitive than immunoprecipitation.

Once the titer of an antiserum is determined, its interaction with antigen-coated red blood cells can be used as a sensitive assay for antigen. Antibody is diluted to a concentration twofold higher than the limiting concentration producing agglutination. Varying amounts of free antigen are added to constant amounts of antibody. Agglutination is inhibited when at least half of the antibody sites are occupied by free antigen. Similarly, the agglutination of antigen-coated red cells by antibody can be inhibited by prior incubation of antibody with anti-idiotype antiserum. This provides a sensitive assay for the detection and quantitation of anti-idiotype antibodies that react with the variable region of antibodies and sterically block antigen binding.

The serological methods are useful when one wishes to detect antibody to a specific variant. For example, one may wish to see how well a vaccine recipient has responded to the new variant. Alternatively, one may take serum from a patient to see which variant the patient responds to the best. The CF and ELISA tests, in the present standard configurations, are designed to detect conserved antigens and cannot differentiate between variants. The serological tests most applicable here are HI and microneutralization, Other diagnostic methods are included. Diagnosis is made by detection of infectious virus or viral antigen in secretions from patients or the detection of a serum antibody response. Diagnosis by PCR or hybridization can be done on virus growing in cell culture or on clinical material. Influenza virus is readily isolated from throat or nasal swab specimens, sputum, or tracheal secretion specimens in the first two or three days of illness. Usually infectivity is detected within 48 to 72 hours in .monkey kidney cell cultures. Viral antigen may be detected more rapidly in such specimens by use of immunofluorescence or ELISA. Serologic methods may require a convalescent sera obtained 10 to 14 days after the onset of infection and they are of great use in epidemiologic studies and to document the occurrence of an outbreak. A four-fold increase in antibody titer comparing an acute to convalescent phase is diagnostic. The complement fixation antibody test is not dependent on strain or subtype variation in contrast to hemagglutination inhibition.

Hybridization can be employed using primers constructed from sequences of the invention. Hybridization techniques can be used to detect vital RNA in cell culture or clinical samples. Based on these sequences, probes which differentiate between the strains under stringent hybridization conditions can be constructed. Additionally, cDNA prepared from vital RNA could be amplified by PCR. Because PCR amplifies DNA, a cDNA is first made set of primers for the HA gene. The sequence data herein allows the PCR products to be characterized by either restriction endonuclease (RE) cleavage or Southern blotting. Specific cleavage by RE whose sites are predicted by the sequence data is feasible. See, for example, FIG. 5AB which shows how RE can be used to differentiate between a prior variant, BTX88 and a new virus B/HK289. Finally, Southern blotting of the PCR products can be accomplished and hybridization described herein.

The invention also provides substances suitable for use as vaccines against the specified strains of influenza type B as well as methods for vaccination. Vaccines can be made recombinantly. Typically, a vaccine will include from about 1 to about 50 micrograms of antigen or antigenic protein. More preferably, the amount of protein is from about 15 to about 45 micrograms. Typically, the vaccine is formulated so that a dose includes about 0.5 milliliters. The vaccine may be administered by any route known in the art. Preferably, the route is parenteral. More preferably, it is subcutaneous or intramuscular.

There are a number of strategies for amplifying an antigen's effectiveness, particularly as related to the art of vaccines. For example, cyclization or circularization of a peptide can increase the peptide's antigenic and immunogenic potency. See U.S. Pat. No. 5,001,049 which is incorporated by reference herein. More conventionally, an antigen can be conjugated to a suitable carrier, usually a protein molecule. This procedure has several facets. It can allow multiple copies of an antigen, such as a peptide, to be conjugated to a single larger carrier molecule. Additionally, the carrier may possess properties which facilitate transport, binding, absorption or transfer of the antigen.

For parenteral administration, such as subcutaneous injection, examples of suitable carriers are the tetanus toxoid, the diphtheriatoxoid, serum albumin and lamprey, or keyhole limpet, hemocyanin because they provide the resultant conjugate with minimum genetic restriction. Conjugates including these universal carriers can function as T cell clone activators in individuals having very different gene sets.

The conjugation between a peptide and a carrier can be accomplished using one of the methods known in the art. Specifically, the conjugation can use bifunctional cross-linkers as binding agents as detailed, for example, by Means and Feeney, "A recent review of protein modification techniques" *Bioconjugate Chem.* 1:2-12 (1990).

Vaccine delivery systems also include live vaccines based on recombinant poxviruses, adenoviruses or mycobacteria, such as BCG. Also included are live influenza vaccines based on reassortments between the field isolates described herein and a cold-adapted influenza B donor strain. These reassortants contain the HA from the field isolate and the internal genes from the attenuated vaccine donor strain.

The antigen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionobacterium aches), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Mich.). Other suitable adjuvants are Amphigen (oil-in-water), Alhydrogel (aluminum hydroxide), or a mixture of Amphigen and Alhydrogel. Only aluminum is approved for human use.

The proportion of antigen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the antigen can range from about 0.1 $\mu$g to about 100 $\mu$g protein per patient. A preferable range is from about 1 $\mu$g to about 50 $\mu$g per dose. A more preferred range is about 15 $\mu$g to about 45 $\mu$g. A suitable dose size is about 0.5 ml. Accordingly, a dose for intramuscular injection, for example, would comprise 0.5 ml containing 45 μg of antigen in admixture with 0.5% aluminum hydroxide. After formulation, the vaccine may be incorporated into a sterile container which is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intramuscular) injection. Intramuscular administration is preferred. The treatment may consist of a single dose of vaccine or a plurality of doses over a period of time. The antigen of the invention can be combined with appropriate doses of compounds including other influenza antigens, such as influenza type A antigens. Also, the antigen could be a component of a recombinant vaccine which could be adaptable for oral administration.

Vaccines of the invention may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is simple and routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions within the natural amino acid sequence for HA. For example, it is known in the protein art that certain amino acid residues can be substituted with amino acids of similar size and polarity without an undue effect upon the biological activity of the protein. HA has significant tertiary structure and the epitopes are usually conformational. Thus, modifications should generally preserve conformation to produce a protective immune response.

This invention further embraces diagnostic kits for detecting the presence of HA in tissue samples, such as serum, comprising a containers containing anti-HA antibodies and instructional material for performing the test.

The invention describes the genetic and antigenic changes that occurred in the HAs of B/VI/87- and B/YM/88-like viruses during the 1989–90 and 1990–91 seasons. The invention demonstrates that two distinct lineages of influenza B virus have persisted and have caused disease for at least four years.

Within the HA1s of viruses from each of the main lineages, amino acid differences that could account for altered antigenic reactivity were sometimes apparent. The amino acid change that had the greatest effect on antigenicity was the glycine to arginine change at position 141 in B/IN/89. The changes at positions 76, 122, and 150 that were observed in the HA1s of the B/HK289-like viruses occurred in regions analogous to antigenic sites E, A, and B, respectively, of the influenza A (H3) HA. Aminoacid changes at positions 76 and 150 were unique to recent B/HK289-like influenza B viruses.

While the majority of amino acid changes from viruses on both lineages occurred in regions analogous to antigenic sites A, B and E of the influenza type A (H3) viruses, the B/YM/88-like viruses had more changes at amino acids 202, 203, 230 and 298 than the B/VI/87-like viruses did. These amino acids may be located in a region of the HA1 of influenza B viruses that is analogous to the trimer interface region (site D) of the influenza A HA. The antigenic presentation of these amino acids on the B/YM/88-like HA1s may be affected by a nearby potential glycosylation site at positions 233–235 that is not present on any of the B/VI/87-like HA1s.

The rate of nucleotide change for HA1 of field strains of influenza B is 0.22 to 0.23% per year for viruses 12 to 18 years apart. Thus, the mutation rate for HA1 of the influenza B viruses is approximately 30% less than those calculated for the HA1 of influenza type A viruses when the time span between the isolation dates of the viruses included in the data set are similar. When B/Lee/40 is used as the root virus, however, the rate that can be calculated (0.11% per year) is approximately 300% less than those of influenza type A but similar to those previously described for influenza B. Because B/Lee/40 has an extensive passage history, it may be advantageous to base calculations of mutation rates on the sequences of viruses that are more representative of past epidemic variants.

The sequence analysis of a limited number of influenza type B HA2 domains indicated that while the rate of nucleotide substitution was similar for both the HA1 and HA2 domains, the rate of amino acid change was much lower for the HA2. This could indicate that there are more rigid structural constraints for this domain or that this domain is less susceptible to selective pressure by antibody.

EXAMPLES

Example 1

Viruses. The influenza B viruses used in this study were submitted to the World Health Organization Collaborating Center for Influenza, Influenza Branch, Centers for Disease Control (CDC), Atlanta, GA, for reference antigenic analysis between 1989 and 1991. The strain designation, accession number for the HA1 sequence, collection date, and serological identification by hemagglutination inhibition (HI) of these viruses are given in Table 1. The earlier strains of influenza B used in this study were: B/Beijing/1/87 (B/BJ/87), B/Victoria/2/87 (B/VI/2/87), B/Texas/37/88 (B/TX/88), B/Yamagata/16/88 (B/YM/88). The relationships of the HA1 sequences of these earlier viruses has been described previously. Rota, P.A., Wallis, T.R., Harmon, M.W., Rota, J.S., Kendal, A.P., & Nerome, K., "Cocirculation of two distinct evolutionary lineages of influenza type B virus since 1983," *Virology* 175:59–68 (1990).

Viruses were propagated at low multiplicity of infection in the allantoic cavity of 10 to 11 day old embryonated chicken eggs at 34° C. for 2 days. All viruses had been passaged in eggs four to six times.

Virion purification and RNA extraction. Allantoic fluid was harvested and clarified by centrifugation (15,000×g, 4° C., 10 min). The virions were pelleted by centrifugation (17,000 rpm, Type 19 rotor, 4° C., 3 hr, Beckman Instruments, Palo Alto, CA). The pellet was resuspended in TSE (0.01 M Tris-HCl, pH 7.8, 0.1 M NaCl, 0.001 M EDTA), homogenized by 4–5 passages through a 22-gauge needle and pelleted by centrifugation at 24,000rpm, SW 28 (rotor at 4° C. for 90 minutes), (Beckman Instruments, Palo Alto, CA) through 30% (wt/vol) sucrose in TSE onto a60% (wt/vol) sucrose in TSE cushion.

The virus band at the 30–60% sucrose interface was collected, diluted in TSE and pelleted by centrifugation (25,000 rpm, SW 28 rotor, at 4° C., for 60 minutes). The virus was resuspended in 0.5 ml of sterile distilled water and stored at −70° C. The RNA was extracted from purified virions using the method described by Palese, P. and Schulman, J.L., "Differences in RNA Patterns of Influenza A Viruses", J. Virol. 17:876–884 (1976). The purified RNA was resuspended in a small volume of sterile distilled water and stored at −70° C. RNA concentrations were determined by ultraviolet spectroscopy.

TABLE 1

INFLUENZA B ISOLATES FROM 1989 TO 1991

| STRAIN | ABBREV. | ACCESSION. NO. | COLL. DATE | ID |
|---|---|---|---|---|
| B/Guangdong/55/89 | B/GD/89 | M65166 | 8/89 | YM |
| B/Hong Kong/9/89 | B/HK/89 | M65169 | 8/89 | YM |
| B/Hong Kong/22/89 | B/HK289 | M65167 | 11/89 | YM |
| B/Victoria/103/89 | B/VI103 | M65176 | 11/89 | YM |
| B/South Dakota/5/89 | B/SD/89 | M65172 | 12/89 | YM |
| B/India/3/89 | B/IN/89 | M65168 | 4/89 | ? |
| B/Victoria/19/89 | B/VI/89 | M65177 | 11/89 | VI |
| B/Paris/329/89 | B/PS/89 | M65173 | 12/89 | VI |
| B/Panama/45/90 | B/PN/90 | M65171 | 3/90 | YM |
| B/Texas/4/90 | B/TX/90 | M65175 | 11/90 | YM |
| B/New York/3/90 | B/NY/90 | M65170 | 11/90 | YM |
| B/Bangkok/163/91 | B/BK/91 | M65165 | 1/91 | YM |
| B/Texas/1/91 | B/TX/91 | M65174 | 1/91 | YM |

ID: viruses were identified as being antigenically related to either B/YM/88 (YM) or B/VI/87 (VI) by hemagglutination inhibition with post-infection ferret antiserum.

Example 2

Antigenic analysis of viruses. The antigenic characteristics of the viruses were analyzed with postinfection ferret serum using both HI and microneutralization assays. See Palmer, D.F., Dowdle. W.R., Coleman, M.T., & Schild, G.C., "Advanced laboratory techniques for influenza diagnosis," U.S. Dept. of Health, Education and Welfare (Immunology ser. no. 6), Centers for Disease Control, Atlanta (1976); and Harmon, M.W., Rota, P.A., Walls, H.H. & Kendal, A.P., "Antibody response in humans to influenza virus type B host-cell-derived variants after vaccination with standard (egg-derived) vaccine or natural infection," J. Clin. Microbiol. 26:333–337 (1988).

Antigenic analysis of influenza B isolates. Recently isolated influenza B viruses were initially identified as being most closely related to B/YM/88 or B/VI/87 using HI assays and strains that were representative of recently circulating influenza B viruses were chosen for further analysis. See Table 1. Though other viruses antigenically similar to B/IN/89 were not isolated, this virus was,included because it had unique antigenic characteristics. More B/YM/88-like viruses were included as they were representative of the majority of viruses isolated during the period of widespread influenza B activity in 1990–91, while B/VI/87-like viruses accounted for less than 3% of influenza B virus isolates in the United States in 1990–91. Centers for Disease Control, "Update: Influenza—United States and worldwide and composition of the 1991–1992 influenza vaccine, Morbid. Mortal. Wkly. Rpt. 40:231–239 (1991). Nearly 65 percent of the B/YM/88-like viruses isolated during 1990–1991 were further classified as being antigenically more similar to a minor variant, B/HK289, by HI tests. Centers for Disease Control, "Update: Influenza—United States and worldwide and composition of the 1991–1992 influenza vaccine, Morbid. Mortal. Wkly. Rpt. 40:231–239 (1991).

The antigenic properties of the influenza B isolates were also examined by using the microneutralization test. See Table 2. This procedure is more sensitive than HI for the detection of low levels of antibody to influenza B virus (Harmon, M.W., Rota, P.A., Walls, H.H. & Kendal, A.P., "Antibody response in humans to influenza virus type B host-cell-derived variants after vaccination with standard (egg-derived) vaccine or natural infection," J. Clin. Microbiol. 26:333–337 (1988)). Post-infection ferret antiserum to B/BJ/87, a virus which is antigenically and genetically very similar to B/VI/87 (Rota, P.A., Wallis, T.R., Harmon, M.W., Rota, J.S., Kendal, A.P., & Nerome, K., "Cocirculation of two distinct evolutionary lineages of influenza type B virus since 1983," Virology 175:59–68 (1990)), was used in the miconeutralization tests since it had higher homologous titers than serum to B/VI/87. Table 2 shows the same pattern of antigenic differences between the B/YM/88- and B/VI/87-like viruses that was observed in the HI tests.

The results of the microneutralization tests also confirmed that drift variants had arisen among the B/YM/88-like viruses with B/HK289, B/PN/90 and B/BK/91 showing the greatest amount of antigenic change. See Table 2. These viruses had an eight-fold drop in titer against the antiserum to B/YM/88. B/HK289 and B/PN/90 were more related to each other than to B/BK/91. Other viruses including B/HK/89, B/GD/89, B/SD/89, B/TX/90, B/NY/90, and B/TX/91 had very low or no drop in titer against the antiserum to B/YM/88 and had similar reactivity patterns to each other. The B/VI/87-like viruses were antigenically homogeneous from 1987–1989. B/IN/89 had unique antigenic characteristics and showed little cross-reactivity with any the influenza B viruses tested.

TABLE 2

ANTIGENIC DRIFT OF INFLUENZA TYPE B VIRUSES: 1989–1991

Neutralization titer with post infection ferret antiserum to:

| STRAIN | B/YM/88 | B/HK289 | B/PN/90 | B/BJ/87 | B/IN/89 |
|---|---|---|---|---|---|
| B/YM/88 | 1280 | 320 | 320 | 40 | 15 |
| B/HK/89 | 1280 | 480 | 1920 | 80 | 20 |
| B/GD/89 | 640 | 240 | 960 | 40 | 10 |
| B/TX/91 | 1920 | 160 | 320 | 80 | 10 |
| B/SD/89 | 480 | 160 | 960 | 30 | 10 |
| B/TX/90 | 960 | 160 | 640 | 80 | 20 |
| B/NY/90 | 480 | 80 | 1280 | 40 | 10 |
| B/BK/91 | 160 | 120 | 320 | 40 | 60 |
| B/VI103 | 640 | 80 | 160 | 20 | 10 |
| B/HK289 | 160 | 160 | 960 | 10 | 10 |
| B/PN/90 | 160 | 160 | 1280 | 10 | 10 |
| B/VI/87 | 10 | 20 | 20 | 640 | 40 |
| B/BJ/87 | 10 | 10 | 10 | 320 | 40 |
| B/TX/88 | 10 | 10 | 10 | 160 | 20 |
| B/VI/89 | 10 | 10 | 10 | 160 | 10 |
| B/PS/89 | 10 | 15 | 40 | 240 | 20 |
| B/IN/89 | 10 | 40 | 40 | 60 | 160 |

Neutralization assays were performed using post-infection ferret serum as described by Harmon et al., 1988.

Example 3

RNA sequencing. The nucleotide sequences of the HA1 gene were determined by direct RNA sequencing using the dideoxy chain-termination method. See Sanger, F., Nicklen, S., & Coulson, A.R., "DNA sequencing with chain terminating inhibitors," *Proc. Natl. Acad. Sci. USA* 74:5463–5467 (1977). The method was modified for RNA templates. See Air, G.M., "Nucleotide sequence coding for the 'signal peptide' and N terminus of the hemagglutinin from an Asian (H2N2) strain of influenza virus," *Virology* 97:468–472 (1979). Terminal deoxynucleotidyl transferase was added to the chase mixture to help eliminate stops. See DeBorde, D.C., Naeve, C.W., Herlocher, M.L., & Maassab, H.F., "Resolution of a common RNA sequencing ambiguity by terminal deoxynucleotidyl transferase," *Anal. Biochem.* 157:275–282 (1986). Purified virion RNA (2 ug) served as template and synthetic oligonucleotides were used to prime cDNA synthesis with AMV reverse transcriptase (Life Sciences Inc., Tampa, Fla.). The sequencing primers used in this study were identical to those described previously. See Rota, P.A., Wallis, T.R., Harmon, M.W., Rota, J.S., Kendal, A.P., & Nerome, K., "Cocirculation of two distinct evolutionary lineages of influenza type B virus since 1983," *Virology* 175:59–68 (1990).

Computer analyses of nucleotide sequences. Sequence data were analyzed by using version 7.0 of the sequence analysis software package of the University of Wisconsin Genetics Computer Group. See Devereaux, J., Haeberli, P., & Smithies, O., "A comprehensive set of sequence analysis programs for the VAX," *Nucleic Acids Res.* 12:387–395 (1984). Version 3.4 of the Phylogeny Inference Package was also used. Felsenstein, J., "Phylogenies from molecular sequences: inferences and reliability", *Am. Rev. Genet.* 22:512–565 (1988). Both programs were run on a VAX computer (Digital Equipment Corp.). Evolutionary trees for the influenza B viruses were also constructed with the aid of a sequence comparison program, Tree, developed by Gerald Ebert (GAE Software, Avondale Estates, GA).

Sequence analysis. To further characterize the influenza type B isolates, the nucleotide and deduced amino acid sequences were determined for the coding regions of the HA1 domains of the HA genes of the B/YM/88-like and B/VI/87-like viruses listed in Table 1. The number of nucleotide and amino acid changes between any two of the viruses is shown in Table 3. Recently co-circulating viruses from separate lineages had as many as 83 (8.7%) nucleotide and 34 (9.1%) amino acid changes between them. The group of B/YM/88-like viruses differed by as many as 10 amino acids in HA1 and were more genetically diverse than the recent B/VI/87-like viruses. Sequence analysis indicated that B/IN/89 was clearly related to the B/VI/87-like viruses.

Table 4A–D shows the complete deduced amino acid sequences for the HA1 coding regions of the recent influenza B isolates compared to the HA1 sequences of either B/VI/87 or B/YM/88. Sequences begin with the first amino acid after signal peptide cleavage and end at the HA1–HA2 cleavage site. Period (.) indicates amino acid deletion. A description of the nucleotide and amino acid differences between the HA1s of B/VI/87 and B/YM/88 has been presented previously. Rota, P.A., Wallis, T.R., Harmon, M.W., Rota, J.S., Kendal, A.P., & Nerome, K., "Cocirculation of two distinct evolutionary lineages of influenza type B virus since 1983," *Virology* 175:59–68 (1990). The majority of the more recent influenza B viruses from both lineages had amino acid changes at positions 73, 197 and 199. At some amino acid residues, changes appeared to be limited to one lineage. For example, all of the recent B/VI/87-like viruses had an amino acid change (V to I) at residue number 137 while the majority of recent B/YM/88-like viruses had changes at positions 150, 203, 230, and 298. Viruses from both lineages had a majority of the amino acid changes between positions 100–200. This region includes the previously proposed immunodominant region of the HA of influenza B virus. Berton, M.T., & Webster, R.G., "The antigenic structure of the influenza B virus hemagglutinin: Operational and topographical mapping with monoclonal antibodies," *Virology* 143:583–594 (1985). The B/YM/88-like viruses had 2 or 3 changes in the region of amino acids 200–300 in contrast to the B/VI/87-like viruses which had 0 or 1.

From the alignment of predicted amino acid changes in the HA1 domains of these viruses (Table 4A-D), changes that could have accounted for the differences in antigenic reactivity were identified. Compared to the other B/VI/87-like viruses, B/IN/89 had a single unique amino acid change at position 141. Among the B/YM/88-like viruses showing the greatest antigenic drift, it was observed that B/HK289 and B/PN/90 shared unique amino acid changes at positions 76 and 122, while B/BK/91 had unique changes at positions 149 and 217.

Glycosylation site at amino acids 197–199. Among isolates of influenza B, amino acids 197 and 199, which contain a potential glycosylation site, display a considerable amount of heterogeneity. It has been reported that clinical specimens of influenza B and influenza B virus passaged in mammalian cells retain this glycosylation site while viruses passaged in eggs lose this site.

Figure 2:
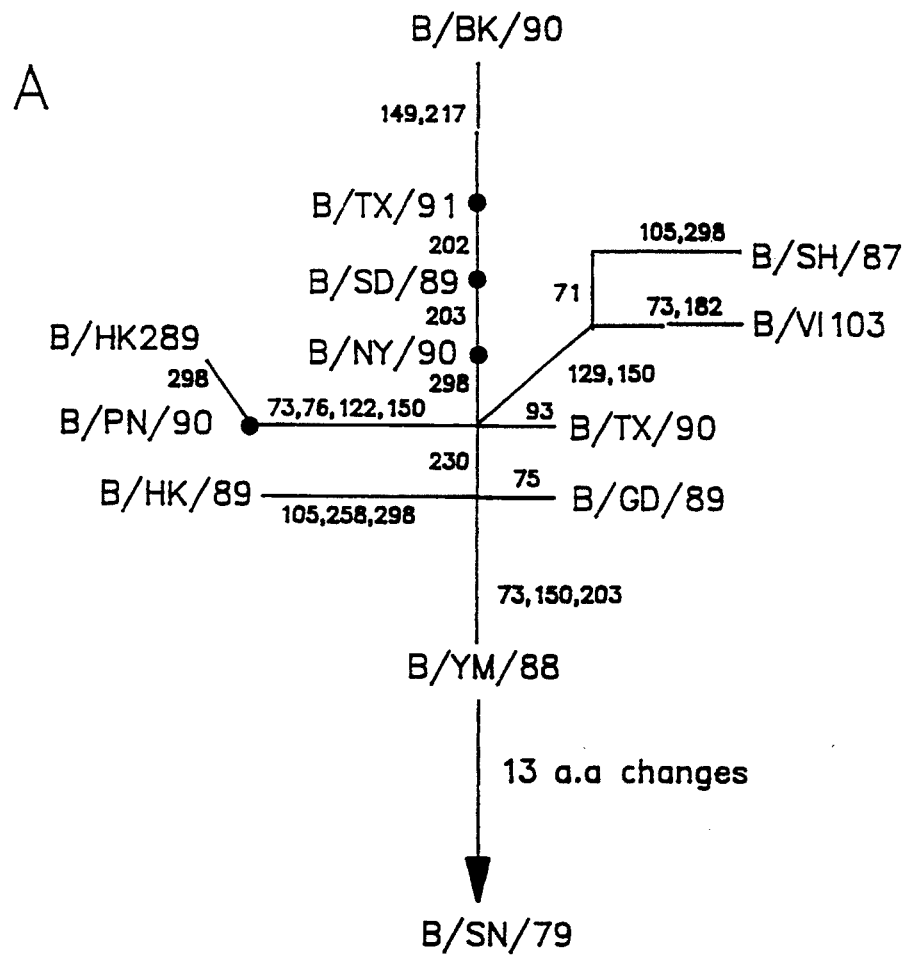
FIG. 2 Evolutionary relationships of recent B/YM/88-like (panel A) or B/VI/87-like (panel B) isolates of influenza B. Scale is based on the number of amino acid changes between viruses. Tree was drawn using the TREE program as described in Methods. Numbers of changed amino acid residues are shown along each branch. Amino acids 197 and 199 are not shown. Sequences from previous reports are: SN79: B/Singapore/222/79; SH87: B/Shanghai/12/87, VI87, YM88, BJ87, TX88.
Figure 2:
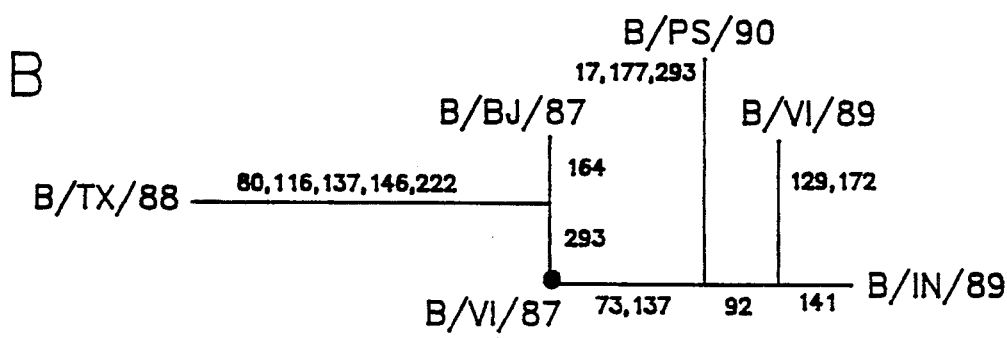

By sequencing RNA purified from egg-passaged virus, data of the invention indicated that several of these viruses had retained the potential glycosylation site at amino acids 197–199 (Table 4A-D). In order to determine if this site was utilized in these viruses, the HAs of viruses (B/IN/89, B/VI/89, B/NY/90 and B/TX/91, B/HK289 and B/PN/90) which had very similar HA1 sequences, but differed at this predicted glycosylation site, were analyzed by SDS-PAGE and Western blotting. The HAs from only one pair of related viruses, B/IN/89 and B/VI/89, Which differed by 4 amino acids showed differences in apparent molecular weight similar to those previously described for egg- and MDCK cell- derived viruses which differed by one potential glycosylation site. See Robertson, J.S., Naeve, C.W., Webster, R.G., Bootman, J.S., Newman, R., & Schild, G.C., "Alterations in the hemagglutinin associated with adaptation of influenza B virus to growth in eggs," *Virology* 143:166–174 (1985). This migrational difference was not observed after the HAs were treated with endotoxin F (Endo F). See FIG. 2. Therefore, the additional glycosylation site at aminoacids 197–199 was apparently maintained and utilized in some egg-derived viruses. No changes in potential glycosylation were observed in other regions of HA1 for the viruses in this study.

TABLE 3

Number of nucleotide (below diagonal) and amino acid (above diagonal) changes between recent influenza type B viruses.

|    |         | 1  | 2  | 3  | 4  | 5  | 6  | 7  | 8  | 9  | 10 | 11 | 12 | 13 | 14 | 15 | 16 | 17 |
|----|---------|----|----|----|----|----|----|----|----|----|----|----|----|----|----|----|----|----|
| 1. | B/SN/79 | 0  | 15 | 15 | 19 | 18 | 17 | 18 | 17 | 16 | 18 | 18 | 16 | 18 | 19 | 21 | 20 | 22 |
| 2. | B/YM/88 | 36 | 0  | 5  | 7  | 4  | 8  | 6  | 9  | 6  | 7  | 6  | 7  | 26 | 27 | 30 | 29 | 31 |
| 3. | B/SD/89 | 37 | 14 | 0  | 8  | 6  | 5  | 5  | 5  | 2  | 7  | 4  | 3  | 25 | 27 | 29 | 28 | 30 |
| 4. | B/VI103 | 37 | 11 | 15 | 0  | 8  | 8  | 10 | 10 | 6  | 6  | 6  | 8  | 29 | 27 | 30 | 30 | 30 |
| 5. | B/GD/89 | 38 | 10 | 14 | 11 | 0  | 8  | 5  | 10 | 5  | 7  | 5  | 8  | 29 | 30 | 33 | 32 | 34 |
| 6. | B/HK289 | 38 | 15 | 15 | 12 | 15 | 0  | 7  | 10 | 5  | 2  | 7  | 8  | 28 | 30 | 32 | 31 | 33 |
| 7. | B/HK/89 | 38 | 13 | 13 | 14 | 11 | 14 | 0  | 10 | 5  | 9  | 7  | 8  | 28 | 30 | 33 | 32 | 34 |
| 8. | B/BK/91 | 39 | 15 | 9  | 16 | 15 | 18 | 16 | 0  | 5  | 10 | 7  | 3  | 28 | 27 | 29 | 29 | 30 |
| 9. | B/NY/90 | 39 | 15 | 7  | 14 | 13 | 16 | 14 | 10 | 0  | 5  | 2  | 3  | 27 | 27 | 29 | 28 | 30 |
| 10.| B/PN/90 | 39 | 13 | 17 | 10 | 13 | 4  | 16 | 18 | 16 | 0  | 5  | 8  | 30 | 30 | 32 | 31 | 33 |
| 11.| B/TX/90 | 39 | 13 | 11 | 12 | 11 | 16 | 14 | 12 | 10 | 14 | 0  | 5  | 29 | 29 | 31 | 30 | 32 |
| 12.| B/TX/91 | 39 | 17 | 11 | 18 | 17 | 20 | 18 | 9  | 12 | 20 | 8  | 0  | 27 | 26 | 27 | 28 | 29 |
| 13.| B/VI/87 | 40 | 65 | 63 | 64 | 65 | 66 | 66 | 68 | 68 | 68 | 68 | 68 | 0  | 4  | 7  | 5  | 7  |
| 14.| B/BJ/87 | 47 | 71 | 73 | 68 | 71 | 74 | 74 | 74 | 74 | 74 | 74 | 73 | 16 | 0  | 8  | 7  | 5  |
| 15.| B/VI/89 | 47 | 72 | 72 | 71 | 72 | 75 | 75 | 74 | 75 | 75 | 75 | 72 | 13 | 19 | 0  | 4  | 7  |
| 16.| B/IN/89 | 48 | 73 | 73 | 72 | 73 | 76 | 76 | 76 | 76 | 76 | 76 | 75 | 13 | 15 | 10 | 0  | 5  |
| 17.| B/PS/89 | 55 | 80 | 80 | 77 | 80 | 83 | 83 | 83 | 83 | 82 | 83 | 82 | 21 | 15 | 20 | 14 | 0  |

Example 4

Electrophoretic analysis of hemagglutinins. Samples were prepared by adding 1/10th volume of 10× digestion buffer (0.5 M NaAc, 0.1 M EDTA, 1% SDS) to clarified allantoic fluid containing virus followed by heating at 65° C. for 3 minutes. Treated samples received 4 units of Endo F (endoglycosidase F/N-glycosidase F, Boerhringer Mannheim, Indianapolis, IN) before being incubated at 37° C. for 1 hour. Endo F-treated and mock-treated samples were subjected to electrophoresis through 8% SDS-polyacrylamide gels containing 4M urea. After electrophoresis, proteins were transferred to nitrocellulose filters and the HAs were detected by hybridization to monospecific rabbit antiserum against the HA of influenza B as described previously. See Rota, P.A., Shaw, M.W., & Kendal, A.P., "Comparison of the immune response induced to variant influenza type B hemagglutinins expressed in vaccinia virus," Virology 161:269-275 (1987).

Example 5

Evolutionary relationships. The evolutionary relationships based on the amino acid differences between the recent influenza B viruses were determined separately for the B/YM/88- and B/VI/87-like viruses using either B/YM/88 or B/VI/87 as the anchor sequence. See FIG. 2. The antigenically variant B/HK289 and B/PN/90 viruses were placed on a separate lineage from the remainder of the B/YM/88-like viruses. Another sub-lineage included the B/BK/91, B/NY/90, B/SD/89 and B/TX/91 viruses. The amino acid sequences of the B/HK/89, B/GD/89 and B/TX/90 viruses were more related to B/YM/88 but these viruses were antigenically indistinguishable from viruses on the B/NY/90 lineage. B/VI103 was placed on a sub-lineage with B/SH/87, the earliest B/YM/88-like virus identified. See Rota, P.A. et al., Virology 175:59-68 (1990).

The recent B/VI/87-like viruses were similar at the amino acid level including B/IN/89 which was antigenically distinct. The more recent B/VI/87-like viruses were placed on a separate sub-branch from B/TX/88, a variant isolated during the 1988 epidemic in the United States.

Figure 3:
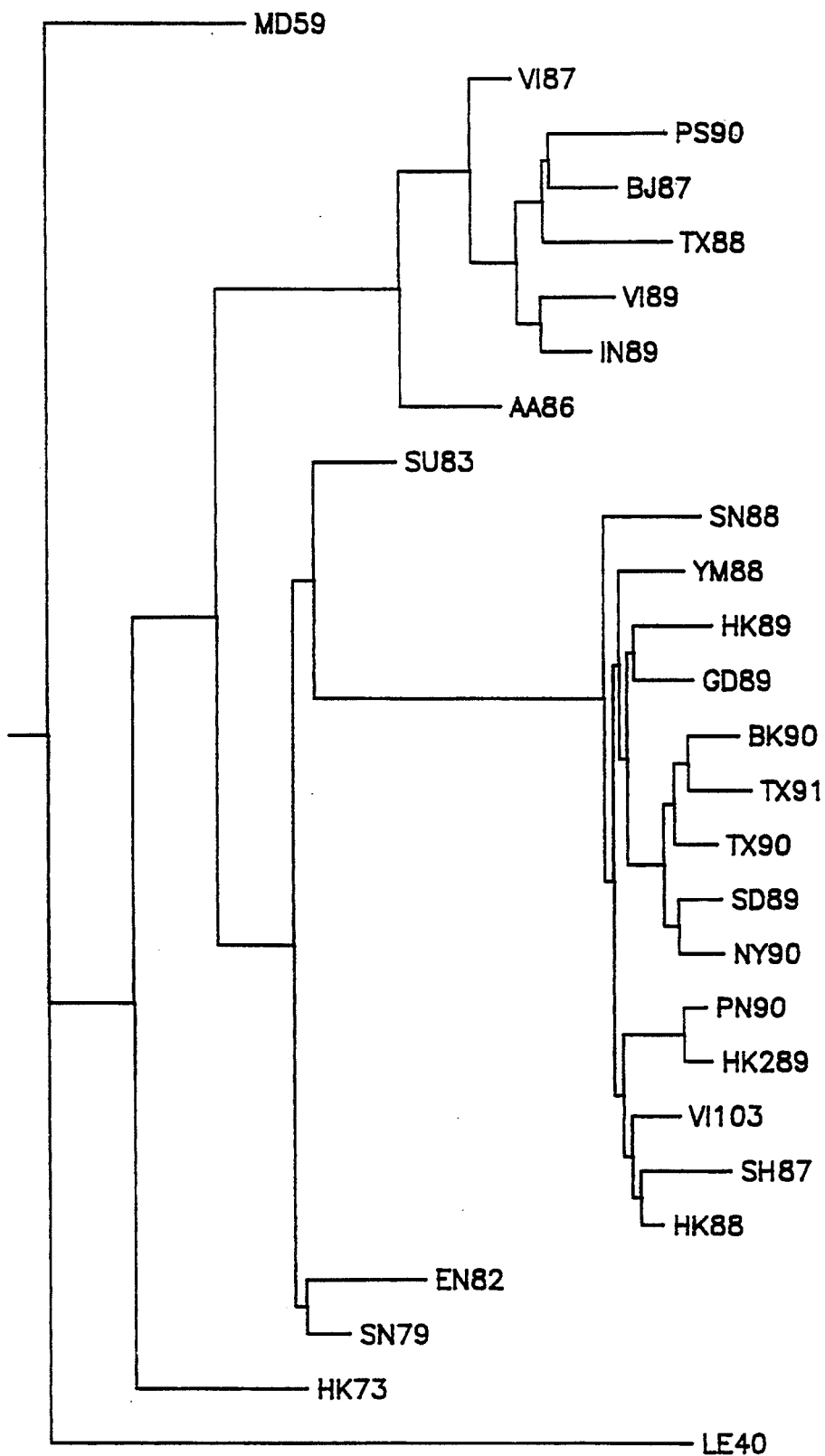
FIG. 3. Evolutionary relationships of influenza B viruses from 1940 to 1991. Phenogram was drawn using the DNAML and DRAWGRAM programs and is based on the total number of nucleotide differences between viruses. Sequences from previous reports are: LE40: B/Lee/40; HK73: B/Hong Kong/73, MD59: B/Maryland/59; SN79: B/Singapore/222/79; EN82: B/England/222/82; AA86: B/Ann Arbor/i/86, SU83: B/USSR/100/83, SN88: B/Singapore/7/88, SH87: B/Shanghai/12/87, B/HK/88: B/Hong Kong/14/88, VI87, YM88, BJ87, TX88.

The phenogram in FIG. 3 shows the evolutionary relationships of the recent influenza B isolates and several previously characterized strains based on the nucleotide substitution patterns. The separation of the B/VI/87 and B/YM/88 lineages and the presence of multiple sub-lineages within each main lineage are shown. The arrangement of the viruses from 1989-1991 on this tree is similar to the arrangement for these viruses based on the amino acid substitutions shown in FIG. 2. The relationships observed after the sequences of influenza B viruses isolated before 1979 were included in the analysis suggested that the branchpoint between the presently co-circulating lineages occurred between 1973 and 1979.

Figure 4:
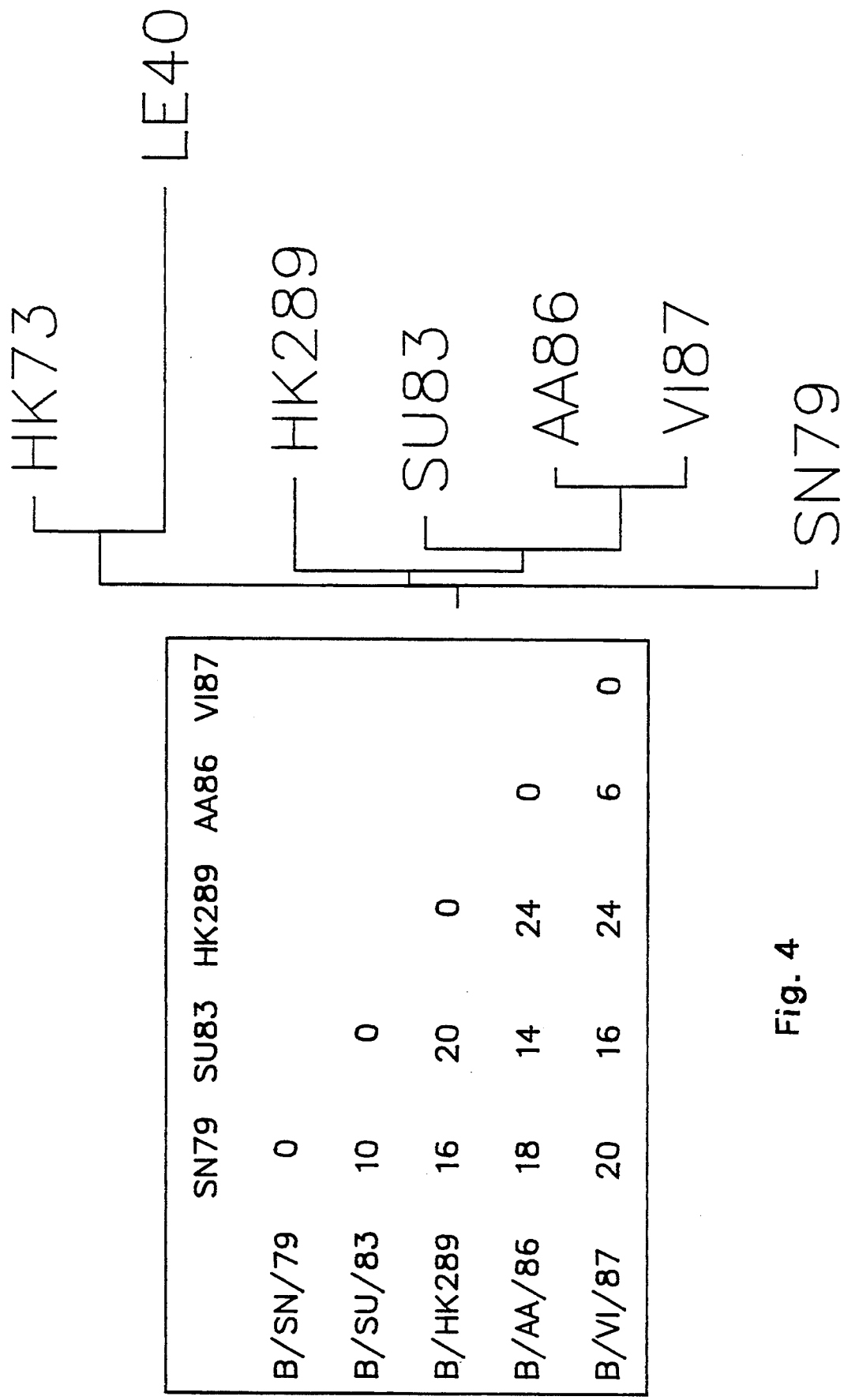
FIG. 4. Changes in the deduced amino acid sequences of the HA2 domains of influenza B viruses. Sequence of the HA2 of SN79 was determined by Verhoeyen, M., Rompuy, L., Jou, W., Huylebroeck, D. & Fiers, W., "Complete nucleotide sequence of the influenza B/Singapore/222/79 virus hemagglutinin gene and comparison with the B/Lee/40 hemagglutinin," *Nucleic Acids Res.* 11:4703–4712 (1983).

To complete the sequence analysis of the HAs from viruses on either the B/YM/88 or B/VI/87 lineages the nucleotide and deduced amino sequences of the HA2 domains of B/SU/83, B/AA/86, B/HK289 and B/VI/87 were determined and compared to several other influenza type B viruses. As expected, few amino acid changes were detected over 10 years. See FIG. 4. However, there were as many as 24 nucleotide changes between the HA2 domains of B/VI/87 and B/HK289. The nucleotide changes were used to construct an evolutionary tree which indicated that the HA2 domains of the HA of influenza B had an evolutionary pattern similar to that of the HA1 domain in that the B/YM/88-like virus and the B/VI/87-like viruses were placed on separate lineages. Table 4E which shows evolutionary relationships of the HA2 domains of influenza type B viruses based on the nucleotide changes. Total number of changes are shown in the inset table. Tree was drawn using the TREE program as described herein.

These data permitted a comparison of the rates of evolution for the HA1 and HA2 domains of the influenza B virus HA. For the 12 year period from 1979 to 1991, the nucleotide substitution rate for HA1 (0.236±0.04%/year) was similar to the rate for HA2 (0.196±0.06%/year). However, the rate of amino acid change was 0.30%/year for HA1 compared to 0.056%/year for HA2 and while approximately 40% of the nucleotide changes in HA1 coded for amino acid substitutions, only 8.7% of the nucleotide changes in HA2 caused changes in the HA2 protein.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference. Unless mentioned otherwise, the techniques employed or contemplated herein are standard methodologies well known to one of ordinary skill in the art. The materials, methods and examples are illustrative only. Thus, the invention is not limited by the preceding description, but rather by the claims that follow.

TABLE 4A-D

| SEQ. I.D. No. | STRAIN |
| --- | --- |
| 27, 28 | V187 |
| 29, 30 | BJ87 |
| 1, 2 | PS89 |
| 3, 4 | IN89 |
| 5, 6 | V189 |
| 31, 32 | YM88 |
| 7, 8 | GD89 |
| 9, 10 | HK89 |
| 11, 12 | HK289 |
| 13, 14 | VI103 |
| 15, 16 | SD89 |
| 17, 18 | PN90 |
| 19, 20 | NY90 |
| 21, 22 | TX90 |
| 23, 24 | BK91 |
| 25, 26 | TX91 |

TABLE 4A

```
           1                                                                                          100
           DRICTGITSSNSPHVVKTATQGEVNVTGVIPLTTTPTKSHFANLKGTKTRGKLCPKCLNCTDLDVALARPKCMGTIPSAKASILHEVKPVTSGCFPIMHD
VI87
BJ87
PS89                    Q
IN89                                                                              T                         F
VI89                                                                              T                         F

DRICTGITSSNSPHVVKTATQGEVNVTGVIPLTTTPTKSHFANLKGTKTRGKLCPNCLNCTDLDVALARPMCMGTIPSAKASILHEVRPVTSGCFPIMHD
YM88
GD89                                                                                         I
HK89
HK289                                                                             V          T
VI103                                                                             V
SD89                                                                              I          T
PN90                                                                              V
NY90                                                                              I
TX90                                                                              I
BK91                                                                              I                         R
TX91                                                                              I
```

TABLE 4B

```
       101                                                                                                    200
       RTKIRQLPNLLRGYEBHIRLSTHNVINAETAPGGPYKVGTSGSCPNVTNGNGFFATMAWAVPKNDNKTATNPLTVEVPYICTEGEDQITVWGFHSDSETQ
VI87
BJ87                                                                       N                                                     N A
PS89                         I                                                                                                   N A
IN89                         I             K                      R                                                              N
VI89                         I                                                            S                    I                 N I

RTKIRQLPNLLRGYENIRLSTHNVINAERAPGGPYRLGTSGSCPNVTSRNGFFATMAWAVPRDN.K.TATNPLTVEVPYICTKGEDQITVWGFHSDDKTQ
YM88                                                                  S                                                         K
GD89                                                                  S                                                         S
HK89          I                                                       D                                                         S
HK289                Q    G                                                                                                      N A
VI103                                                                 S                                              A          S
SD89                 Q                                                D                                                         N
PN90                                                                  S                                                         N
NY90                                                                  S                                                         N
TX90                                                                  KS                                                        N N
BK91                                                                  S                                                         N
TX91                                                                                                                            N I
```

TABLE 4C

```
      201                                                                              300
VI87  MVKLYGDSKPQKFTSSANGVTTHYVSQIGGFPNQAEDGGLPQSGRIVVDYMVQKSGKTGTITYQRGILLPQKVWCASGRSKVIKGSLPLIGEADCLHEKY
BJ87
PS89                                                                                  R
IN89                                                                                  R
VI89
YM88  MKKLYGDSNPQKFTSSANGVTTHYVSQIGDFPNQTEDGGLPQSGRIVVDYMVQKPGKTGTIVYQRGVLLPQKVWCASGRSKVIKGSLPLIGEADCLHAKY
GD89   N
HK89   N                                                                              E
HK289  N                                                                              E
VI103                                              G
SD89                                               G                                  E
PN90   N                                           G
NY90   N                                           G                                  E
TX90   N                                           G
BK91   N                                           G                                  E
TX91   N             V                             G                                  E
```

TABLE 4D

|  | 301 | 347 |
|---|---|---|
| VI87 | GGLNKSKPYYTGEHAKAIGNCPIWVKTPLKLANGTKYRPPAKLLKER | |
| BJ87 | | |
| PS89 | | |
| IN89 | | |
| VI89 | | |
| | | |
| YM88 | GGLNKSKPYYTGEHAKAIGNCPIWVKTPLKLANGTKYRPPAKLLKER | |
| GD89 | | |
| HK89 | | |
| HK289 | | |
| VI103 | | |
| SD89 | | |
| PN90 | | |
| NY90 | | |
| TX90 | | |
| BK91 | | |
| TX91 | | |

TABLE 4E

```
       348                                                                                 447
SN79   GFFGAIAGFLEGGWEGMIAGWHGYTSHGAHGVAVAADLKSTQEAINKITKNLNSLSELEVKNLQRLSGAMDELHNEILELDEKVDDLRADTISSQIELAV
SU83
AA86                                                       E
VI87
HK289

448                                                                                 547
SN79   LLSNEGIINSEDEHLLALERKLKKMLGPSAVDIGNGCFETKHKCNQTCLDRIAAGTFNAGEFSLPTFDSLNITAASLNDDGLDNHTILLYYSTAASSLAV
SU83                                                                                       Q
AA86                       E
VI87
HK289

548              570
SN79   TLMIAIFIVYMVSRDNVSCSICL
SU83
AA86
VI87
HK289
```

TABLE 5

```
       0                                                        49
Vi87   ATGAAGGCA ATAATTGTAC TACTCATGGT AGTAACATCC AATGCAGATC
Ym88                                                      C
In89
Vl89
Ps89
Tx91                                                      C
Bk91                                                      C
Gd89                                                      C
Hk89                                                      C
Hk289                                                     C
Sd89                                                      C
Vi103                                                     C
Tx90                                                      C
Ny90                                                      C
Pn90                                                      C 50                                                       99
Vi87   GAATCTGCAC TGGGATAACA TCGTCAAACT CACCCCATGT GGTCAAAACT
Ym88                        T          T                   A
IN89
Vl89
Ps89                                   C                   C
Tx91                        T          T                   A
Bk91                        T          T                   A
Gd89                        T          T                   A
Hk89                        T          T                   A
Hk289                       T          T                   A
Sd89                        T          T                   A
Vi103                       T          T                   A
Tx90                        T          T                   A
Ny90                        T          T                   A
Pn90                        T          T                   A 100                                                      149
Vi87   GCTACTCAAG GGGAAGTCAA TGTGACTGGT GTGATACCAC TGACAACAAC
Ym88              T
In89
Vl89
Ps89
Tx91
Bk91
Gd89
Hk89
Hk289
Sd89
Vi103
Tx90
Ny90
Pn90

150                                                      199
Vi87   ACCAACCAAA TCTCATTTTG CAAATCTCAA AGGAACAAAA ACCAGAGGGA
Ym88            A                                  G
In89   C
Vl89   C
Ps89   C                                  G                T
Tx91            A                                  G
Bk91            A                                  G
Gd89            A                                  G
Hk89            A                                  G
Hk289           A              A                   G
Sd89            A                                  G
Vi103           A                                  G
Tx90            A                                  G
Ny90            A                                  G
Pn90            A              A                   G
```

-continued

```
           200                                                        249
Vi87       AACTATGCCC AAAGTGTCTC AACTGCACAG ATCTGGACGT GGCCTTGGCG
Ym88                  C                                T
In89
Vl89
Ps89                  A
Tx91                  C                                T
Bk91                  C                                T
Gd89                  C                                T
Hk89                  C                                T
Hk289                 C                                T
Sd89                  C                                T
Vi103                 C                                T
Tx90                  C                                T
Ny90                  C                                T
Pn90                  C                                T 250                                                        299
Vi87       AGACCAAAGT GCATGGGGAC CATACCTTCG GCAAAAGCTT CAATACTCCA
Ym88            T     T
In89                    C
Vl89        G           C
Ps89                    C                                       T
Tx91            T     T    A
Bk91            T     T    A
Gd89            T     T           T
Hk89            T     T
Hk289           T     TG          C
Sd89            T     T    A
Vi103           T     TG
Tx90            T     T    A
Ny90            T     T    A
Pn90            T     TG          C 300                                                        349
Vi87       TGAAGTCAAA CCTGTTACAT CTGGGTGCTT CCTATAATG CACGACAGAA
Ym88       C            G                   C
In89       C                                T
Vl89       C                                T
Ps89       C
Tx91       C           GG                   C
Bk91       C           G                    C
Gd89       C           G                    C
Hk89       C           G                    C
Hk289      C           G                    C
Sd89       C           G                    C
Vi103      C           G                    C
Tx90       C           GG                   CA
Ny90       C           G                    C
Pn90       C           G                    C 350                                                        399
Vi87       CAAAAATTAG ACAGCTACCC AATCTTCTCA GAGGATACGA ACATATCAGG
Ym88            C                                T    A          A
In89
Vl89
Ps89
Tx91            C                                T    A          A
Bk91            C         A                      T    A          A
Gd89            C                                T    A          A
Hk89            C T                              T    A    T     A
Hk289           C                                T    A          A
Sd89                                             T    A          A
Vi103           C                                T    A          A
Tx90            C                                T    A          A
Ny90            C                                T    A          A
Pn90            C                                T    A          A
```

```
        400                                                         449
Vi87    TTATCAACCC ATAACGTTAT CAACGCAGAA ACGGCACCAG GAGGACCCTA
Ym88                                                G
In89
Vl89                                                A
Ps89
Tx91                                                G
Bk91                                                G
Gd89               T                                G
Hk89                                                G
Hk289              A                   T            GA
Sd89                                                G
Vi103                                               GG
Tx90                                                G
Ny90                                                G
Pn90               A                                GA 450                                                         499
Vi87    CAAAGTTGGA ACCTCAGGGT CTTGCCCTAA CGTTACCAAT GGAAACGGAT
Ym88       G C              A                     G A
In89         A            A
Vl89         A
Ps89         A
Tx91       G C              A                     G A        G
Bk91       G C              A                     G AA       G
Gd89       G C                                    G A        G
Hk89       G C              A                     G A        G
Hk289      G C              A                     G A        G
Sd89       G C              A             T       G A        G
Vi103      G C              A                     G A
Tx90       G C              A                     G A        G
Ny90       G C              A                     G A        G
Pn90       G C              A                     G A        G 500                                                         549
Vi87    TCTTCGCAAC AATGGCTTGG GCTGTCCCAA AAAACGACAA CAACAAAACA
Ym88                                     GGG  A  OO O   AOOO
In89
Vl89
Ps89            T
Tx91                                     GGG  A  OO O   AOOO
Bk91                                     GGG  A  OO O   AOOO
Gd89                                     GGG  A  OO O   AOOO
Hk89                                     GGG  A  OO O   AOOO
Hk289                                    GGG  A  OO O   AOOO
Sd89                                     GGG  A  OO O   AOOO
Vi103                                    GGG  A  OO O   AOOO
Tx90                                     GGG  A  OO O   AOOO
Ny90                                     GGG  A  OO O   AOOO
Pn90                                     GGG  A  OO O   AOOO 550                                                         599
Vi87    GCAACAAATC CATTAACAGT AGAAGTACCA TACATTTGTA CAGAAGGAGA
Ym88       G         C                              C     A
In89
Vl89         T
Ps89                                A
Tx91       G C       C                                    A
Bk91       G C       C                                    A
Gd89       G         C                                    A
Hk89       G         C                                    A
Hk289      G         C                                    A
Sd89       G C       C                                    A
Vi103      G         C                             G      A
Tx90       G C       C                                    A
Ny90       G C       C                                    A
Pn90       G         C                                    A 600                                                         649
Vi87    AGACCAAATT ACTGTTTGGG GGTTCCACTC TGATAGCGAA ACCCAAATGG
Ym88                   T             GA A                   A
In89                        T            A
Vl89              C                      A        T
Ps89                                     A      G
Tx91                                 T   A A      T         A
Bk91                                 T   A A      A         A
Gd89                                 T   AAA                A
Hk89                                 T   A                  A
Hk289                                T   A                  A
Sd89                                 T   A                  A
```

-continued
```
Vi103                                    A A    G       A
Tx90                            T        A A            A
Ny90                            T        A A            A
Pn90                            T        A A            A
```

```
         650                                                  699
Vi87     TAAAACTCTA TGGAGACTCA AAGCCTCAGA AGTTCACCTC ATCTGCCAAT
Ym88     A                     T      A
In89                                                           C
Vl89
Ps89                                                           C
Tx91     AC                    T      A  A
Bk91     AC                    T      A                      T
Gd89     A  C                  T      A
Hk89     A  C                  T      A
Hk289    A  C                  T      A
Sd89     A                     T      A
Vi103    A  C                  T      A
Tx90     A  C                  T      A  A
Ny90     A  C                  T      A
Pn90     A  C                  T      A
```

```
         700                                                  749
Vi87     CGAGTAACCA CACATTACGT TTCACAGATT GGTGGCTTCC CAAATCAAGC
Ym88                T          T             A                A
In89         G
Vl89
Ps89         G
Tx91                T          T                              A
Bk91                T          T                              A
Gd89                T          T          A                   A
Hk89                T          T          A                   A
Hk289               T          T                              A
Sd89                T          T                              A
Vi103               T          T                              A
Tx90                T          T                              A
Ny90                T          T                              A
Pn90                T          T                              A
```

```
         750                                                  799
Vi87     AGAAGACGGA GGGCTACCAC AAAGCGGTAG AATTGTTGTT GATTACATGG
Ym88                          C
In89
Vl89
Ps89
Tx91                          C
Bk91                          C
Gd89                          C
Hk89                          C
Hk289                         C
Sd89                          C
Vi103                         C
Tx90                          C
Ny90                          C
Pn90                          C
```

```
         800                                                  849
Vi87     TGCAAAAATC TGGAAAAACA GGAACAATTA CCTACCAAAG AGGTATTTTA
Ym88         C       G            AG T    T          G        G
In89
Vl89
Ps89
Tx91         C       G             G T    T          G
Bk91         C       G             G T    T          G        G
Gd89         C       G             G T    T          G        G
Hk89         C       G  T          G T    T          G        G
Hk289        C       G             G T    T          G        G
Sd89         C       G             G T    T          G        G
Vi103        C       G             G T    T          G        G
Tx90         C       G             G T    T          G        G
Ny90         C       G        G    G T    T          G        G
Pn90         C       G             G T    T          G        G
```

-continued

```
       850                                                              899
Vi87   TTGCCTCAAA AAGTGTGGTG CGCAAGTGGC AGGAGCAAGG TAATAAAAGG
Ym88              G
In89
Vl89
Ps89
Tx91        A         G          T
Bk91                  G          T
Gd89                  G
Hk89                  G
Hk289                 G
Sd89                  G          T
Vi103                 G
Tx90        A         G
Ny90                  G          T
Pn90                  G
```

```
       900                                                              949
Vi87   GTCCTTGCCT TTAATTGGTG AAGCAGATTG CCTCCACGAA AATACGGTG
Ym88                                               T         C
In89              C
Vl89              C
Ps89              C        CG
Tx91                                               T
Bk91                                               T
Gd89                                               T         C
Hk89                                               T
Hk289                                              T
Sd89                                               T
Vi103                                              T         C
Tx90                                               T         C
Ny90                                               T
Pn90                                               T         C
```

```
       950                                                              999
Vi87   GATTAAACAA AAGCAAGCCT TACTACACAG GAGAACATGC AAAAGCCATA
Ym88
In89              A                     G
Vl89                                    G
Ps89              A                     G
Tx91                                    T
Bk91
Gd89
Hk89
Hk289
Sd89
Vi103
Tx90
Ny90                        T
Pn90
```

```
       1000                                                             1049
Vi87   GGAAATTGCC CAATATGGGT GAAAACACCC TTGAAGCTGG CCAATGGAAC
Ym88                         T                       T
In89
Vl89
Ps89
Tx91                                    T            T
Bk91                                    T            T
Gd89                                    T            T
Hk89        G         G                 T            T
Hk289                                   T            T
Sd89                                    T            T
Vi103                                   T            T
Tx90                                    T            T
Ny90                                    T            T
Pn90                  A                 T            T
```

5,374,717

|       | 1050 | | 1086 |
|-------|------|------|------|
| Vi87  | CAAATATAGA | CCTCCTGCAA AACTATTAAA | GGAAAGG |
| Ym88  | | | |
| In89  | | | |
| Vl89  | | | |
| Ps89  | | | |
| Tx91  | | | |
| Bk91  | | | |
| Gd89  | | | |
| Hk89  | | | |
| Hk289 | | | |
| Sd89  | | C | |
| Vi103 | | | |
| Tx90  | | | |
| Ny90  | C | C | |
| Pn90  | | | |

---

What is claimed is:

1. An isolated nucleic acid having a nucleotide sequence selected from the group consisting of SEQ. I.D. Nos. 1, 3, 5, 7, 9, 11, 13, 15, 17, 19, 21, 23, and 25.

2. A nucleic acid of claim 1 wherein the nucleotide sequence is that of B/IN/89, as shown in SEQ. I.D. No. 3.

3. A nucleic acid of claim 1 wherein the nucleotide sequence is that of B/HK/289, as shown in SEQ. I.D. No. 11.

4. A nucleic acid of claim 1 wherein the nucleotide sequence is that of B/PN/90, as shown in SEQ. I.D. No. 17.

5. A nucleic acid of claim 1 wherein the nucleotide sequence is that of B/BK/91, as shown in SEQ. I.D. No. 23.

6. A nucleic acid of claim 1 wherein the nucleotide sequence is that of B/VI/89, as shown in SEQ. I.D. No. 5.

7. A nuclei acid of claim 1 wherein the nucleotide sequence is that of B/NY/90, as shown in SEQ. I.D. No. 19.

8. A nucleic acid of claim 1 wherein the nucleotide sequence is that of B/HK/89, as shown in SEQ. I.D. No. 9.

* * * * *

UNITED STATES PATENT AND TRADEMARK OFFICE
CERTIFICATE OF CORRECTION

PATENT NO. : 5,374,717
DATED : Dec. 20, 1994
INVENTOR(S) : Rota et al.

It is certified that error appears in the above-indentified patent and that said Letters Patent is hereby corrected as shown below:

In column 113, line 6 of claim 7, please delete "nuclei" and substitute therefor, --nucleic--.

Signed and Sealed this

Eleventh Day of April, 1995

*Attest:*

BRUCE LEHMAN

*Attesting Officer*     *Commissioner of Patents and Trademarks*